(12) United States Patent
Connally

(10) Patent No.: US 8,779,390 B2
(45) Date of Patent: Jul. 15, 2014

(54) AUTO-SYNCHRONOUS FLUORESCENCE DETECTION METHOD AND APPARATUS

(75) Inventor: Russell Connally, Marsfield (AU)

(73) Assignee: MacQuarie University, New South Wales (AU)

( * ) Notice: Subject to any disclaimer, the term of this patent is extended or adjusted under 35 U.S.C. 154(b) by 681 days.

(21) Appl. No.: 12/991,474

(22) PCT Filed: May 13, 2009

(86) PCT No.: PCT/AU2009/000596
§ 371 (c)(1),
(2), (4) Date: Nov. 8, 2010

(87) PCT Pub. No.: WO2009/137875
PCT Pub. Date: Nov. 19, 2009

(65) Prior Publication Data
US 2011/0057119 A1    Mar. 10, 2011

(30) Foreign Application Priority Data
May 13, 2008    (AU) ................ 2008902350

(51) Int. Cl.
*G01N 21/64* (2006.01)
*G02B 21/16* (2006.01)
*G02B 26/04* (2006.01)

(52) U.S. Cl.
CPC .... *G01N 21/6458* (2013.01); *G01N 2021/6463* (2013.01); *G02B 21/16* (2013.01); *G02B 26/04* (2013.01); *G01N 21/6408* (2013.01)
USPC .................................................... 250/459.1

(58) Field of Classification Search
CPC .......... G01N 21/6428; G01N 21/6445; G01N 21/6408; G01N 21/64; G01N 21/66
USPC ............................................ 250/491.1, 459.1
See application file for complete search history.

(56) References Cited

U.S. PATENT DOCUMENTS

| 3,433,987 A | 3/1969 | Thees |
| 3,526,448 A | 9/1970 | Senseney .................. 350/272 |

(Continued)

FOREIGN PATENT DOCUMENTS

| EP | 0 081 974 | 6/1983 | .............. G05B 5/01 |
| EP | 0081947 A1 | 6/1983 | |
| WO | WO2005/005038 | 1/2005 | ................ B01J 8/22 |

OTHER PUBLICATIONS

Patent Examination Report No. 1 issued Dec. 4, 2013 in counterpart Australian patent Application No. 2009246048 (3 pages).
Marriott, G. et al., "Time-Resolved Delayed Luminescence Image Microscopy Using an Europium Ion Chelate Complex", Biophysical Journal, vol. 67, Sep. 1994, pp. 957-966.

(Continued)

*Primary Examiner* — David Porta
*Assistant Examiner* — Djura Malevic
(74) *Attorney, Agent, or Firm* — Goodwin Procter LLP

(57) ABSTRACT

An apparatus for time-gated fluorescence or luminescence detection includes gating means (206) arranged to alternately permit light from an excitation source (242) to be directed to a sample (235) along a first communication path (231, 232), and then permit light emitted from the sample to be directed to a detector (246) along a second communication path (237, 238) while blocking the first communication path (231, 232): The gating means (206) may comprise a single chopper wheel or apertured disc, or a rotating or oscillating arm, and may further comprise one or more reflective facets (207). The gating means (206) may be driven via a magnetic rotor, with a ferrite bead placed to offset rotor magnets with respect to drive coils, when at rest, so as to assist with self starting.

33 Claims, 24 Drawing Sheets

(56) References Cited

U.S. PATENT DOCUMENTS

| | | | |
|---|---|---|---|
| 3,700,942 A | 10/1972 | Alth ............................. | 210/164 |
| 4,954,714 A | 9/1990 | Pollak et al. ................... | 250/458 |
| 6,839,134 B2 | 1/2005 | Saito et al. ..................... | 356/317 |
| 2003/0160151 A1* | 8/2003 | Zarate et al. ............... | 250/208.1 |
| 2009/0175412 A1* | 7/2009 | Grodzins et al. ............... | 378/57 |
| 2010/0090127 A1* | 4/2010 | Yekta et al. ................ | 250/459.1 |

OTHER PUBLICATIONS

Soini, E.J., et al., "Lanthanide chelates as new fluorochrome labels for cytochemistry", Journal of Histochemistry & Cytochemistry, vol. 36, No. 11, 1988, pp. 1449-1451.

Verwoerd, N.P., et al., "Use of Ferro-Electric Liquid Crystal Shutters for Time-Resolved Fluorescence Microscopy", Cytometry, vol. 16, Wiley-Liss, Inc., 1994, pp. 113-117.

* cited by examiner

*Time resolved Fluorescence – phase shift*

*Time gated Fluorescence – pulse fluorometry*

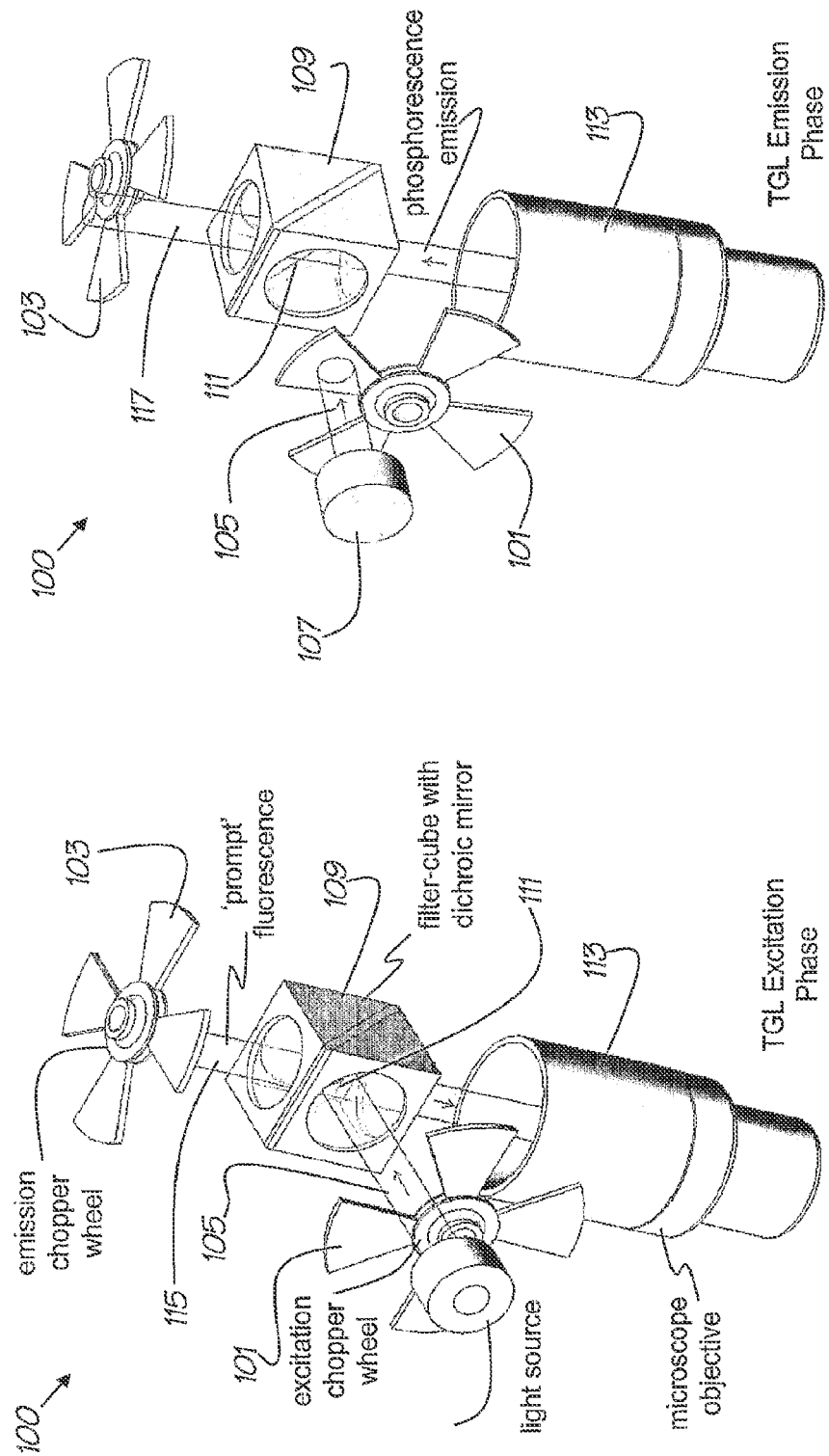

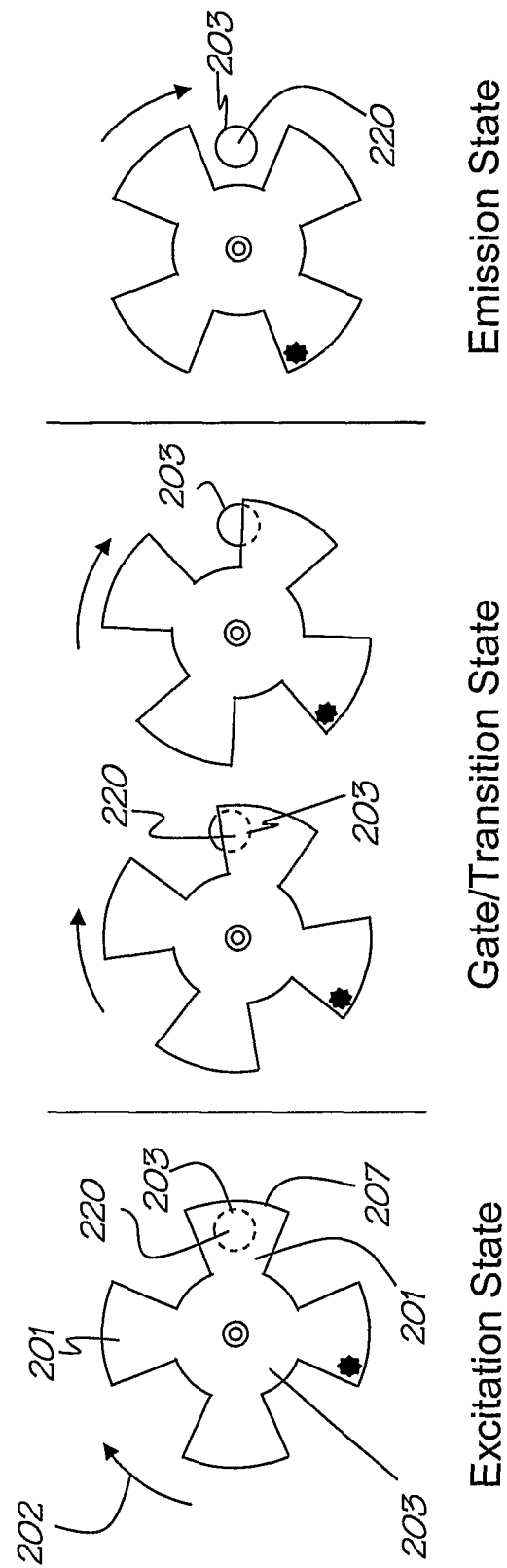

AUTO-SYNCHRONOUS FLUORESCENCE DETECTION METHOD AND APPARATUS

CROSS REFERENCE TO RELATED APPLICATION

This application is a national stage filing under 35 U.S.C. §371 of International Application No. PCT/AU2009/000596, filed May 13, 2009, which is hereby incorporated by reference in its entirety.

TECHNICAL FIELD

The present invention relates to time gated luminescence detection schemes and in particular to apparatus and methods for providing a time gated luminescence detection system.

The invention has been developed primarily for use as apparatus methods, and systems for provision of auto-synchronous time gated luminescence detection schemes and microscope systems and will be described hereinafter with reference to this application. However, it will be appreciated that the invention is not limited to this particular field of use.

BACKGROUND OF THE INVENTION

Any discussion of the background art throughout the specification should in no way be considered as an admission that such background art is prior art, nor that such background art is widely known or forms part of the common general knowledge in the field.

Fluorescence is the name given to the process of light emission following a transition between energy levels that occur without a change in the electron spin state. It is typically a short-lived phenomenon with excited-state lifetimes measured in nanoseconds for most common fluorophores. Phosphorescence on the other hand describes excited state transitions that involve a change in spin-state, and when these transitions are spin-forbidden, emission lifetimes can extend for several thousand times longer than fluorescence decay.

Fluorescence based techniques provide a powerful means for both the qualitative and quantitative detection of biomolecules. Fluorescence methods afford a sensitive means for the detection of single molecules, however, fluorescent probes (also referred to as fluorescent markers), used to "label" a particular feature in a sample (for example a particular organism or bio-molecule such as *Giardia* in a water sample) to determine the presence and/or number of features in the sample, lose much of their discriminatory power in the presence of autofluorescence. Organic and inorganic autofluorophores are ubiquitous in nature and some materials fluoresce with great intensity, obscuring or diminishing the visibility of synthetic fluorescent probes. Spectral selection techniques (emission and excitation filters) can reduce the problem but are not always applicable due to the abundance and spectral range of autofluorescence.

Using techniques such as time-resolved fluorescence microscopy (TRFM), it is possible to spatially discriminate fluorescent regions that differ by less than a nanosecond in fluorescence lifetime. TRFM techniques operate in the frequency domain, usually employing a sinusoidal modulation of the excitation source to induce a phase ($\phi$) delayed modulation in fluorescence intensity from which fluorescence lifetime can be determined using $\Delta\phi$ and modulation frequency parameters (FIG. 1A).

Time-gated luminescence (TGL) techniques operate within the time-domain and are directed towards detection of events that occur at much longer time-scales (phosphorescence).

For TGL operation as shown in FIG. 1B, the detector is gated off whilst a brief pulse of light is used to excite emission from the sample. The detector is maintained in the off-state for a resolving period (gate-delay) whilst short-lived (<1 μs) fluorescence fades beyond detection. The detector is then enabled to capture luminescence in the absence of autofluorescence, greatly increasing the signal-to-noise ratio. As can be seen, pulse fluorometry or time-gated luminescence techniques operate on much longer timescales. Fluorescence lifetime constants can be determined by observing intensity in the fluorescence signal after different gate delays. A key advantage of TGL techniques is the suppression of short-lived fluorescence to increase the signal-to-noise ratio (SNR).

Whilst it is possible to discriminate probe fluorescence from autofluorescence using TRF techniques, a simpler and much less costly TGL instrument can be employed if a suitable luminescent probe is available. Lanthanide ($Eu^{3+}$ or $Tb^{3+}$) chelate luminescent probes have exceptionally long phosphorescence lifetimes ($\tau$) reaching milliseconds for some compounds. Other compounds that have found wide application for TGL include the platinum and palladium (co-pro)porphyrins with lifetimes ranging from 10 to 1000 μs depending on their environment. The very large difference in $\tau$ between typical autofluorophores and the luminophores used for TGL has helped ensure useful results were gained even with simple instruments relying upon chopper-wheels.

The substantial increase in SNR afforded by TGL techniques is a critical factor when searching for rare target organisms encountered in autofluorescent environments. For example, the detection of *Cryptosporidium* oocysts in drinking water requires the filtration of large volumes of water and results in a matrix of mineral particles, algae, desmids and plant matter that is strongly autofluorescent. TGL microscopy has been demonstrated to greatly suppress this background and simplify the detection of both *Giardia* and *Cryptosporidium*, two important waterborne pathogens. There are instances where the detection of rare-event signals using conventional fluorescence techniques is exceedingly difficult (or impossible) and consequently, where TGL microscopy has greatest utility.

Luminescent probes based on the lanthanides $Eu^{3+}$ and $Tb^{3+}$ were described in the 1960's but effective immunofluorophores using these compounds were not reported until the early 1980's. TGL microscopes were built to exploit these novel compounds however various deficiencies in the instrumentation and luminescent probes resulted in relatively insensitive instruments. As technologies matured, improvements were made both in instrument design and probe quality. The evolution of TGL microscope instrumentation designed for the detection of phosphorescence ($\tau$>10 μs) is briefly discussed below.

With reference to FIG. 1B, TGL techniques employ an excitation pulse to excite photon emission from the sample. The excitation pulse ideally terminates abruptly (<1 μs) whilst the detector is maintained in the off-state for a predetermined time (the resolving period or gate delay), the duration of which is designed to permit short-lived fluorescence to decay. After the gate-delay has elapsed, the detector is gated on to initiate the start of the acquisition period to detect the fluorescence signal from the luminescent label, free of background noise from autofluorophores in the sample.

In 1988 Soini et al. [Soini E J, Pelliniemi L J, Hemmila I A, Mukkala V M, Kankare J J, Frojdman K, *Lanthanide chelates as new fluorochrome labels for cytochemistry*, Journal of Histochemistry and Cytochemistry 36(11) 1988 p. 1449-51] described a europium chelate that could be easily bound to bio-molecules to permit them to "re-test the old idea of time-resolved fluorescence microscopy in immunohistology and cytology". Using steady state excitation, it was shown that Eu-antibody labelled histology sections were visibly luminescent to the naked eye and would likely provide a means to improve signal to noise ratio under TGL conditions. The following year, Beverloo et al. described a Xenon flashlamp excited TGL microscope synchronized to a chopper wheel. Phosphorescence persists for orders of magnitude longer than prompt fluorescence and makes feasible the use of mechanical choppers for visualizing the phenomenon and the majority of early TGL instruments employed chopper wheels to isolate the excitation and detection states in a TGL cycle.

The first TGL microscope employing two phase locked chopper-wheels for pulse control (detection and excitation) was reported by Marriott et al. in 1994. FIGS. 2A and 2B details the essential features of such an instrument 100. Excitation chopper wheel 101 and emission chopper wheel 103 are shown with the chopper-blades positioned in their respective states for the excitation and detection (emission) states of a TGL cycle FIGS. 2A and 2B respectively). During the excitation state of FIG. 2A light 105 from excitation light source 107 passes between the blades of the excitation chopper 103 and is deflected by a dichroic mirror 109 in filter cube 111 and is focused by microscope objective 113 onto a sample under test (not shown). During this state, the prompt or autofluorescence 115 from short-lived autofluorophores in the sample is directed back through the microscope objective 113, and through the dichroic mirror 109, but is blocked from reaching the detector (not shown) by the emission chopper 103 i.e. in this state the excitation light source is open and the detector is closed. FIG. 2B shows the detection (emission) state of the TGL chopper where the blades of choppers 101 and 103 have moved such that light 105 from the excitation source 107 is blocked by the blades of the excitation chopper 101 whereas the phosphorescence 117 from the luminescently labelled sample passes through the blades of emission chopper 103 to the detector.

The detection-side chopper 103 is phase locked to the excitation chopper 101 by a control module (not shown) to maintain an arbitrary phase difference between the two. The TGL system 100 can be switched from delayed luminescence mode to 'prompt' mode by adjusting this phase angle.

As described above, the gate-delay is the intervening period between termination of the excitation pulse and commencement of the acquisition phase (see FIG. 1B). For most phosphorescent labels, decay follows single exponential kinetics ($I_0=I_i e^{-t/\tau}$) and emission decays substantially as the gate-delay interval approaches the luminescence lifetime. Unfortunately, the gate-delays typical for chopper based switching mechanisms are quite long (about 20 to 500 µs) in comparison to the emission decay time of the fluorescent labels and therefore the fluorescence has typically decayed quite significantly before the detection state is able to commence. Also, conventional time-gated luminescence microscopes incur substantial losses both during the excitation and emission/detection states as light passages through the dichroic filter cube. The dichroic mirror in the filter cube also has significant limitations on the particular wavelengths that are allowed to be either reflected on to the sample or to pass through to be detected due to the limitations in coating designs. Thus, such systems have severe limitations on the number of allowed wavelengths and the reflection/transmission bandwidth of the design wavelengths that are able to be utilised for the detection system. Such dichroic filter cubes are also expensive and complex to interchange causing significant barriers to the use of the TGL microscope system for different excitation sources or luminescent probes with different operating wavelengths.

Electronic shutters may be used to overcome the gate-delay limitation of chopper-wheel systems, for example ferro-electric liquid crystals (FELC) which rotate the plane of light polarization in response to an applied voltage and can serve as fast optical shutters. A TGL microscope was constructed by Verwoerd et al. in 1994 [Verwoerd N P, Hennink E J, Bonnet J, Van der Geest C R, Tanke H J, *Use of ferro-electric liquid crystal shutters for time-resolved fluorescence microscopy*, Cytometry 16(2) 1994 p. 113-7] in which the emission-plane chopper was replaced with two crossed LC shutters. For excitation, a Xenon-arc lamp was interrupted by a mechanical chopper to generate pulsed output; gating of the LC shutters was synchronized to the chopper wheel position. Whilst effective, the FELC shutters imposed a substantial insertion loss with transmission reduced to just 15% when fully open. A further limitation of chopper excitation schemes arises from the relatively slow rise and fall time of the pulse (for example, in the systems described by Verwoerd et al, the rise/fall time was 50 to 100 µs at a chopper rotation speed of 3,800 rpm). Excitation pulses with slow falling edges force extension of the gate-delay that leads ultimately, to a loss in SNR. The gain achieved by switching rapidly in the emission plane with the FELC shutter was offset by the slow falling edge of the excitation pulse.

Since 1994, the majority of the improvements in TGL microscope detection systems have been obtained by improvements in either the excitation source—flashlamp, visible and ultraviolet (UV) lasers, or light emitting diodes (LEDs)—and/or the detectors used to capture the fluorescent light with increasingly improved signal-to-noise ratio—image-intensified gated charge coupled device (CCD) and electron multiplying charge coupled device (EMCCD) detectors have been particularly successful as described in the inventor's earlier patent application PCT/AU2005/001606.

The basic requirements for TGL microscopy are relatively straightforward, a pulsed excitation source and a gated detector. However, the common features of the prior art TGL microscope systems to provide these basic requirements has been the dual shutter system (either using chopper wheels, electronic shutters, or a combination of both) similar to that depicted in FIGS. 2A and 2B. As previously described, this type of system requires that the phase of each of the excitation- and emission-side shutters are precisely synchronised with both the excitation source and the detector acquisition state. To achieve this, complex electronic phase matching circuitry and control systems are required, which are both expensive to implement and maintain. Furthermore, the detector systems that must be used with these TGL microscope systems are prohibitively expensive (typical cost of a TGL EMCCD detector at the time of writing is in the range of about $20,000 to $45,000).

The prohibitive cost of such systems means that they are not available on a large scale since only the most well-funded research facilities can purchase and maintain such items.

Therefore, there is a need for a TGL system that is simple to both implement and use.

SUMMARY OF THE INVENTION

According to a first aspect there is provided an apparatus for use in a time gated luminescence detection system. The apparatus may comprise a first communication portion for providing a first optical communication path between an illumination source location and a sample location. The apparatus may further comprise a second communication portion for providing a second optical communication path between the sample location and the detection location. The second communication portion may be operable to enable detection at the detection location of a desired optical emission from an illuminated sample which in use is located at the sample location via the second optical communication path. The second communication portion may also concurrently prevent optical communication on the first optical communication path. The apparatus may also comprise a gate portion for gating the first and second optical communication paths. The apparatus may be capable of being arranged to provide the first optical communication path, to gate the first and second optical communication paths and to provide the second optical communication paths in a sequential manner thereby to respectively place the apparatus in an excitation state, a gated state and a detection state.

According to an arrangement of the first aspect, there is provided an apparatus for use in a time gated luminescence detection system, the apparatus comprising:

a) a first communication portion for providing a first optical communication path between an illumination source location and a sample location;

b) a second communication portion for (i) providing a second optical communication path between the sample location and the detection location, the second communication portion being operable to enable detection at the detection location of a desired optical emission from an illuminated sample which in use is located at the sample location via the second optical communication path; and (ii) concurrently preventing optical communication on the first optical communication path;

c) a gate portion for gating the first and second optical communication paths;

the apparatus being capable of being arranged to provide the first optical communication path, to gate the first and second optical communication paths and to provide the second optical communication paths in a sequential manner thereby to respectively place the apparatus in an excitation state, a gated state and a detection state.

According to another arrangement of the first aspect, there is provided an apparatus for use in a time gated luminescence detection system, the apparatus configurable for movement between an excitation, a gated state and a detection state, the apparatus comprising: a first communication portion adapted to provide a first optical communication path between a first location and a second location whilst preventing optical communication between the second location and a third location; a second communication portion adapted to provide a second optical communication path between the second location and the third locations whilst preventing optical communication on the first optical communication path, and a gate portion for gating the first and the second communication paths.

In any of the arrangements of the apparatus described herein, the first location may be an illumination source location, the second location may be a sample location, and the third location may be a detection location, and vice versa.

In any of the aspects or arrangements described herein, the gate portion may be capable of one or more of: preventing optical communication on the first optical communication path; preventing optical communication on the second optical communication path; preventing optical communication between the first and the second locations; preventing optical communication between the second and the third locations; gating the excitation and the detection states; or gating an optical path of the apparatus or system. In particular arrangements, the gate portion may be integral with the first communication portion.

In any of the aspects or arrangements described herein, the apparatus, system or method may also comprise one or more of any of the following either taken alone or in any suitable combination.

The location of the first communication portion, the gate portion and the second communication portion may be fixed relative each other during movement of the apparatus such that, in use, repeated movement of the apparatus may provide autonomous synchronisation between the emission and detection states.

In an arrangement, the second communication portion may be a void space in the apparatus which is defined by the first communication portion. The second optical communication path may comprise the void space such that light propagating on the second optical communication path may propagate though the void space. In an alternate arrangement, the second communication portion may comprise a transparent portion. The second optical communication path may comprise the transparent portion such that light propagating on the second optical communication path may propagate though the transparent portion.

The apparatus may provide a self-synchronising time gated fluorescence detection system.

The first communication portion may comprise a reflector aligned for deflecting light between the illumination light source and the sample locations. At least a portion of the reflector may comprise the gate portion.

The apparatus may comprise an upper surface and a lower surface, the upper surface having a greater distal extent from the movement axis than the lower surface, wherein the first communication portion comprises a reflective surface distal the movement axis and contiguous with both the upper and lower surfaces and the distal extent of the apparatus.

In an alternate arrangement, the apparatus may comprise an upper surface and a lower surface, the upper surface having a greater distal extent from the movement axis than the lower surface, wherein the first communication portion comprises a reflective surface contiguous with the lower surface and distal to the movement axis, wherein the reflective surface is configured for reflecting light from a illumination light source proximal to the movement axis. The apparatus may comprise a further reflector proximal the movement axis for reflecting light from an external illumination light source to the reflective surface.

The first communication portion may comprise at least one elongate vane extending from the movement axis. The movement axis may be a pivot axis. The first communication portion may comprise plurality of vanes extending from the pivot axis. The pivot axis may be a rotation axis. The plurality of vanes may be equi-circumferentially spaced around the rotation axis. The apparatus may comprise, 1, 2, 3, 4, 5, 6, 7, 8 9 10 or more equi-circumferentially spaced vanes.

In the excitation state, the vane(s) may be adapted for blocking light from the sample location from impinging on the detection location. Also, in the excitation state, the first communication portion may be aligned with an external light emitting source to enable light from the light emitting source to traverse the first optical communication path to the sample location. The vane may comprise the gate portion such that when the apparatus is in the gated state intermediate the excitation and the detection states, light from the light emitting source is incident on the gate portion and prevented from impinging on the excitation location. In the gated state, light from the source location may also be incident on the gate portion and prevented from impinging on the detection location.

The second communication portion may comprise a substantially transparent portion through the apparatus for facilitating optical communication between the sample and detection locations. The second communication portion may comprise a plurality of substantially transparent portions.

In the detection state, the transparent portion may either: not deflect light from the illumination light source location; or facilitate light from the illumination light source location to be incident on a non-reflective portion of the apparatus.

In the excitation state, the reflector may be adapted for deflection of light from an external light emitting source located at the illumination light source location to a sample which in use is located at the sample location. The sample may comprise at least one autofluorophore responsive to light from the light source. The autofluorophore may emit autofluorescence with an autofluorescence lifetime when excited by a suitable light source.

In use, the purpose of the gated state may be to gate for a desired period of time unwanted fluorescence in a sample excited by a light source. The gate portion may be adapted to substantially prevent the autofluorescence from impinging on the detection location for a period of time of at least the autofluorescence lifetime.

The sample may comprise a probe fluorophore responsive to light from the light source. The probe fluorophore may emit probe fluorescence with a probe fluorescence lifetime greater than the autofluorescence lifetime when excited by a suitable light source. The desired optical emission may be the probe fluorescence.

The detection location may be adapted for receiving an optical detector for detection of the desired optical emission from the sample location in the detection state. The detector may detect light traversing the second optical communication path.

The reflector maybe arcuate. The gate portion may comprise two non-reflective portions adjacent the reflector. The non-reflective portions may be guard portions. The guard portions may be absorbing, non-reflective or absorbing and non-reflective. The guard portions may be reflective and disposed (e.g. at a different angle to the reflector) such that light from the external light emitting source incident on the guard portions may be directed away from the sample location. The apparatus may be adapted for use in conjunction with a continuous wave light emitting source. The guard portions may facilitate the use of a continuous wave light emitting source in a time-gated luminescence detection system. The continuous wave time-gated luminescence detection system may be an autosynchronous time-gated luminescence detection system. The guard portions may collectively represent between 10 and 60% of the width of the first communication portion. Alternatively, the guard portions may collectively represent between 10% and 55%, 10% and 50%, 10% and 45%, 10% and 40%, 10% and 35%, 20% and 60%, 20% and 55%, 20% and 50%, 20% and 45%, 20% and 40%, 20% and 35%, 25% and 60%, 25% and 55%, 25% and 50%, 25% and 45%, 25% and 40%, 25% and 35%, 35% and 60%, 35% and 55%, 35% and 50%, 35% and 45%, or 35% and 40%. of the width of the first communication portion and may be approximately 10%, 15%, 20%, 25%, 30%, 35%, 40%, 45%, 50%, 55% or 60%.

The reflector may be highly reflective for ultraviolet, visible or infrared optical wavelengths. The reflector may be highly reflective for optical wavelengths in the range of 150 nm to 2000 nm. The reflector may be highly reflective for optical wavelengths in the range of 150 nm to 400 nm. The reflector may be highly reflective for optical wavelengths in the range of 300 nm to 1000 nm. The reflector may be highly reflective for optical wavelengths in the range of 800 nm to 2000 nm. The reflector may be highly reflective for optical wavelengths in the range of 150 nm to 800 nm. The reflector may be simultaneously reflective for a plurality of wavelengths and may be simultaneously reflective for 2, 3, 4, 5, 6, 7, 8, 9, 10 or more wavelengths. The reflector may be selectively reflective for a plurality of wavelengths. The selective reflector may comprise an optical coating suitable for providing selective reflectivity at a plurality of desired wavelength. The optical coating may be a multi-layer coating. The coating may be an interference coating. The reflector may be configured to reflect a narrow band of the optical spectrum centred about the wavelength(s) the reflector is configured to reflect. The bandwidth of the spectrum about the wavelength(s) which the reflector is configured to reflect may be in the range of 0.01 to 50 nm, 0.01 to 40, 0.01 to 30, 0.01 to 25, 0.01 to 20, 0.01 to 15, 0.01 to 10, 0.01 to 5, 0.01 to 4, 0.01 to 3, 0.01 to 2, or 0.01 to 1, 0.01, 0.5, 0.01 to 0.1, 0.01 to 0.05, 0.05 to 50, 0.05 to 40, 0.05 to 30, 0.05 to 25, 0.05 to 20, 0.05 to 15, 0.05 to 10, 0.05 to 5, 0.05 to 4, 0.05 to 3, 0.05 to 2, 0.05 to 1, 0.05 to 0.05, 0.05 to 0.1, 0.1 to 50, 0.1 to 40, 0.1 to 30, 0.1 to 25, 0.1 to 20, 0.1 to 15, 0.1 to 10, 0.1 to 5, 0.1 to 4, 0.1 to 3, 0.1 to 2, or 0.1 to 1, 0.1, 0.05, 0.5 to 50, 0.5 to 40, 0.5 to 30, 0.5 to 25, 0.5 to 20, 0.5 to 15, 0.5 to 10, 0.5 to 5, 0.5 to 4, 0.5 to 3, 0.5 to 2, or 0.5 to 1 nm, and may be about 0.01, 0.02, 0.03, 0.04, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, or 50 nm or more.

The apparatus may further comprise a mover adapted to move the apparatus with respect to the movement axis. The mover may be configurable for sequentially: moving the apparatus to the excitation state; moving the apparatus to the gated state wherein the first optical communication path is gated by the gate portion; maintaining the apparatus in the gated state for a first period of time; and moving the apparatus to the detection state at a time after the first period. The mover may be adapted for continuous movement between the excitation state, the gated state and the detection state. The mover may be adapted for continuous repeated movement between the excitation state, the gated state and the detection state. The movement axis may be a pivot axis. The pivot axis may be a rotation axis and the apparatus may rotate about the rotation axis. The mover may be an electrical motor. The mover may be a direct current motor. The apparatus may comprise at least one magnet and the mover may be a magnetic drive mover. The apparatus may further comprise a start means. The start means may be adapted to co-operate with the mover to assist with self-starting of the apparatus. The start means may direct the apparatus to a selected rest position when not in operation. The selected rest position may be such that a portion of the apparatus is misaligned with the mover or a portion or component thereof. The start means may be a ferromagnetic object which may interact with the at least one magnet when the apparatus is not in operation to urge the apparatus into the selected rest position. The mover may be a variable speed mover. The variable speed mover may be a continuously variable speed mover.

The apparatus may be a rotor adapted for rotation about the movement axis. The rotor may be adapted to be driven into rotation by the mover. The rotor may be configurable for rotation speed of between 5,000 and 60,000 revolutions per minute. The rotor may be configurable for rotation speed of between 5,000 and 60,000 revolutions per minute. In other arrangements, the rotation speed may be in the range of 1 to 100,000, 100 to 100,000, 500 to 100,000, 500 to 90,000, 500 to 80,000, 500 to 70,000, 500 to 60,000, 500 to 50,000, 500 to 40,000, 500 to 30,000, 500 to 25,000, 500 to 20,000, 500 to 15,000, 500 to 12,000, 500 to 11,000, 500 to 10,000, 500 to 9,000, 500 to 8,000, 500 to 7,000, 500 to 6,000, 500 to 5,000, 500 to 4,000, 500 to 3,000, 500 to 2,000, 500 to 1,000, 1,000 to 30,000, 1,000 to 25,000, 1,000 to 60,000, 1,000 to 50,000, 1,000 to 40,000, 1,000 to 30,000, 1,000 to 20,000, 1,000 to 15,000, 1,000 to 12,000, 1,000 to 11,000, 1,000 to 10,000, 1,000 to 9,000, 1,000 to 8,000, 1,000 to 7,000, 1,000 to 6,000, 1,000 to 5,000, 1,000 to 4,000, 1,000 to 3,000, 1,000 to 2,000, 2,000 to 60,000, 2,000 to 50,000, 2,000 to 40,000, 2,000 to 30,000, 2,000 to 25,000, 2,000 to 20,000, 2,000 to 15,000, 2,000 to 12,000, 2,000 to 11,000, 2,000 to 10,000, 2,000 to 9,000, 2,000 to 8,000, 2,000 to 7,000, 2,000 to 6,000, 2,000 to 5,000, 2,000 to 4,000, 2,000 to 3,000, 2,500 to 30,000, 2,500 to 25,000, 2,500 to 20,000, 2,500 to 15,000, 2,500 to 12,000, 2,500 to 11,000, 2,500 to 10,000, 2,500 to 9,000, 2,500 to 8,000, 2,500 to 7,000, 2,500 to 6,000, 2,500 to 5,000, 2,500 to 4,000, 5,000 to 30,000, 5,000 to 25,000, 5,000 to 80,000, 5,000 to 75,000, 5,000 to 70,000, 5,000 to 65,000 5,000 to 60,000, 5,000 to 50,000, 5,000 to 40,000, 5,000 to 30,000, 5,000 to 20,000, 5,000 to 15,000, 5,000 to 12,000, 5,000 to 11,000, 5,000 to 10,000, 5,000 to 9,000, 5,000 to 8,000, 5,000 to 7,000, 5,000 to 6,000, and may be approximately 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 13,000, 14,000, 15,000, 20,000, 25,000, 30,000, 35,000, 40,000, 45,000, to 50,000, 55,000 or 60,000. In other arrangements, the rotation speed may be about 65,000, 70,000, 75,000 or about 80,000 rpm.

The apparatus may be adaptable for gating fluorescence during the intervening period between termination of the excitation state and commencement of the detection state. In particular, in one form the apparatus may be configurable to provide a variable gate delay whereby the time period of gating by the gate portion between termination of the excitation state and commencement of the detection state is capable of being varied as required. The apparatus may be coupled with a drive device or mover which may be operated at different speeds to provide correspondingly different gate delays as a result of correspondingly different gating time periods being realised by the gate portion. The drive device or mover may be a variable drive device or mover. The speed of the apparatus capable of being provided by the variable drive device may be variable such that the apparatus is capable of providing a variable gate delay. In this arrangement, the speed of the variable drive device can be set such that the gate portion of the apparatus blocks fluorescence for a required intervening period between the termination of the excitation state and commencement of the detection state. In another arrangement the apparatus may be adapted for providing a variable gate delay by including a variable drive device as part of the apparatus. The variable gate delay may be provided by varying the speed of a variable drive device coupled to or integral with the apparatus. When the apparatus is in operation, the variable gate delay may be provided by varying or selecting the width of the gate portion(s) of the apparatus for a given speed. In arrangements where the apparatus is a rotor apparatus, the variable gate delay may be provided by varying or selecting the width of the gate portion(s) of the apparatus for a given rotation speed.

The apparatus may be adapted to gate fluorescence during the intervening period between termination of the excitation state and commencement of the detection state. The gate portion(s) may be adapted to provide the gating. In particular, the gate portion(s) of the apparatus may be configured to provide a variable gate delay whereby the time period of gating by the gate portion between termination of the excitation state and commencement of the detection state is capable of being varied as required. The apparatus is coupled with a drive device or mover which is operated at different speeds to provide correspondingly different gate delays as a result of correspondingly different gating time periods being realised by the gate portion. The drive device or mover in particular arrangements is a variable drive device or mover. In particular arrangements, the movement speed of the apparatus provided by the variable drive device is variable such that the apparatus provided a variable gate delay. In such arrangements, the speed of the variable drive device can be set such that the gate portion of the apparatus blocks fluorescence (from auto-fluorophores and probe-fluorophores in a sample) for a required intervening period between the termination of the excitation state and commencement of the detection state. In another arrangement, the apparatus is adapted for providing a variable gate delay by including a variable drive device as part of the apparatus. In particular arrangements. the variable gate delay is provided by varying the speed of a variable drive device coupled to or integral with the apparatus. When the apparatus is in operation, the variable gate delay is provided by varying or selecting the width of the gate portion(s) of the apparatus for a given speed. In arrangements where the apparatus is a rotor apparatus, the variable gate delay is provided by varying or selecting the width of the gate portion(s) of the apparatus for a given rotation speed.

In operation, the apparatus may comprise one excitation state and one detection state per revolution of the apparatus about the rotation axis. The apparatus may comprise at least one gated state per revolution. The apparatus may comprise a plurality of excitation states and a plurality of detection states per revolution of the apparatus about the rotation axis. Depending on the number of first communication portions provided in the apparatus (e.g. 1 to 10 or more), the apparatus may be configurable for between 5,000 and 60,000×10=600,000 excitation cycles per second, where an excitation cycle is defined as the transition from an excitation state through a gated state to a detection state i.e. from the time when the first communication path is opened to allow light from a light source located at the illumination source location to be incident on the sample location, through to the time when the second communication path is closed such that light from the sample location is no longer incident on the detection location, and includes a gate period in the intervening period intermediate the excitation and the detection states.

The apparatus may be mounted in a housing. The housing may comprise a first and second aperture aligned with the sample and detection locations to allow light to traverse the apparatus and the housing when the apparatus is in the detection state. The housing may comprise a third aperture adapted for admitting light from a light emitting source located at the illumination light source location.

The housing may be an airtight housing. The housing may be adapted for maintaining the apparatus in an environment having a pressure less than atmospheric pressure. The internal surfaces of the housing may either be absorbing, non-reflective or absorbing and non-reflective.

With exception of a reflector located on the first communication portion, the surfaces of the apparatus may be non-reflective.

The apparatus may be used for fluorescence microscopy. The apparatus may be used for time gated fluorescence microscopy. The apparatus may be used for autosynchronous or self-synchronous time-gated fluorescence microscopy. The apparatus may be used for time gated luminescence detection.

The apparatus of the first or any one of the following aspects may be used in conjunction with an optical device for providing a time gated luminescence detection system. The optical device may be a microscope.

According to a second aspect there is provided an optical device comprising one or a plurality of focusing elements in conjunction with an apparatus according to an arrangement of the first aspect. The plurality of focusing elements may form an objective lens system. The optical device may be adapted for use in conjunction with a microscope. The optical device may be a microscope objective lens.

According to a third aspect, there is provided an autosynchronous time gated fluorescence detection method. The method may comprise providing an apparatus for autonomous synchronisation between an excitation state and a detection state, the apparatus configurable for movement between the excitation and detection states. The autonomous synchronisation apparatus may comprise a first communication portion for providing a first optical communication path between an illumination source location and a sample location. The apparatus may further comprise a second communication portion for (i) providing a second optical communication path between the sample location and the detection location, the second communication portion being operable to enable detection at the detection location of a desired optical emission from an illuminated sample which in use is located at the sample location via the second optical communication path; and (ii) concurrently preventing optical communication on the first optical communication path. The apparatus may still further comprise a gate portion for gating the first and second optical communication paths. The apparatus may be capable of being arranged to provide the first optical communication path, to gate the first and second optical communication paths and to provide the second optical communication paths in a sequential manner thereby to respectively place the apparatus in an excitation state, a gated state and a detection state. The method may further comprise providing a light source at the illumination light source location for excitation of fluorescence in a sample which in use is located at the sample location in the excitation state, the sample comprising autofluorophores having an autofluorescence lifetime and probe fluorophores having a probe fluorescent lifetime greater than the autofluorescence lifetime. A detector may be located at the detection location for detection of light from the sample location in the detection state. The apparatus may be moved with respect to the movement axis into the excitation state such that the first communication portion is adapted to enable autofluorescence and probe fluorescence to be excited in the sample by the light source. The apparatus may be then moved with respect to the movement axis to the gated state wherein the first optical communication path is gated by the gate portion such that the apparatus is an a gated state. The apparatus may be maintained in the gated state for a time at least the duration of the autofluorescence lifetime. The apparatus may be moved with respect to the movement axis into the detection state such that the probe fluorescence is permitted to be detected by the detector. Steps of the method may be optionally repeated in accordance with requirements. In use, the purpose of the gated state may be to gate for a desired period of time unwanted fluorescence in a sample excited by a light source.

According to an arrangement of the third aspect, there is provided an autosynchronous time gated fluorescence detection method comprising the steps of:

a) providing an apparatus for autonomous synchronisation between an excitation state and a detection state, the apparatus configurable for movement between the excitation and detection states and comprising:
  a1) a first communication portion for providing a first optical communication path between an illumination source location and a sample location;
  a2) a second communication portion for (i) providing a second optical communication path between the sample location and the detection location, the second communication portion being operable to enable detection at the detection location of a desired optical emission from an illuminated sample located at the sample location via the second optical communication path; and (ii) concurrently preventing optical communication on the first optical communication path;
  a3) a gate portion for gating the first and second optical communication paths;
  the apparatus being capable of being arranged to provide the first optical communication path, to gate the first and second optical communication paths and to provide the second optical communication paths in a sequential manner thereby to respectively place the apparatus in an excitation state, a gated state and a detection state;
b) providing a light source at the illumination light source location for excitation of fluorescence in a sample located at the sample location in the excitation state, the sample comprising autofluorophores having an autofluorescence lifetime and probe fluorophores having a probe fluorescent lifetime greater than the autofluorescence lifetime;
c) providing a detector located at the detection location for detection of light from the sample location in the detection state;
d) moving the apparatus with respect to the movement axis into the excitation state such that the first communication portion is adapted to enable autofluorescence and probe fluorescence to be excited in the sample by the light source;
e) moving the apparatus with respect to the movement axis to the gated state wherein the first optical communication path is gated by the gate portion;
f) maintaining the apparatus in the gated state for a time at least the duration of the autofluorescence lifetime;
g) moving the apparatus with respect to the movement axis into the detection state such that the probe fluorescence is permitted to be detected by the detector; and
h) optionally repeating steps (d) to (g) in accordance with requirements.

In use, the purpose of the gated state may be to gate for a desired period of time unwanted fluorescence in a sample excited by a light source. The apparatus may be an apparatus according to an arrangement of the first aspect.

The movement axis may be a pivot axis, the apparatus may be a rotor, the first communication portion may be one or a plurality of vanes extending radially from the pivot axis, and wherein steps (d) to (e) may be provided by rotating the rotor about the pivot axis.

According to a fourth aspect, there is provided a system for autosynchronous time gated fluorescence detection. The system may comprise an apparatus for autonomous synchronisation between an excitation state and a detection state, the apparatus configurable for movement between the excitation and detection states. The apparatus may comprise a first communication portion for providing a first optical communication path between an illumination source location and a sample location. The apparatus may further comprise a second communication portion for (i) providing a second optical communication path between the sample location and the detection location, the second communication portion being operable to enable detection at the detection location of a desired optical emission from an illuminated sample which in use is located at the sample location via the second optical communication path; and (ii) concurrently preventing optical communication on the first optical communication path. The apparatus may further comprise a gate portion for gating the first and second optical communication paths. The apparatus may be capable of being arranged to provide the first optical communication path, to gate the first and second optical communication paths and to provide the second optical communication paths in a sequential manner thereby to respectively place the apparatus in an excitation state, a gated state and a detection state. In use, the purpose of the gated state may be to gate for a desired period of time unwanted fluorescence in a sample excited by a light source.

The system may further comprise a light source at the illumination light source location for excitation of fluorescence in a sample which in use is located at the sample location in the excitation state, the sample comprising autofluorophores having an autofluorescence lifetime and probe fluorophores having a probe fluorescent lifetime greater than the autofluorescence lifetime. The system may further comprise a detector located at the detection location for detection of light from the sample location in the detection state.

The system may further comprise a mover. The mover may be adapted for moving the apparatus with respect to the movement axis into the excitation state such that the first communication portion is adapted to enable autofluorescence and probe fluorescence to be excited in the sample by the light source. The mover may further be adapted for moving the apparatus with respect to the movement axis into the gated state wherein the first optical communication path is gated by the gate portion. The mover may further be adapted for maintaining the apparatus in the gated state for a time at least the duration of the autofluorescence lifetime. The mover may further be adapted for moving the apparatus with respect to the movement axis into the detection state such that the probe fluorescence is permitted to be detected by the detector.

According to an arrangement of the fourth aspect, there is provided a system for autosynchronous time gated fluorescence detection comprising:

an apparatus for autonomous synchronisation between the excitation and detection states, the apparatus configurable for movement between an excitation and a detection state and comprising:
  a) a first communication portion for providing a first optical communication path between an illumination source location and a sample location;
  b) a second communication portion for (i) providing a second optical communication path between the sample location and the detection location, the second communication portion being operable to enable detection at the detection location of a desired optical emission from an illuminated sample which in use is located at the sample location via the second optical communication path; and (ii) concurrently preventing optical communication on the first optical communication path,
  c) a gate portion for gating the first and the second communication paths;
the apparatus being capable of being arranged to provide the first optical communication path, to gate the first and second optical communication paths and to provide the second optical communication paths in a sequential manner thereby to respectively place the apparatus in an excitation state, a gated state and a detection state;

a light source at the illumination light source location for excitation of fluorescence in a sample which in use is located at the sample location in the excitation state, the sample comprising autofluorophores having an autofluorescence lifetime and probe fluorophores having a probe fluorescent lifetime greater than the autofluorescence lifetime;

a detector located at the detection location for detection of light from the sample location in the detection state; and a mover for
  moving the apparatus with respect to the movement axis into the excitation state such that the first communication portion is adapted to enable autofluorescence and probe fluorescence to be excited in the sample by the light source;
  moving the apparatus with respect to the movement axis to the gated state wherein the first optical communication path is gated by the gate portion
  maintaining the apparatus in the gated state for a time at least the duration of the autofluorescence lifetime; and
  moving the apparatus with respect to the movement axis into the detection state such that the probe fluorescence is permitted to be detected by the detector.

According to a fifth aspect, there is provided an apparatus for providing an auto-synchronous time gated detection system. The apparatus may comprise a movement axis and movement means for moving the apparatus about the movement axis between an excitation state and an detection state, The apparatus may also comprise an excitation state director for directing light from a light emitting source to a focal location when the apparatus is in the excitation state. The apparatus may also comprise an excitation state blocker for blocking light from the focal location from being incident on a detection location when the apparatus is in the excitation state. The apparatus may also comprise detection state blocker for blocking light from the light emitting source from being incident on the focal location when the apparatus is in the detection state. The apparatus may also comprise detection state director for directing light from the focal location to the detection location when the apparatus is in the detection state. The apparatus may also comprise one or more gate portions for gating the light from the light emitting source intermediate the excitation state and the detection state. The gate portion may place the apparatus in a gated state intermediate the excitation and detection states. In use, the purpose of the gated state may be to gate for a desired period of time unwanted fluorescence in a sample excited by a light source.

In an arrangement of the fifth aspect, there is provided an apparatus for providing an auto-synchronous time gated detection system comprising: a movement axis; movement means for moving the apparatus about the movement axis between an excitation state and an detection state; excitation state directing means for directing light from a light emitting source to a focal location when the apparatus is in the excitation state; excitation state blocking means for blocking light from the focal location from being incident on a detection location when the apparatus is in the excitation state; detection state blocking means for blocking light from the light emitting source from being incident on the focal location when the apparatus is in the detection state; detection state directing means for directing light from the focal location to the detection location when the apparatus is in the detection state; and at least one gate portion for gating the light from the light emitting source intermediate the excitation state and the detection. In use, the purpose of the gated state may be to gate for a desired period of time unwanted fluorescence in a sample excited by a light source.

The movement means may be configurable for: moving the apparatus to the excitation state for exciting photoluminescence in a sample which in use is located at the focal location, the photoluminescence having first and second photoluminescence lifetimes; maintaining the apparatus in the excitation state for a first period of time at least the duration of the first photoluminescence lifetime; and moving the apparatus to the detection state at a time after the first luminescence is lifetime.

The movement axis may be a pivot axis and the apparatus may comprise: at least one or a plurality of vane(s) extending radially from the pivot axis and a respective void space adjacent the or each vane(s). The movement about the pivot axis may be such that: in the excitation state the excitation state directing means is aligned with the light emitting source to direct light therefrom to the focal location; and in the detection state the excitation state directing means is misaligned with the light emitting source.

The excitation state directing means may be a reflector on the distal end(s) of the or each vane(s). The excitation state blocking means may be the or each vane(s). The detection state blocking means may be provided by misalignment of the reflector when the apparatus is in the detection state. The detection state directing means may be the void space adjacent the or each vane(s).

The pivot axis may be a rotation axis and the apparatus may rotate about the rotation axis. The apparatus may rotate continuously about the rotation axis.

According to a sixth aspect, there is provided an apparatus for deflecting light comprising: a pivot axis, the apparatus being adapted for movement about the pivot axis to define an area; at least one optical path passing through the area; at least one gate portion for gating optical path; and at least one reflective surface for deflection of light from an external light emitting source.

The reflective surface may be distal the pivot axis. The apparatus may further comprise an upper surface and a lower surface, the upper surface having a greater radial extent from the pivot axis then the lower surface, wherein the reflective surface comprises a distal surface of the apparatus contiguous with both the upper and lower surfaces and the radial extent of the apparatus.

Movement of the apparatus about the pivot axis may cause the optical path to alternate between an open and a closed configuration. The reflective surface may be adapted for deflection of light from the light emitting source when the optical path is in the closed configuration.

The reflective surface may further be adapted for deflection of light from the light emitting source to a sample, the sample comprising at least one autofluorophore responsive to light from the light source such that it emits fluorescence with an autofluorescence lifetime.

The apparatus may be adapted such that the optical path is in the closed position to substantially block autofluorescence from an excited autofluorophore for a duration of time being at least the autofluorescence lifetime. The gate portion may be adapted to place the optical path in the closed position such that the apparatus is in a gated state. In use, the purpose of the gated state may be to gate for a desired period of time unwanted fluorescence in a sample excited by a light source.

The sample may further comprise at least one probe fluorophore responsive to light from the light source such that it emits probe fluorescence with an probe fluorescence lifetime longer than the autofluorescence lifetime, and the apparatus may be further adapted such that the optical path is able to be configured in the open position after a time longer than the autofluorescence lifetime thereby to substantially allow fluorescence from an excited probe fluorophore to traverse the optical path.

The optical path may comprise an optical detector located therein to detect light from the sample traversing the optical path.

According to a seventh aspect, there is provided an autosynchronous time gated luminescence detection system having excitation and detection states, the system comprising:
    an apparatus for passive synchronisation between the excitation and detection states, the apparatus comprising: a pivot axis, the apparatus adapted for movement about the pivot axis to define an area; at least one optical path passing through the area wherein movement of the apparatus about the pivot axis causes the optical path to alternate between an open and a closed configuration; at least one gate portion for gating the optical path; and at least one reflective surface distal to the pivot axis for deflection of light;
    a light emitting source adaptable for emitting light to be reflected by the reflective surface and
    a detector located in the optical path for detection of light traversing the optical path.

In the excitation state, the apparatus may be configurable for deflection of light from the light emitting source to a sample location, thereby to excite fluorescence in the autofluorophores and the probe fluorophores, and the optical path may be configurable such that it is in the closed position for a time at least the duration of the autofluorescence lifetime;

In the detection state, the apparatus may be configurable such that light from the light emitting source is not deflected to the sample, and the optical path is in the open position for detection of light traversing the optical path.

The gate portion may be configurable for gating the optical path intermediate the excitation and the detection states. The gate portion may place the apparatus in a gated state intermediate the excitation and detection states. In use, the purpose of the gated state may be to gate for a desired period of time unwanted fluorescence in a sample excited by a light source.

The light emitting source may be adapted for exciting fluorescence in a sample comprising autofluorophores and probe fluorophores, the autofluorophores having an autofluorescence lifetime and the probe fluorophores having a probe fluorescence lifetime, the probe fluorescence lifetime being greater than the autofluorescence lifetime.

During the detection state, the apparatus may be configured such that the light traversing the optical path is substantially fluorescence from an excited probe fluorophore.

According to an eighth aspect, there is provided an apparatus configurable for movement between an excitation and a detection state for use in a time gated luminescence detection system. The apparatus may comprise a first communication portion for providing a first optical communication path operable when the apparatus is in the excitation state and a second communication portion for providing a second optical communication path operable when the apparatus is in the detection state. The apparatus may also comprise at least one gate portion for gating the first and the second communication paths. The gating of the first and the second communication paths may be intermediate the excitation and the detection states. The gate portion may place the apparatus in a gated state intermediate the excitation and detection states. In the excitation state, the first communication portion may facilitate optical communication on the first optical communication path between a illumination light source location and a sample location whilst concurrently preventing optical communication between the sample location and a detection location. In the detection state, the second communication portion may facilitate optical communication on the second optical communication path between the sample and the detection locations whilst concurrently preventing optical communication between the illumination light source and the sample locations. In use, the purpose of the gated state may be to gate for a desired period of time unwanted fluorescence in a sample excited by a light source.

In an arrangement of the eighth aspect there is provided an apparatus configurable for movement between an excitation and a detection state for use in a time gated luminescence detection system, the apparatus comprising: a first communication portion for providing a first optical communication path operable when the apparatus is in the excitation state, a second communication portion for providing a second optical communication path operable when the apparatus is in the detection state such that in the excitation state and at least one gate portion for gating the first and the second communication paths intermediate the excitation and the detection states, the first communication portion facilitates optical communication on the first optical communication path between a illumination light source location and a sample location whilst concurrently preventing optical communication between the sample location and a detection location; and in the detection state, the second communication portion facilitates optical communication on the second optical communication path between the sample and the detection locations whilst concurrently preventing optical communication between the illumination light source and the sample locations.

According to a ninth aspect, there is provided an apparatus for providing an auto-synchronous time gated luminescence detection system. The apparatus may be configurable for movement between a first position and a second position wherein, in the first position the apparatus is in an excitation state and in the second position the apparatus is in a detection state. The apparatus may comprise a first optical communication means operable when the apparatus is in the first position for facilitating optical communication between a first and a sample location, the first communication means being adapted for allowing light from the illumination light source location to impinge on the sample location whilst concurrently preventing optical communication between the sample location and a detection location. The apparatus may further comprise a second optical communication means operable when the apparatus is in the second position for facilitating optical communication between the sample and the detection locations, the second means being adapted for allowing light from the sample location to impinge on the detection location whilst concurrently preventing optical communication between the illumination light source and the sample locations. The apparatus may also comprise at least one gate portion for gating the excitation and the detection states. The gating may be intermediate the excitation and the detection states such that the excitation state, a gated state and the detection state are provided in a sequential manner. In use, the purpose of the gated state may be to gate for a desired period of time unwanted fluorescence in a sample excited by a light source.

The location and or position of the first and second communication means may be fixed relative each other during movement of the apparatus such that, in use, repeated movement of the apparatus between the first and second positions provides autonomous synchronisation between the emission and detection states. The gate portion may be fixed relative to either or both the first and second communication means.

In an arrangement of the ninth aspect, there is provided an apparatus for providing an auto-synchronous time gated luminescence detection system, the apparatus being configurable for movement between a first position and a second position wherein, in the first position the apparatus is in an excitation state and in the second position the apparatus is in a detection state, the apparatus comprising first optical communication means operable when the apparatus is in the first position for facilitating optical communication between a first and a second location, the first communication means being adapted for allowing light from the first location to impinge on the second location whilst concurrently preventing optical communication between the second location and a third location;

second optical communication means operable when the apparatus is in the second position for facilitating optical communication between the second and the third locations, the second means being adapted for allowing light from the second location to impinge on the third location whilst concurrently preventing optical communication between the first and the second locations; and at least one gate portion for gating the excitation and the detection states, and wherein the location of the first and second communication means are fixed relative each other during movement of the apparatus such that, in use, repeated movement of the apparatus between the first and second positions provides autonomous synchronisation between the excitation and detection states and provides the excitation state, a gated state, and the detection state in a sequential manner. The gate portion may be fixed relative to either or both the first and second communication means. The first location may be an illumination source location, the second location may be a sample location, and the third location may be a detection location, and vice versa. The apparatus may comprise at least one gate portion configurable for preventing optical communication between the second location and a third location. The gate portion may gate optical communication between the second location and a third location. In use, the purpose of the gated state may be to gate for a desired period of time unwanted fluorescence in a sample excited by a light source.

According to a tenth aspect, there is provided a system for autosynchronous time gated fluorescence detection comprising:

an apparatus for autonomous synchronisation between an excitation state and a detection state, the apparatus configurable for movement between the excitation and detection states and comprising:
  a) a first communication portion for providing a first optical communication path between an illumination source location and a sample location;
  b) a second communication portion for (i) providing a second optical communication path between the sample location and the detection location, the second communication portion being operable to enable detection at the detection location of a desired optical emission from an illuminated sample which in use is located at the sample location via the second optical communication path; and (ii) concurrently preventing optical communication on the first optical communication path; and
  c) a gate portion for gating the first and second optical communication paths;

the apparatus being capable of being arranged to provide the first optical communication path, to gate the first and second optical communication paths and to provide the second optical communication paths in a sequential manner thereby to respectively place the apparatus in an excitation state, a gated state and a detection state;

a light source at the illumination source location for excitation of fluorescence in a sample which in use is located at the sample location in the excitation state, the sample comprising autofluorophores having an autofluorescence lifetime and probe fluorophores having a probe fluorescent lifetime greater than the autofluorescence lifetime;

a detector located at the detection location for detection of light from the sample location in the detection state; and a mover for moving the apparatus with respect to the movement axis into the excitation state such that the first communication portion is adapted to enable autofluorescence and probe fluorescence to be excited in the sample by the light source;

moving the apparatus with respect to the movement axis to the gated state wherein the first optical communication path is gated by the gate portion maintaining the apparatus in the gated state for a time at least the duration of the autofluorescence lifetime; and moving the apparatus with respect to the movement axis into the detection state such that the probe fluorescence is permitted to be detected by the detector.

The gate portion may gate the first and the second optical communication paths. In use, the purpose of the gated state may be to gate for a desired period of time unwanted fluorescence in a sample excited by a light source.

According to an eleventh aspect, there is provided an autosynchronous time gated fluorescence detection method. The method may comprise providing autonomous synchronisation between an excitation state and a detection state. The autonomous synchronisation may comprise providing a first optical communication path between an illumination source location and a sample location. The autonomous synchronisation may further comprise (i) providing a second optical communication path between the sample location and the detection location to enable detection at the detection location of a desired optical emission from an illuminated sample which in use is located at the sample location via the second optical communication path; and (ii) concurrently preventing optical communication on the first optical communication path. The method may further comprise providing a gate for gating the first and second optical communication paths. The autonomous synchronisation may be provided by: providing the first optical communication path, gating the first and second optical communication paths and to provide the second optical communication paths in a sequential manner thereby to respectively provide an excitation state, a gated state and a detection state. The method may further comprise providing a light source at the illumination light source location for excitation of fluorescence in a sample which in use is located at the sample location in the excitation state, the sample comprising autofluorophores having an autofluorescence lifetime and probe fluorophores having a probe fluorescent lifetime greater than the autofluorescence lifetime. A detector may be provided at the detection location for detection of light from the sample location in the detection state. The first communication portion may be enabled to enable autofluorescence and probe fluorescence to be excited in the sample by the light source. The gated state may then be enabled to provide the gated state. The gated state may be maintained for a time at least the duration of the autofluorescence lifetime. The detection state may be enabled such that the probe fluorescence is permitted to be detected by the detector. Steps of the method may be optionally repeated in accordance with requirements. In use, the purpose of the gated state may be to gate for a desired period of time unwanted fluorescence in a sample excited by a light source.

According to an arrangement of the eleventh aspect, there is provided an autosynchronous time gated fluorescence detection method comprising the steps of:

a) providing autonomous synchronisation between an excitation state and a detection state comprising:

a1) providing a first communication portion for providing a first optical communication path between an illumination source location and a sample location;

a2) (i) providing a second optical communication path between the sample location and the detection location, the second communication portion to enable detection at the detection location of a desired optical emission from an illuminated sample located at the sample location via the second optical communication path; and (ii) concurrently preventing optical communication on the first optical communication path;

a3) providing a gate portion for gating the first and second optical communication paths;

wherein the autonomous synchronisation is provided by: providing the first optical communication path, gating the first and second optical communication paths and to provide the second optical communication paths in a sequential manner thereby to respectively provide an excitation state, a gated state and a detection state;

b) providing a light source at the illumination light source location for excitation of fluorescence in a sample located at the sample location in the excitation state, the sample comprising autofluorophores having an autofluorescence lifetime and probe fluorophores having a probe fluorescent lifetime greater than the autofluorescence lifetime;

c) providing a detector located at the detection location for detection of light from the sample location in the detection state;

d) enabling the first optical communication path to enable autofluorescence and probe fluorescence to be excited in the sample by the light source;

e) enabling the gated state wherein the first optical communication path is gated by the gate portion;

f) maintaining the gated state for a time at least the duration of the autofluorescence lifetime;

g) enabling the detection state such that the probe fluorescence is permitted to be detected by the detector; and h) optionally repeating steps (d) to (g) in accordance with requirements.

In other aspects, features of the preceding aspects and/or features disclosed in the accompanying drawings may be combined in any combination for provision of an autosynchronous time-gated luminescence detection system, or for provision of an apparatus for converting a time-gated luminescence detection system to an autosynchronous time-gated luminescence detection system as would be appreciated by the skilled addressee.

Certain aspects and/or arrangements described herein may provide a low-cost time-gated luminescence apparatus, method and/or system, that may be used in a microscope system, or a method of TGL using a microscope system.

BRIEF DESCRIPTION OF THE DRAWINGS

Arrangements of the apparatus will now be described, by way of an example only, with reference to the accompanying drawings wherein:

FIGS. 2A and 2B show a schematic description of the excitation and detection states of a prior art dual-chopper TGL detection system;

FIGS. 4A to 4C respectively show the emission, transition (gated) and excitation states of the rotor apparatus for use in an auto-synchronous time-gated luminescent detection system;

DETAILED DESCRIPTION OF THE PREFERRED EMBODIMENTS

Figure 1A:
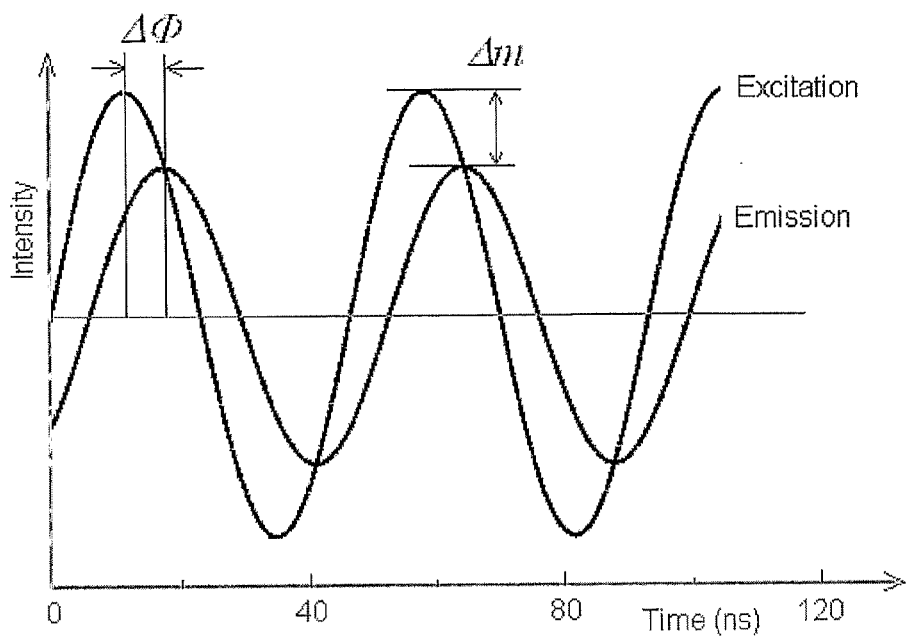
FIG. 1A is a graph depicting a time-resolved fluorescence detection system.
Figure 1B:
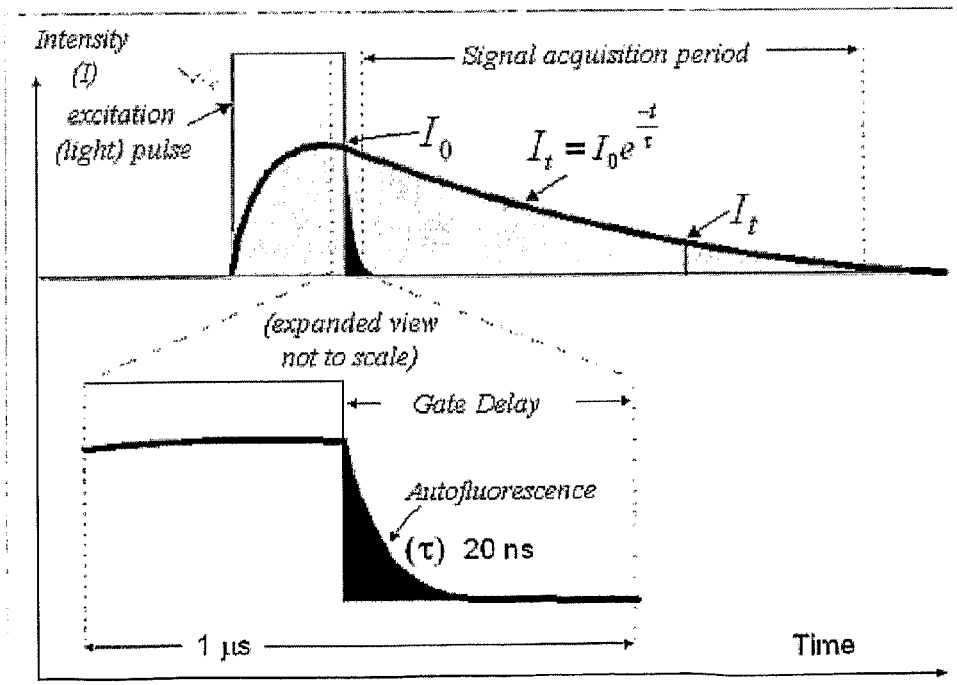
FIG. 1B is a graph depicting a time-gated fluorescence detection system.
Figure 3A:
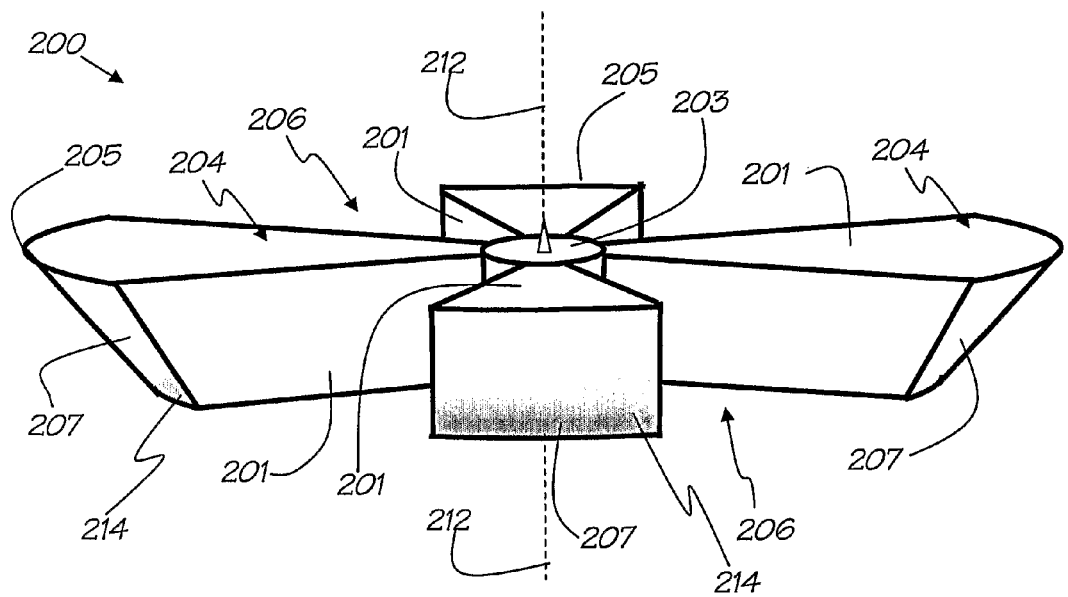
FIGS. 3A and 3B show a schematic depiction of an apparatus according to the invention depicted as a rotor apparatus for use in a TGL detection system for auto-synchronisation of excitation and emission (detection) states of the TGL detection system.

Referring to FIG. 3A, there is provided an arrangement 200 of an apparatus for use in a time gated luminescence detection system. The apparatus 200 comprises a) a first communication portion 204 for providing a first optical communication path between an illumination source location and a sample location;

b) a second communication portion 206 for (i) providing a second optical communication path between the sample location and the detection location, the second communication portion being operable to enable detection at the detection location of a desired optical emission from an illuminated sample which in use is located at the sample location via the second optical communication path; and (ii) concurrently preventing optical communication on the first optical communication path; and c) a gate portion 214 for gating the first and second optical communication paths;

the apparatus 200 being capable of being arranged to provide the first optical communication path, to gate the first and second optical communication paths and to provide the second optical communication paths in a sequential manner thereby to respectively place apparatus 200 in an excitation state, a gated state and a detection state.

In this arrangement the second communication portions 206 of the apparatus are the void space regions defined by the area adjacent first communication portions 204.

The apparatus depicted in FIG. 3A is particularly suited to the use of a pulsed or quasi-continuous-wave excitation source for exciting fluorescence in a sample at the sample location. In particular, the excitation light source is configured such that the pulse width of each excitation pulse is shorter than the time that the reflector is aligned between the illumination source location and the sample location. Additionally, the pulse is synchronised with the rotor such that each pulse is timed to be incident on a reflector such that is it reflected onto the sample to excite the probe fluorophores and the autofluorophores present in the sample. Preferably the pulse is timed to strike the leading edge portion of the vane (with respect to the direction of rotation of the rotor) such that a portion of the reflector near the trailing edge is not illuminated. The portion of the reflector that is not illuminated then forms the gate portion 214 of the apparatus for gating the excitation and the detection states. The gate portion 214 (i.e. the portion of the reflector not illuminated by the excitation source) is configured such that the gate delay time is sufficient for blocking a substantial portion of any autofluorescence from excited autofluorophores in an excited sample at the sample location from being detected by a detector at the detector location. The gate portion may be configured in conjunction with the speed with which the apparatus 200 is moved between the excitation and the detection states. The substantial portion of the autofluorescence blocked by the gate portion may be, for example, more than 80%; 85%; 90%; 95%; 97%; 98%; or more than 99% of the autofluorescence.

For example the gate delay time may be configured such that it is at least a long as the fluorescence lifetime of any autofluorophores present in the sample. A variable gate delay with a pulsed or quasi-continuous-wave excitation source may be provided by varying the timing of the synchronisation between the light pulse and the position of the reflector such that the portion of the reflector trailing edge that is not illuminated may be increased or decreased as required to give a corresponding increase of decrease in the gate delay time. This synchronisation method of varying the gate delay may be used in conjunction with variation in the movement or rotation speed of the apparatus to provide greater flexibility in the available variation in the gate delay time. Further arrangements of the apparatus are suitable for use with a continuous wave excitation light source as described below with reference to alternate arrangements.

The apparatus 200 is depicted in the present arrangement as a rotor apparatus for use in a TGL detection system. The rotor apparatus 200 depicted comprises a first communication portion 204 depicted as one or a plurality of vanes or arms 201 (in this arrangement, four vanes are depicted, which are typically identical but may differ in a particular configurations of the invention. For example, different surface coatings could be employed on alternate/adjacent or otherwise selected reflective rotor faces to preferentially reflect selected wavelengths with greater intensity, thereby providing an excitation source with the facility to excite two different luminophores at different times. This feature could prove useful for the multiplexed detection of different labels. The vanes extend radially from a central hub 203 having a movement axis 212 (in this arrangement the movement axis is a rotation axis at the centre of the rotor apparatus 200). The distal end 205 of each vane 201 is provided with a reflector 207 which is a highly reflective surface. At least a portion of the reflector comprises the gate portion 214. The gate portion is at least a portion of the reflector 207 at the trailing edge of the reflector with respect to the direction of movement of the apparatus when in operation. In some arrangements, a portion of the leading edge of the reflector 207 may also comprise a gate portion. The second communication portion 206 of the present arrangement is depicted in as the void space defined by and intermediate each of the vanes 201 of the first communication portion 204. In other arrangements (not shown) the second communication may comprise a transparent portion in the space intermediate each of the vanes 201, and may for example comprise a transparent glass or plastics (e.g. perspex) material which is contiguous with adjacent vanes.

In an arrangement, the second communication portion may be a void space in the apparatus which is defined by the first communication portion. The second optical communication path may comprise the void space such that light propagating on the second optical communication path may propagate though the void space. In an alternate arrangement, the second communication portion may comprise a transparent portion. The second optical communication path may comprises the transparent portion such that light propagating on the second optical communication path may propagate though the transparent portion.

The apparatus may be formed from any suitable material including, but not limited to a metal, a plastic, ceramic, non-metal, or equivalent material). The reflectors 207 may be coated with an evaporated or sputtered metal coating, or vacuum metallisation or other technique to provide a highly specular finish on reflector 207 thereby to enable highly efficient reflection of the excitation light 231 onto the sample 235.

Figure 3B:
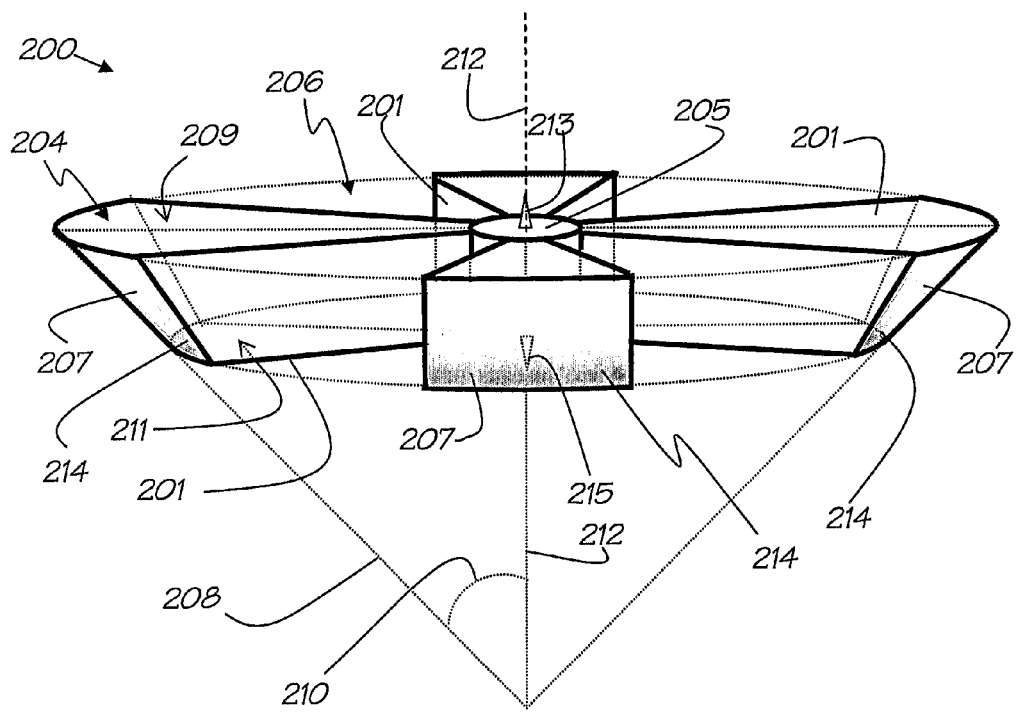

In the present arrangement of the rotor apparatus 200 as depicted in FIG. 3B, each of the reflectors 207 are formed such that it lies on a surface section of the cone 208 defined by the upper and lower surfaces (209 and 211 respectively) of the rotor 200. In preferred arrangements, the upper and lower surfaces 209 and 211 are parallel to each other. In the arrangement depicted in FIGS. 3A and 3B, the cone 208 is a 45 degree cone where the angle 210 between the surface of the cone and the central axis 212 of the rotor is 45 degrees. Thus, in the present arrangement, the reflectors 207 are at a 45 degree angle to the central axis 212 of the rotor 200, although it will be appreciated by the skilled addressee that the surfaces may be at a different angle to the central axis 212 with appropriate modifications to the location of the excitation source as is described in the arrangements below.

Each reflector 207 is preferably a highly reflective surface for high efficiency specular reflection therefrom of light at either: a particular desired wavelength for excitation of a particular luminescent probe with an absorption feature at the desired wavelength; light of a plurality (two, three, four, five or more) particular wavelengths for excitation of a corresponding plurality of luminescent probes with known absorption features at the plurality of particular wavelengths; or a broadband range of wavelengths for either excitation of one or more luminescent probes with either known or unknown absorption features. A reflector 207 that is highly reflective over a broad wavelength range covering at least that of a number of known efficient luminescent probes also has the advantage that the rotor apparatus may be readily adapted to excitation of different luminescent probes simply by interchanging the excitation source to provide excitation light at the required wavelength. In typical arrangements, the reflector 207 is highly reflective surface reflective for optical wavelengths in the range of 150 nm to 2000 nm. In other arrangements, the reflector may be highly reflective for optical wavelengths in the range of 150 nm to 400 nm, 300 nm to 1000 nm, 800 nm to 2000 nm, 150 nm to 800 nm or other suitable range for reflecting light from an external light emitting source (not shown). Alternatively an excitation source with a broad emission spectrum (e.g. a white light source) or multiple emission wavelengths may be coupled to the rotor apparatus for excitation of more than one or a plurality of fluorescent probes in the sample. This technique would then provide the additional advantage of multiplexed detection of the plurality of fluorescent probes using a single excitation source. The reflectivity of each of the reflectors 207 at the particular wavelength(s) of interest is typically in the range of 90% to 99.9999%, and more typically in the range of 99% to 99.999%. In other arrangements, the reflector may be a diffusing or scattering surface which scatters light incident on the reflector toward the sample location. The scattered light may be diffuse light.

The rotor apparatus 200 also comprises respective upper and lower mounting formations 213 and 215 for mounting the rotor in a housing. The mounting formations are located on the central axis 212 of the central hub 203 and in use the rotor rotates about the central axis 212 in accordance with requirements as described below. In the present arrangements, the mounting formations 213 & 215 are depicted respectively as upwardly and downwardly extending projections, which may allow for accommodation within for example, a jeweled (sapphire) V-cup assembly (not shown) to minimize friction during operation, however, there are many available functionally equivalent variations for such mounting formations which would be appreciated by the skilled addressee, for example a high-speed bearing support mounting arrangement may be suitable in particular arrangements.

In use, the principle of operation of the rotor apparatus 200 in a TGL detection systems is described with reference to FIGS. 4A and 4B. The rotor is set into motion via a suitable drive is device or mover at rotation speed in the range of about 5,000 to 60,000 revolutions per minute (rpm) (depicted as a clockwise rotation in the direction of arrow 202). This range is suitable for excitation of luminescent probes including lanthanide chelates (among others including for example phosphorescent probes based on platinum and palladium coproporphyrins) which generally have long luminescent lifetimes in the range of about 70 μs to over 9 ms (depending on environment). For the particular arrangement of the rotor apparatus 200 with four radially extending vanes 201, a rotation speed of about 6,000 rpm corresponds to an excitation frequency of about 400 Hz. It will be appreciated that the excitation frequency will vary accordingly with variations in the rotation speed, and the number of vanes 201 included in the rotor apparatus. In other arrangements, the rotation speed of the rotor may be either increased to at least 15,000 or 60,000 rpm or more, or reduced to at least 1,000 or 1,000 rpm in accordance with requirements. Rotation speeds of up to 60,000 rpm or up to 80,000 rpm allow for detection of fluorescence lifetimes less than 100 microseconds as may be desirable for use with particular luminescent probes.

At any moment in time, the rotor apparatus 200 when in motion with respect to the rotation axis 212 can be considered to be in one of three possible states; an excitation state (FIG. 4A), a gated (transition) state (FIG. 4B) between excitation and detection states, and an emission/detection state (FIG. 4C). These three states are respectively depicted schematically in FIGS. 4A to 4C where the rotor 200 is shown rotating in a clockwise direction 202 with reference to a sample 220. The sample 200 in this case may equivalently depict a window or aperture 203 which defines a viewable area of a sample, or may be the viewable area itself of the sample with respect to an external imaging system (not shown). Briefly, during the excitation state of FIG. 4A, the rotor 200 is positioned such that the light from a suitable excitation light source (not shown) is incident on the reflector 207 of the rotor vane 201 and is deflected to the sample 220 to excite fluorescence in labelled probes and auto-fluorophores in the sample. In this position, any fluorescence emitted from the sample 202 is blocked by the rotor vane 201 from which the excitation light is reflected from. To achieve this, the width of the rotor vane 201 may be at least equal to or greater than the width of the window/aperture 203. During the gated/transition state of FIG. 4C, the light from the excitation source is partially incident on the reflector 207 of the rotor vane 201. The portion of light which is still incident on the reflector 207 is reflected onto the sample and a portion of the fluorescence from the sample is able to be transmitted between adjacent vanes to an observer (not shown) for detection. During the emission/detection state of FIG. 4C, the rotor is positioned such that no excitation light is incident on any of the reflective surfaces of the rotor 200 and the luminescence (phosphorescence) from the sample 220 passes between adjacent rotor vanes to be detected by the observer. To achieve this, the distance between adjacent vanes 201 of the rotor may be equal to or greater than the diameter of the window/aperture 203. These three states are outlined in further detail below with reference to an example prototype rotor apparatus.

Operation of an exemplary arrangement of an apparatus for is described below with reference to FIGS. 5A and 5B. The rotor apparatus 200 is configurable for movement with respect to the movement axis 212 between an excitation (FIG. 5A) and a detection state (FIG. 5B) and for example may be connected to a drive device or mover (not shown) such as a motor (e.g. an electric motor or magnetic drive system) to facilitate movement between the excitation and detection states.

The apparatus 200 comprises a plurality of first communication portions 204 each adapted for providing a corresponding plurality of first optical communication paths 232 between an illumination source location 242 and a sample location 244. The apparatus 200 also comprises gate portion(s) 214 (one or more) which gates optical communication between the sample location 244 and a detection location 246. The gating is provided by the gate portion(s) by prevention of optical communication on the second optical communication path in the intervening period between termination of the excitation state and commencement of the detection state. The gating of the optical communication may be provided for a desired gate time period. The gate portion 214 may be provided on the first communication portion 204, and may be provided at least on the trailing edge 216 of the first communication portion 204. The apparatus also comprises a second communication portion 206 adapted for providing a second optical communication path 234 between the sample location 244 and the detection location 236, the second communication portion being operable to enable detection at the detection location of a desired optical emission from an illuminated sample which in use is located at the sample location via the second optical communication path. The second communication portion 206 also prevents optical communication on the first optical communication path 232 (not shown). The apparatus 200 is capable of being arranged to provide the first and second optical communication paths in a sequential manner thereby to respectively place the apparatus in an excitation state, a gated state and a detection state. The arrangement of the apparatus to provide the first and second optical communication paths in a sequential manner may comprise moving the apparatus with respect to an axis. The gate time period may be configured as a function of the size of the first communication portion and the speed of movement of the first communication portion. The axis may be a translation, pivot or a rotation axis.

Light 231 from an external light emitting source 230 located at the illumination light source location 242 is provided at the desired wavelength and/or wavelengths for excitation of a desired luminescent probe. During the excitation state as depicted in FIG. 5A, the first communication portion 204 is aligned with both the illumination light source location 242 and the sample location 244 to provide the first optical communication path 232. The excitation light 231 is thus incident on a reflector 207 of the rotor 200 and is reflected along first optical communication path 232 toward a sample holder 233 located at the sample location 244. In use, the sample holder contains a sample 235 under test. The sample 235 generally comprises autofluorophores which, when excited by a suitable light source, emit autofluorescence 236 with a short-lived autofluorescence lifetime. During the excitation state, the autofluorescence 236 emitted from the autofluorophores in sample 235 due to excitation from light 231 is blocked by vane 201 of the rotor. The autofluorescence is thus prevented from traversing the second optical communication path 234 and therefore is not detected by observer 240 (which may also be a suitable observer or detector 240 located at the detection location 246. Detector 240 may be any suitable electronic detector (e.g. charge coupled device (CCD), image intensified CCD), or other suitable detector including photodiodes or avalanche photodiodes for detection of the luminescence. Detector 240 may be coupled to a control module (not shown) for recording and analysing signals from the detector 240. The control module may be coupled via a communication line, wireless or optical coupling (which may be a bi-directional communication line or coupling), for example to detector 240. Alternatively, detector 240 may be coupled to a computer and/or storage means (not shown) for recording and/or analysing signals/images of the detected fluorescence as well as being or instead of being coupled to the control module.

In the present arrangement of the apparatus 200, the second communication portion 206 is depicted as void spaces in the apparatus which are defined by the first communication portions 204 (in this case, the void spaces are defined by adjacent vanes 201). The second optical communication path 236 comprises the void space such that light propagating on the second optical communication path 234 propagates though the void space.

The sample 235 further comprises molecules which have been labelled with the luminescent probe which when excited by light 231 emit a long-lived fluorescence signal 237 having a fluorescence lifetime longer than the autofluorescence lifetime of the autofluorophores. Whilst the rotor apparatus 200 is in the excitation state depicted in FIG. 5A, the fluorescence 237 is also blocked by the vane 201 of the first communication portion 204 such that the first communication portion prevents optical communication between the sample location 244 and the detection location 246 and is not detected by observer 240.

Figure 5A:
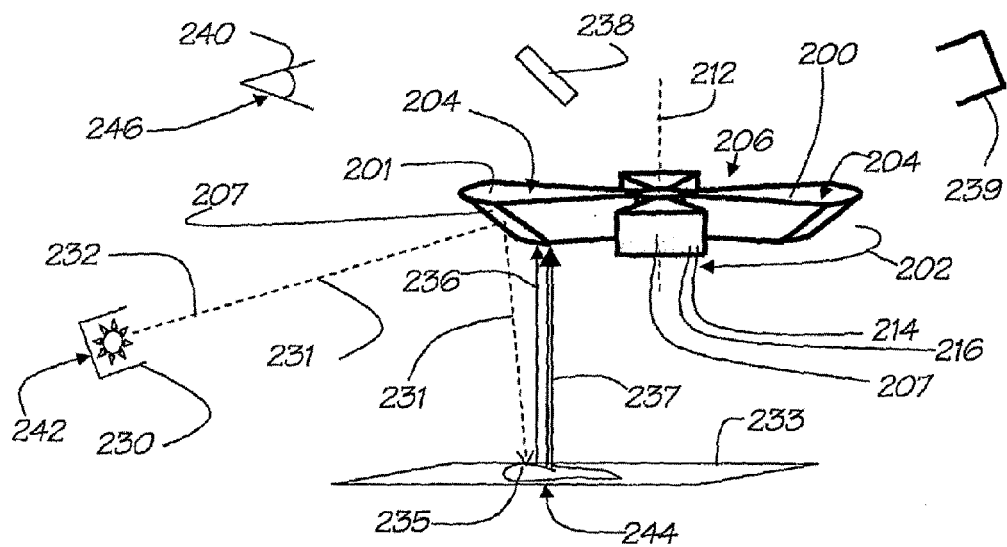
FIGS. 5A and 5B respectively show the excitation and detection states of an arrangement of the present auto-synchronous time-gated luminescent detection system.
Figure 5B:
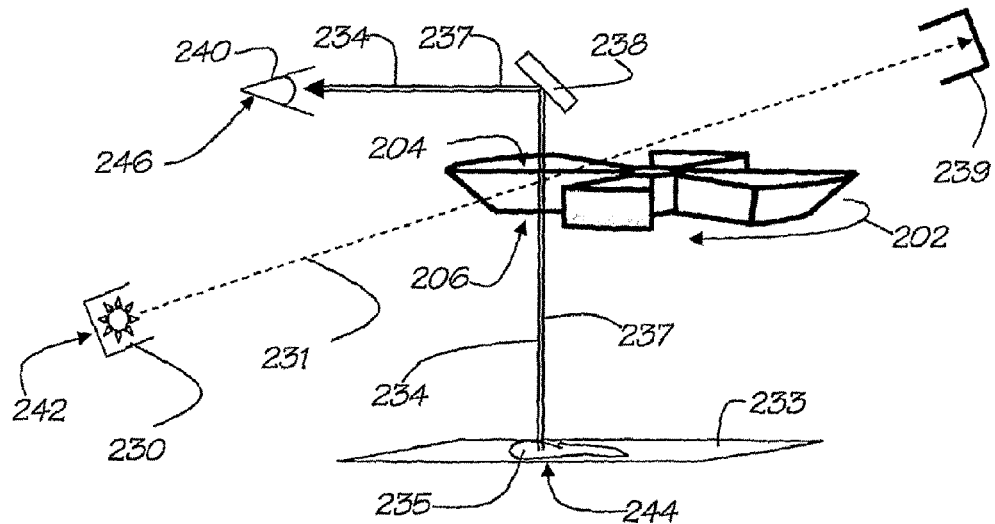

As the rotor apparatus 200 is moved to the detection state (as depicted in FIG. 5B) by the mover, the second communication portion 206 is aligned with the illumination light source location such that the rotor vane 201 is positioned out of the first optical communication path 232. The excitation light 231 from the light emitting source is thus prevented from traversing the first optical communication path to the sample location 244 (by virtue of the reflector 207 on vane 201 not being aligned with the light source) and is captured by a beam dump 239. With the removal of the excitation light from being incident on the sample, the intensity of the autofluorescence quickly falls due to the short autofluorescence lifetime of the autofluorophores.

The arrangement depicted in FIG. 5A shows the emission light propagating in plane that is non-coplanar with the rotation plane of the rotor. This enables the positioning of a suitable beam dump 239 for capture of the unwanted excitation light (which in the presently described arrangement is generated by a continuous wave excitation light source) during the detection state. Thus, in this arrangement, the reflectors 207 of the rotor are at an angle greater than 45 degrees with respect to the rotation axis 212 of the rotor apparatus 200. In other arrangements, the faces may be placed at a 45 degree angle with the central rotation axis 212, and the excitation light source 230 may be positioned co-planar with the rotation plane of the rotor such that during the detection state, light 231 from the light source is incident on a non-reflective or absorbing portion of the rotor apparatus 200. This arrangement is described further below.

Also, in the detection state, the rotor vane 201 has moved out of the second optical communication path 234 of the fluorescence signal, and thus the fluorescence 237 from fluorophores (e.g. molecules that have been labelled with a luminescent probe) in the sample 235 is able to propagate alone the second optical communication path 234 to the observer 240 (via an optional turning reflector 238) where the desired fluorescence signal 237 is detected.

As the rotor apparatus 200 continues to rotate, the excitation-detection cycle is repeated at the excitation frequency as determined by the rotation speed of the rotor and the number of vanes 201 included in the rotor apparatus. Table 1 shows indicative values of the excitation frequency for a range of rotation speeds and for 4, 6 or 8 rotor arms.

TABLE 1

| Rotor Speed (rpm) | No. Rotor Arms | Excitation Freq (Hz) |
| --- | --- | --- |
| 5,000 | 4 | 333.3 |
| 10,000 | 4 | 666.7 |
| 15,000 | 4 | 1,000.0 |
| 20,000 | 4 | 1,333.3 |
| 30,000 | 4 | 2,000.0 |
| 40,000 | 4 | 2,666.7 |
| 50,000 | 4 | 3,333.3 |
| 60,000 | 4 | 4,000.0 |
| 5,000 | 6 | 500.0 |
| 10,000 | 6 | 1,000.0 |
| 15,000 | 6 | 1,500.0 |
| 20,000 | 6 | 2,000.0 |
| 30,000 | 6 | 3,000.0 |
| 40,000 | 6 | 4,000.0 |
| 50,000 | 6 | 5,000.0 |
| 60,000 | 6 | 6,000 |
| 5,000 | 8 | 666.7 |
| 10,000 | 8 | 1,333.3 |
| 15,000 | 8 | 2,000.0 |
| 20,000 | 8 | 2,666.7 |
| 30,000 | 8 | 4,000.0 |
| 40,000 | 8 | 5,333.3 |
| 50,000 | 8 | 6,666.7 |
| 60,000 | 8 | 8,000 |

Figure 6:
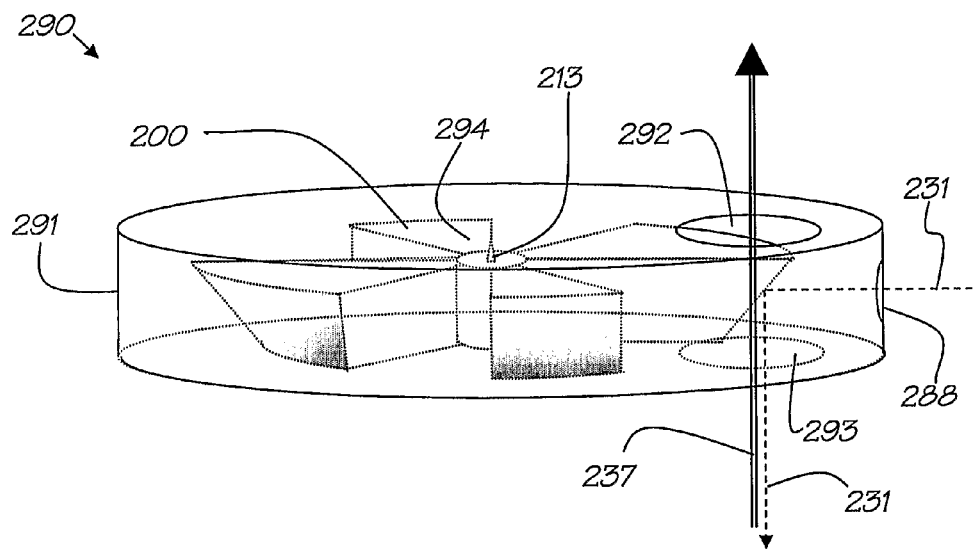
FIG. 6 shows a further arrangement of a rotor apparatus.

In an arrangement 290 of the rotor apparatus as depicted in FIG. 6, the rotor 200 may be enclosed within a housing 291. The housing 261 is generally opaque and comprises upper and lower windows (292 and 293 respectively) to allow the fluorescence signal 237 from the sample (not shown) to propagate along the second optical communication path and pass between the rotor vanes 201 during the emission/detection state. The housing also comprises an excitation window 288 to allow the excitation light from the external excitation light source (not shown) to enter the housing to be reflected by the reflectors 207 through the lower window 265 towards the sample (not shown) along the first optical communication path.

One particular advantage of a rotor apparatus enclosed within a housing is that the housing can be fabricated to be (at least) airtight such that the reflectors 207 of the rotor are substantially unaffected by environmental conditions (e.g. dust) which can degrade the surface of the reflectors and affect the SNR of a detected TGL measurement. In particular arrangements, the housing may provide a vacuum operation environment for the rotor, to minimise for example air-induced drag on the rotor when in operation.

In a particular exemplary arrangement, the housing comprises an upper housing mounting formation 294 which is complementary to the mounting formation 213 on the rotor 200 for mounting the rotor within the housing 290 (also a lower housing mounting formation 295 which is complementary to the lower mounting formation 215 on rotor 200). As mentioned above the housing mounting formations may be a jeweled V-cup assembly to accommodate complementary projections 213 & 215, although it will be appreciated that there are numerous mounting schemes that will be appreciated by the skilled addressee to enable a low-friction rotational mounting of the rotor 200 within the housing 290. As an alternative to a jeweled bearing, which can be quite delicate requiring extra care, an alternative mounting scheme to support the rotor may be a conventional bearing, which may be specifically a high-speed bearing. An advantage of a conventional bearing arrangement is that the mounting scheme may be more robust and that only a single bearing support is required such that bearing friction is minimized. A suitable bearing for this role is the SMR85C-YZZ manufactured by BOCA Bearings Company, Delray Beach, Fla., 33445, USA. Such bearings have ceramic balls with stainless steel races and are ideal for clean (air tight, vacuum) environments and are rated for operation up to about 80,000 rpm. The bearings can be lubricated with an ultra-dry lightning lubricant (UDL) rather than oil or grease packing.

Figure 7:
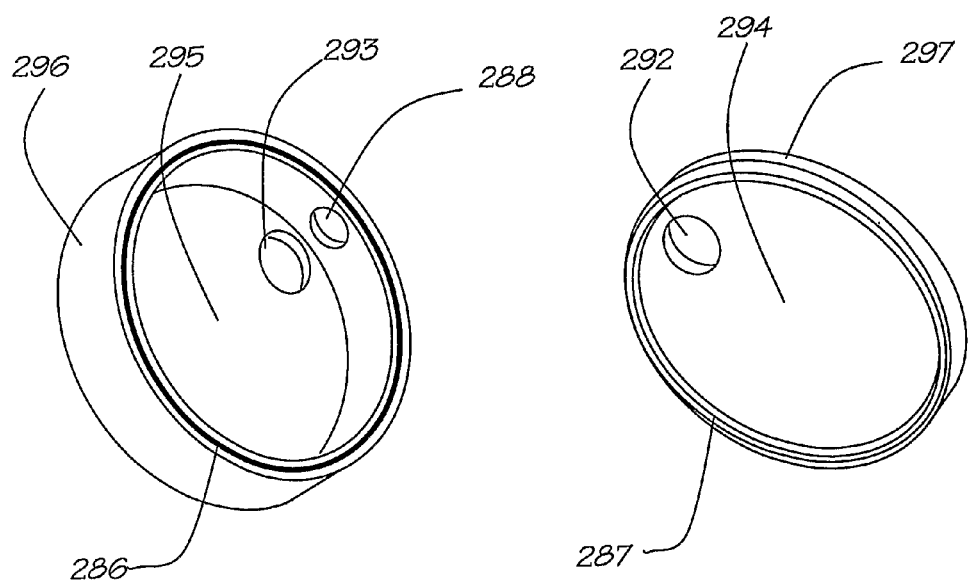
FIG. 7 shows an exemplary housing for the arrangement of the rotor apparatus of FIG. 6.

An exemplary arrangement of a suitable housing 290 is depicted in FIG. 7 where the housing is formed in complementary upper and lower housing units (296 and 297 respectively). In the present arrangement, the housing is formed from a non-magnetic material such as a non-magnetic metal for example titanium, a plastics material for example nylon, PVC a ceramic material, or other suitable material.

In the present example, the lower housing unit 296 includes a first mating feature 286 in the form of a circumferential groove. The upper housing unit 297 includes a second mating feature 287 in the form of a circumferential ridge portion which is complementary to the circumferential groove for mating and sealing the upper and lower housing portions. The mating portions may be designed to provide an airtight seal.

In further arrangements, the internal environment of the assembled housing 290 may be maintained at a pressure less that atmospheric pressure to minimise the amount of atmospheric drag on the rotor 200 when in operation. The internal housing pressure may be maintained at a pressure of between about 0.01 Torr and about 200 Torr, preferably in the range of 0.05 Torr and 100 Torr, and more preferably within the range of between about 0.05 Torr and 10 Torr since drag force is linearly proportional to the density of the fluid (i.e. air within the housing). The reduction of the internal pressure of the housing provides a significant advantage to the rotational operation of the rotor when the rotor is spinning at revolutions of greater than 5,000 or 6,000 rpm since drag force increases proportional to the square of the velocity of the rotor.

In the example housing 290 of FIG. 7, the upper and lower windows 292 and 293 are approximately 6 mm in diameter and the excitation window 288 has a diameter of approximately 4 mm. Each of the windows 292, 293 and 288 are fitted with oversize sapphire windows which have been counter-sunk into the respective housing units to provide an airtight seal.

Figure 8A:
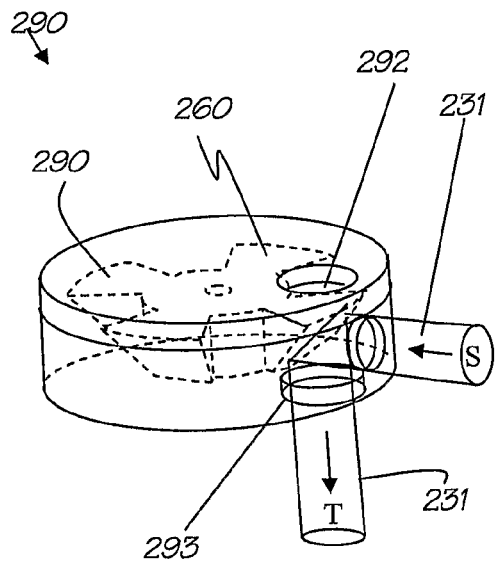
FIGS. 8A and 8B respectively show the excitation and emission (detection) states of the rotor apparatus of FIG. 6.
Figure 8B:
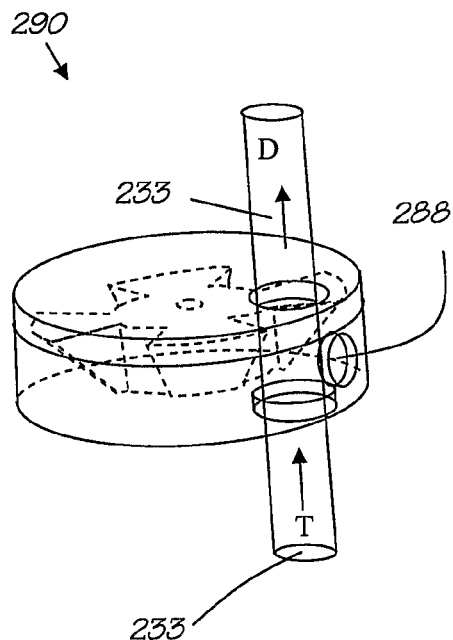

FIGS. 8A and 8B depict a three-dimensional schematic view of the assembled example prototype rotor apparatus 290 during the excitation and detection states respectively. In this arrangement, during the excitation state depicted by FIG. 8A, the excitation light source (marked "S") is located at the illumination light source location such that the excitation beam 231 propagates in the rotation plane of the rotor 290. In use, when the excitation light is incident on each of the reflectors 207 it is reflected through 90 degrees towards the sample (marked "T") under test located at the sample location. During the detection state depicted by FIG. 8B the rotor has moved such that the fluorescence in the sample excited by the excitation beam 231 is able to pass through the upper and lower windows 292 and 293 to a suitable detector located at the detection location (marked "D"). A detector (not shown) at the detection location D may be any suitable electronic detector (e.g. charge coupled device (CCD), image intensified CCD), or other suitable detector including photo-diodes or avalanche photodiodes for detection of the luminescence. The detector may be coupled to a control module (not shown) for recording and analysing signals from the detector. The control module may be coupled via a communication line, wireless or optical coupling (which may be a bi-directional communication line or coupling), for example to the detector. Alternatively, the detector may be coupled to a computer and/or storage means (not shown) for recording and/or analysing signals/images of the detected fluorescence as well as being or instead of being coupled to the control module.

The rotor apparatus of any one of the arrangements described herein may be driven with respect to the movement axis by a mover comprising any one of many drive mechanisms as would be appreciated by the skilled addressee. In the simplest form, the drive mechanism for the rotor may be a simple electric motor (e.g. a DC motor), and the rotation speed of the rotor may be either directly or indirectly dependent upon the voltage applied to the motor. In other arrangements an electromagnetic drive system is envisaged as described herein. More sophisticated drive arrangements may also include in the drive circuitry such as a speed control and/or feedback circuit that reports rotation speed.

Figure 9:
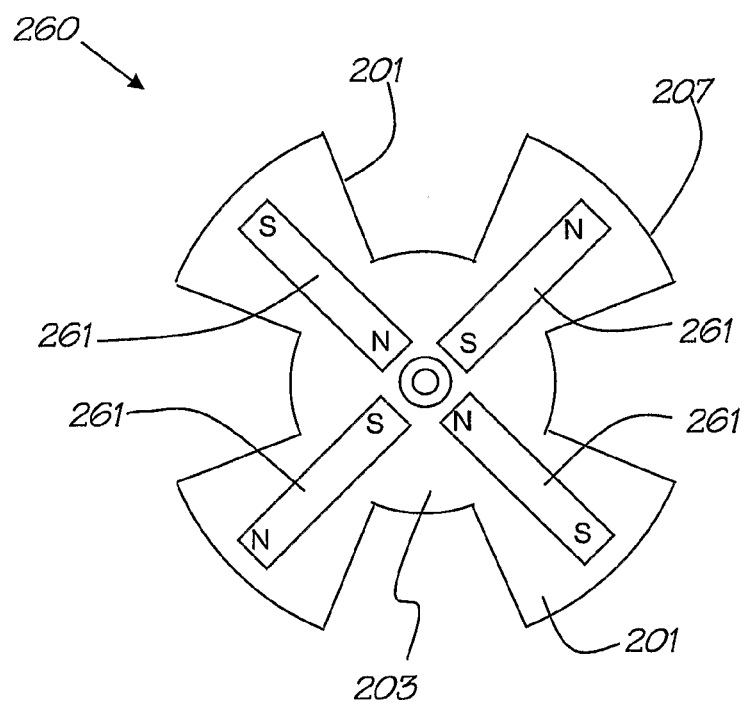
FIG. 9 shows an arrangement of a rotor apparatus according to a further aspect to be used in conjunction with a magnetic drive means.

In a particular arrangement, as depicted in FIG. 9 in top isometric view, a rotor apparatus 260 is operated in use by way of a magnetic drive system. Whilst there are numerous alternative systems available to provide for a rotational drive system, a magnetically driven system provides significant advantages when operating a small rotating unit at high revolution (greater than 5,000 rpm) due to the non-contact nature of the magnetic drive system providing for near-frictionless operation.

Rod magnets 261 with their poles (N=north, S=south) alternating as shown are embedded into each of the arms 201 of the rotor 260. The rotor 260 is preferably made from a metal with low magnetic susceptibility (K) such as titanium, or from an entirely non-magnetic material such as either a plastics or ceramic material, a particular example being a machinable glass-ceramic sold under the trade name MACOR (available from Corning Incorporated, Corning, N.Y. 14831, United States) although functionally equivalent materials as would be appreciated by the skilled addressee may also be used. In other arrangements (not shown), rather than being positioned radially coincident with the rotor vanes, the magnets may be located in the rotor such that the poles of the magnets are aligned parallel with the rotation axis. In this arrangement, the magnets may be located near the rotation axis such that the additional weight of the magnets is maintained near the rotation axis. Other arrangements are also possible as would be appreciated by the skilled addressee.

The rotor apparatus 260 is configurable to be moved with respect to the movement axis 212 and for example may be driven into rotation by a mover utilising the application of an alternating magnetic field that interacts with the magnets 261 fixed within the rotor. In this particular arrangement, it is important to ensure that components of the rotor 260 that are exposed to the external magnetic field do not detract from the force experienced by the fixed magnets in such a way as to reduce the ultimate rotation speed.

In particular arrangements the rotor 260 is formed from a non-magnetic material, for example formed from either a plastic, ceramic, non-metal, or equivalent material), the reflectors 207 may be coated with an evaporated or sputtered metal coating, or vacuum metallisation or other technique to provide a highly specular finish on reflector 207 thereby to enable highly efficient reflection of the excitation light 231 onto the sample 235.

Figure 10:
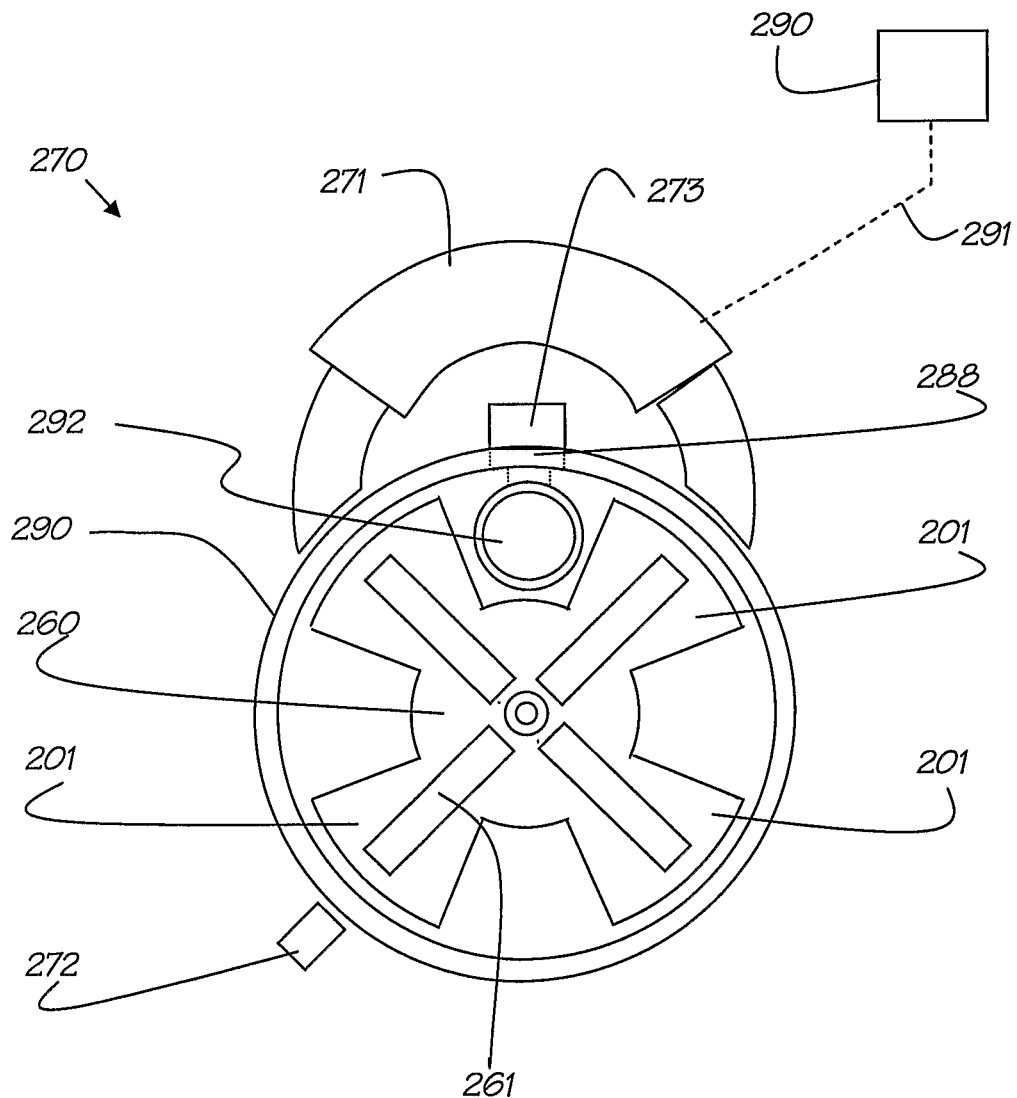
FIG. 10 shows a further arrangement of the rotor of FIG. 9 incorporating the magnetic drive means and an integrated excitation source.

In the arrangements where the rotor apparatus is operated by a magnetic drive system, the alternating magnetic field is applied externally to the rotor housing 290 to induce the rotor 260 to turn at high speed. The alternating magnetic field may be generated by various means as would be appreciated by the skilled addressee. An example magnetic drive system 270 is depicted in FIG. 10 in top schematic view where the magnetic field is produced by electrical pulsing of a stator-coil 271. A coil is wound on a toroid selected from a grade of ferrite that will resist saturation at high magnetic field strength. The magnetic field produced by the coil is focussed by the end faces of the sectioned toroid. The toroid is configured to concentrate the magnetic flux at its poles which are situated as close to the magnets embedded within the rotor arms as possible. Since the force experienced by two magnets decreases by the inverse fourth power of the distance between them, it is preferable to integrate the stator poles within the rotor housing so the pole faces of the stator and rotor are separated by less than a millimeter. This greatly assists acceleration of the rotor to the required speed.

The position and/or speed of the rotor 260 are monitored using a sensor 272, an example of which may for example be a Hall-effect sensor. A control module (not shown) for control of the alternating current applied to the stator coil used in the present example prototype is able to alternately reverse the polarity of the voltage applied to the coil at a frequency of 400 Hz to 1400 Hz to provide rotational speeds of the rotor in the range of about 6,000 to about 60,000 rpm or higher, although it will be appreciated that the control module may be configured to operate the rotor at higher or lower speeds as required. Operation of the rotor at a rotational speed of up to 60,000 rpm allows for detection of luminescent lifetimes of less than 100 μs. The energizing field is synchronized by the Hall-effect sensor to apply the correct polarity to the rotor at the appropriate time within the cycle. The toroid may be potted in a suitable resin to avoid magnetorestriction-induced squeal as would be appreciated by the skilled addressee.

The system 270 also comprises a light excitation source 273 for example an LED light source. The LED 273 is positioned such that it aligns with the excitation window 288 on the housing 290. The rotor is depicted in the detection state such that the upper window 292 is not blocked by the arms 201 of the rotor 260. The wavelength of the light source is selected with respect to the type of fluorescent probe label used in the sample such that the label efficiently absorbs the light from source 273. In many cases the light source will have a wavelength in the ultraviolet region of the electromagnetic spectrum and may be a UV light source with a wavelength in the range of about 150 to 400 nm. In other arrangements, a broadband light source may be desired having wavelengths in the UV, visible and/or infrared regions of the electromagnetic spectrum. Other suitable light excitation sources are available as would be appreciated by the skilled addressee, for example a laser source (e.g. a solid state, gas or semiconductor laser), or a gas discharge lamp (e.g., mercury, sodium, argon, krypton, xenon or neon or combinations thereof) for selective wavelength excitation source of one or more wavelengths or a broadband lamp (e.g. an incandescent light source) for excitation of the sample across a broad wavelength range. An example excitation source that may be suitable in particular arrangements of apparatus and/or systems disclosed herein is a broadband xenon flashlamp light source available from PerkinElmer Optoelectronics, FX-4400 series capable of providing a pulsed light source with up to 60 W (up to ~1 Joule per pulse) average optical power output in the range of between 275 and 2000+ nm with borosilicate glass window material (275 and 2000+ nm for UV glass) up to 20,000 nm with ZnSe window option. Other excitation sources may also be suitable depending on requirements.

The system 270 may further comprise a control module 290 connected to the 271 by communication line 291 (which may be a bi-directional communication line) for operational control of the rotor apparatus. Control module 290 may comprise circuitry for driving the rotor 260 apparatus and optionally the excitation source 273. An example of a suitable drive circuit for use in control module 290 may be the circuit 1200 depicted in FIG. 27, however, other suitable drive circuitry may be envisaged by the skilled addressee.

Figure 11:
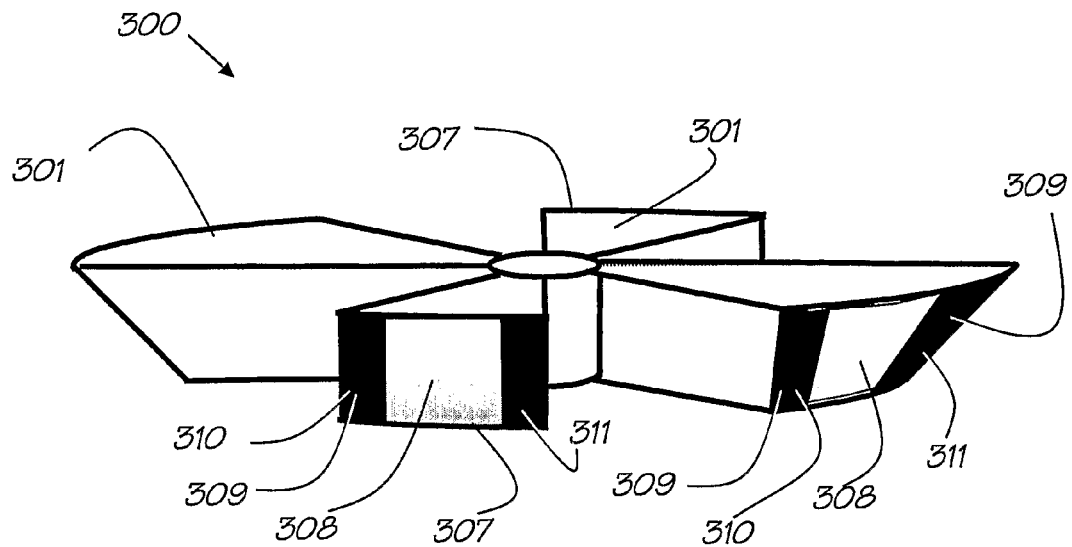
FIG. 11 shows an arrangement of a rotor apparatus according to a further aspect.
Figure 12:
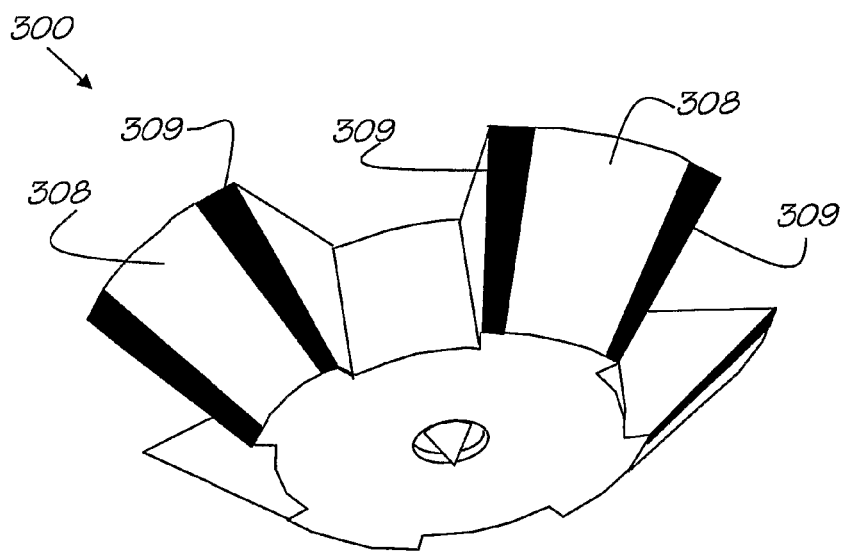
FIG. 12 shows a further depiction of the rotor apparatus of FIG. 11.

A further arrangement 300 of the rotor apparatus is depicted schematically in FIG. 11 (and in a three-dimensional view of an example rotor in FIG. 12). In this arrangement, the reflectors 307 at the distal end of each arm 301 of the rotor 300 comprise a highly reflective portion 308 and two guard portions 309 respectively at either edge of the reflector 307 i.e. located contiguous with the reflector 308 and at the leading 310 and trailing 311 edges (in the case of clockwise rotation of the rotor apparatus) of the arm 301. In other arrangements or the rotor, the guard portion at the trailing edge (311) may be omitted. The guard portions 309 are provided to stop the excitation light being reflected from the reflectors 307 onto the sample (not shown) during the gated/transition state s of the rotation. The guard portions 309 prevent light scatter during the gated/transition state where the excitation beam is only partially incident on the surface 307. The guard portions 309 on the reflective portions are optional when using a pulsed or quasi-cw excitation source which is synchronised to the rotation speed of the rotor. In this situation, the pulsed or quasi-continuous-wave excitation source is configured such that the pulse width of each excitation pulse is shorter than the time that the reflector is aligned between light source and the sample location. Additionally, the pulse is synchronised with the rotor such that each pulse is timed to be incident on a reflector such that is it reflected onto the sample to excite the probe fluorophores and the autofluorophores present in the sample. Preferably the pulse is timed to strike the leading edge portion of the vane (with respect to the direction of rotation of the rotor) such that a portion of the reflector near the trailing edge is not illuminated. The portion of the reflector that is not illuminated then forms the gate portion of the apparatus for gating the excitation and the detection states. The gate portion (i.e. the portion of the reflector not illuminated by the excitation source) is configured (possibly in conjunction with the movement/rotation speed) such that the gate delay time is sufficient for blocking a substantial portion of the autofluorescence from excited autofluorophores in the sample from being detected by the detector. For example the gate delay time may be configured such that it is at least a long as the fluorescence lifetime of the autofluorophores present in the sample. A variable gate delay with a pulsed or quasi-continuous-wave excitation source may be provided by varying the timing of the synchronisation between the light pulse and the position of the reflector such that the portion of the reflector trailing edge that is not illuminated may be increased or decreased as required to give a corresponding increase of decrease in the gate delay time. This synchronisation method of varying the gate delay may be used in conjunction with variation in the movement or rotation speed of the apparatus to provide greater flexibility in the available variation in the gate delay time.

When using a continuous-wave source, however, the rotor cannot adequately block the prompt autofluorescence from the autofluorophores in the sample from reaching the detector, therefore the use of guard portions as described above to define the gate portion(s) of the rotor are preferred. It has been found that the reduction in light scatter through use of guard portions 309 significantly increases the signal-to-noise ratio of the detected fluorescence signal by a factor of between 1.5 to 5 times at least. Effectively, the use of the guard portions autonomously turns a continuous wave excitation source into a quasi-continuous-wave source which is automatically synchronised with the excitation state(s) of the rotor.

In alternate arrangements, the guard portions 309 are implemented as chamfered edges (not shown) that divert the beam from the light emitting source elsewhere (i.e. away from the sample location where the sample under test is situated. Where the apparatus is provided within a rotor housing the chamfered edges may direct the light from the light emitting source a non-reflective or absorbing portion on the inside of the housing.

Figure 13:
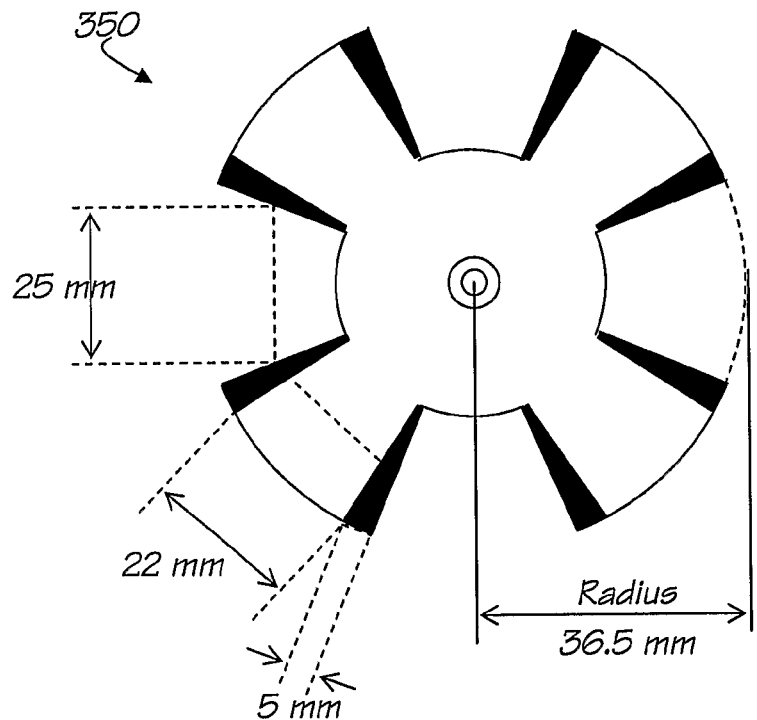
FIGS. 13 and 14 show further depictions of the rotor apparatus of FIG. 11 with representative dimensions.

The size of the guard portions is dependent on the width of the faces at the end of each of the individual rotor arms, the size of the aperture of the housing (i.e. the diameter of the upper and lower windows) and the speed of rotation of the rotor. An example rotor apparatus 350 with approximate dimensions shown in FIG. 13 when operated at 6000 rpm was found to suppress autofluorescence when guard portions of 5 mm were used either side of the 12 mm reflective portion of the rotor faces. The guard portions thus represented 45% of the rotor face in the present example.

The operating characteristics of an exemplary rotor apparatus as described above will now be described with reference to the rotor 400 as depicted in schematic view from below in FIG. 14. The rotor 401 has a diameter of about 28 mm and has four rotor arms 202. The rotor 400 in use is located in a housing 402 similar to that depicted in FIG. 6. The housing 403 has upper and lower windows 404 (only lower window shown) of 6 mm diameter which have their centres located 11 mm from the centre of rotor 401. In the present example, the width of the rotor arms 402, at a radius of 11 mm from the centre of rotor 401, is about 9.34 mm.

The time taken for the rotor arm to entirely traverse the aperture at a speed of 6000 rpm is approximately 2.22 ms and conversely, the aperture will be entirely open for a period of 1.1 ms given that the separation between the arms 402 (at a distance of 11 mm from the centre of rotor 401) is 7.94 mm. In the present example, the excitation beam may be collimated with a diameter of about 5 mm, however operation of the detection system using a rotor in accordance with any of the arrangements described herein would be improved if the excitation beam was brought to focus on the sample location. This would avoid excitation of the target region of the sample by the source when it is visible to the detector and minimise the prompt fluorescence which would likely reduce the SNR of the detected signal.

Guard portions 406 are employed to enable efficient use of the rotor 401 when used in conjunction with a continuous wave excitation source. The guard-bands are situated on either side of the reflective face 405 to either absorb the incident beam during the transition between excitation and detection states or deflect the incident beam away from the sample location. The guard bands are useful when the rotor cannot adequately block prompt emission from reaching the detector. The guard portions 406 provide the gate portions for gating the system intermediate the excitation and the detection states, such the, during the gated/transition state, the excitation light from the light source is prevented from striking the sample at the sample location. In this situation the autofluorophores in the sample are not excited by the excitation light during the gated state and thus the autofluorescence is allowed to decay prior to the apparatus entering the detection state.

During the gated/transition state (refer to FIG. 4B), the aperture 404 is partially open and prompt fluorescence will be visible to the detector unless the excitation pulse is suppressed. Guard portions 406 prevent the excitation beam from reaching the target and they can be implemented as blackened or non-reflective regions on the reflective face 405 or as chamfered edges that divert the beam elsewhere within the rotor housing to be absorbed by a non-reflective coating.

As described earlier, the interval following the excitation of the sample by the excitation source and preceding the acquisition of the fluorescence signal from the sample is referred to as the gate-delay. It is during the gate-delay interval that short-lived fluorescence is resolved from delayed luminescence. Ideally the gate-delay interval is sufficiently long to ensure autofluorescence has faded beyond detection but not so long as to result in substantial loss of the delayed luminescence signal.

With the rotor of the arrangements described herein, the gate delay interval is a function of the angular velocity of the rotor arms 402. In the description of the guard portions 406, it was noted that an example apparatus delivered good results with 55% of the reflective face available for duty (i.e. the guard portions comprised 45% of the reflective face 405, refer to FIG. 13). With reference to the rotor of FIG. 14 with smaller dimensions, the active portion (i.e. that part not comprising the guard portions) of the face 405 is 5.1 mm with adjacent guard regions of 2.12 mm each.

Figure 14:
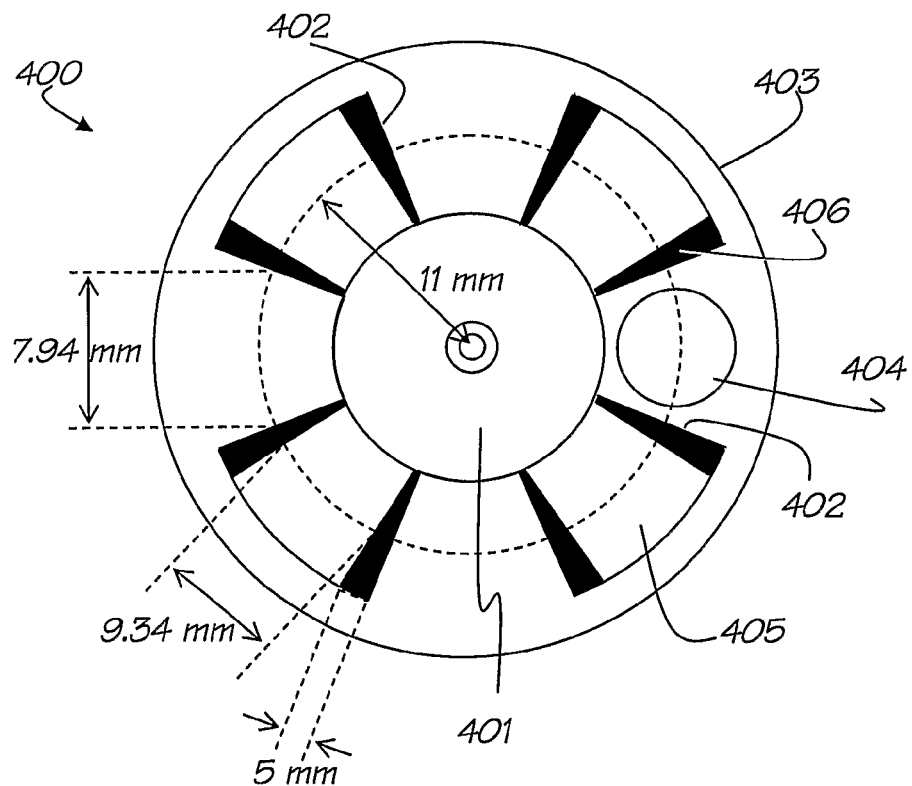

The gate-interval for the apparatus 400 of FIG. 14 can be determined by noting that at 6000 rpm it will take 306 μs for the rotor arms 402 to move the distance of the guard portion 406 and 184 μs at a rotation speed of 10,000 rpm. Using a europium chelate such as BHHCT, which has a lifetime greater than 500 μs, as a fluorescent probe for the sample the luminescence emission from the probe would be reduced by 46% at a rotation speed of 6000 rpm and by 30% when operated at 10,000 rpm.

Whilst the loss in emission intensity is significant (i.e. 30-46% for rotation speeds of between 6,000 and 10,000 rpm), there are inherent compensations in the rotor scheme that are absent from other TGL systems. The reflective face of the rotor acts is an excellent reflector of excitation energy with efficiencies of greater than 90% across a broad range of wavelengths. This feature cannot be duplicated with a dichroic mirror as typically employed in TGL system (refer to FIG. 2). Secondly, UV grade sapphire windows afford transmission rates greater than 80% from 250 nm upwards to the far infra-red. Conventional time-gated luminescence microscopes incur a substantial insertion loss as light passages through the dichroic filter cube that is absent with the reflective rotor design of the present apparatus/systems.

As will be appreciated from the above, a key advantage of the arrangements of the rotor apparatus and system disclosed herein is the capacity to use a continuous wave (cw) excitation source and deliver a stream of excitation pulses which are inherently synchronized to the detection cycle. A further advantage of using cw sources is that a much larger range of source types become available such as mercury arc or xenon arc lamps that are rich in short-wave UV radiation (260-340 nm). Sources in this region are required to excite luminescence from terbium chelate fluorescent probes and are difficult and expensive to obtain from more specialised excitation sources (eg LED or laser sources).

Of course, in other arrangements as described above, the apparatus may be used with a pulsed light source, wherein the apparatus may further comprise a synchronisation module for synchronising the pulses of the pulsed light source with the excitation states of the apparatus. That is, the pulsed light source is triggered to generate a pulse of light when the reflective surface(s) of the apparatus are aligned with the sample location i.e. when the first optical communication path between the illumination light source location and the sample location is open. In this arrangement, it is possible to use light sources which emit broadband light for excitation of a wide variety of fluorescent probe labels (e.g., chelates, or platinum and palladium co-proporphyrins among many others). For example, xenon flashlamps with an emission spectrum spanning approximately 280 to 340 nm may be used, and miniature versions of such light sources are available which may advantageously be incorporated into the apparatus such as within or as part of a removable attachment to the housing of the apparatus.

The rotor apparatus' described herein are widely applicable for and can be readily adapted to different TGL detection schemes. For example, in a particular arrangement, light from a cw or pulsed excitation source may be directed to the rotor by an optical fiber assembly (which may be a solarization-resistant optical fibre assembly to provide enhanced UV transmission, an example of which is available from Ocean Optics of Dunedin, Fla. USA which transmits wavelengths down to about 180 nm without UV-induced degradation of the fibre). The optical source can be readily exchanged for sources providing different excitation wavelengths, and also for sources providing a plurality of discrete wavelengths or a continuum of wavelength in a desired range. For example, two or more optical excitation sources may be transmitted to the rotor apparatus (which may or may not be multiplexed) for excitation of a respective number of fluorescent probes in the sample. Alternatively, an optical source with either a plurality of discrete emission wavelengths (eg, mercury lamp) or a broad emission spectrum (eg. a white light source) may be directed to the rotor apparatus, again for the excitation of a plurality of fluorescent probes.

The choice of excitation source wavelength is largely dependant on the target luminophore of the fluorescent probe; most lanthanide chelates require UV excitation in the range 300 to 380 nm (whilst some europium chelates can be excited at longer wavelengths (up to 380 nm), all known terbium chelates require excitation at wavelengths below 340 nm). Additionally, platinum and palladium chelates and porphyrins possess a strong absorption peak at 390 nm and a second weaker peak at 530 nm, ruthenium at 475 nm, iridium at 310 nm, chromium at 420 nm and osmium at 480 nm. Thus a white-light source can be used that will effectively excite a variety of luminescent ions (Eu, Tb, Sm, Dy, Pt and Pd) to facilitate multiplexed assays.

LED's are particularly suited to the present arrangements, as their small size allows them to be directly incorporated into the housing of the rotor apparatus. LED's also have the advantage they can be driven at low voltage with simple electronics and drive circuitry for the LED can be incorporated into a single control module which controls both the LED and the drive mechanism of the rotor (and also optionally the detector for the TGL apparatus using the rotor apparatus).

The arrangement of the rotor apparatus that utilized a 73 nm diameter rotor (see FIGS. 13 and 14) was tested with both a cw source and a pulsed source. A high-power UV LED (Nichia NCU033S) served in both roles to deliver 50 mW in cw mode or 200 mW in pulsed mode. For operation in pulsed mode, the position of the rotor was sensed optically and the signal used to trigger the electronics responsible for pulsing the LED. Interestingly, when operated at the design speed of 6000 rpm, the cw source delivered brighter luminescence due to the longer excitation period and the shorter gate-delay. The pulsed scheme however resulted in reduced background since prompt (auto) fluorescence could be completely suppressed.

Miniature xenon flashlamps are inexpensive sources of broadband UV that could be employed as pulsed excitation sources for use with the invention.

Figure 15:
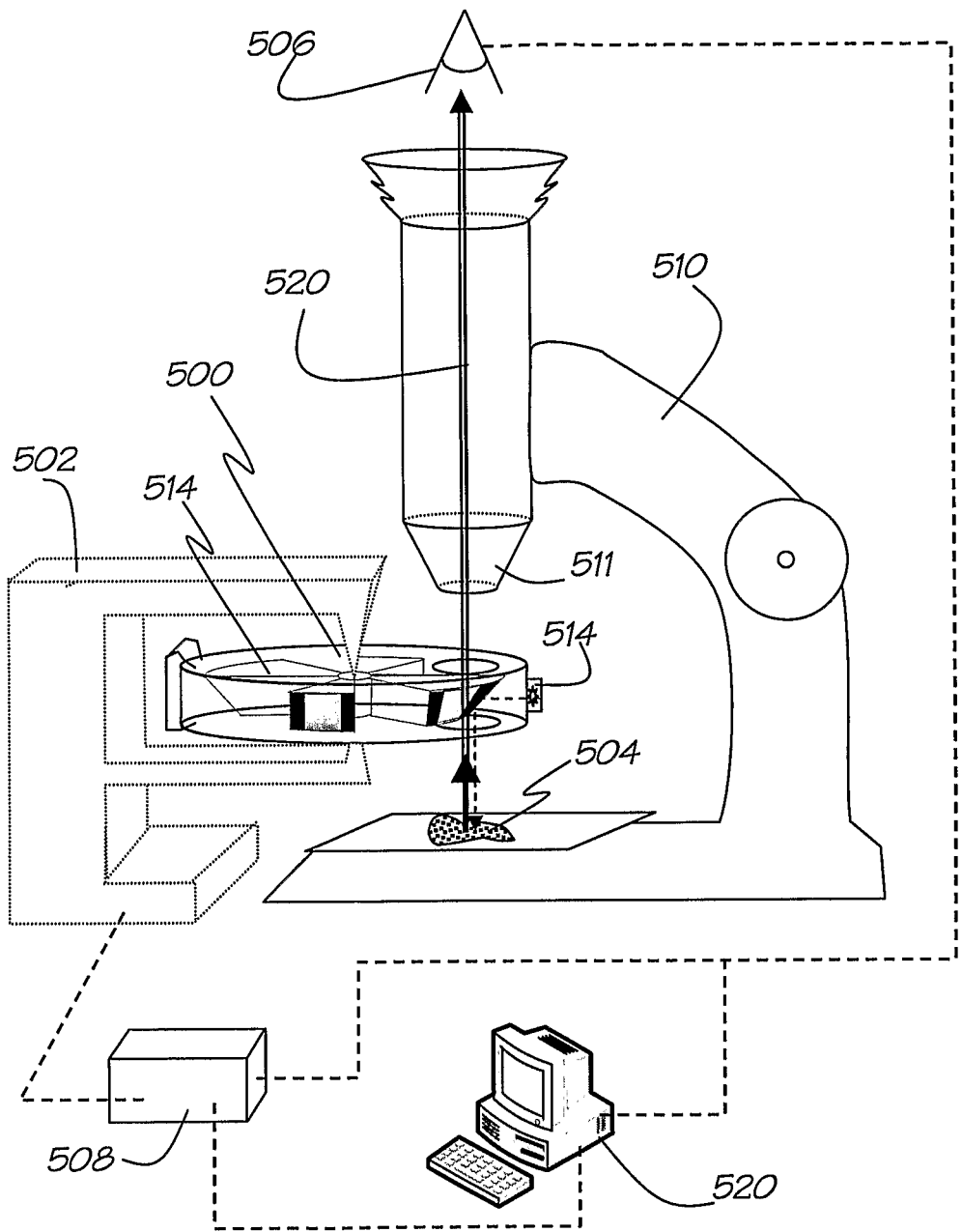
FIG. 15 shows a depiction of the rotor apparatus in use in conjunction with an existing microscope.

In use, the rotor apparatus of any one or more of the above arrangements may be readily used in conjunction with any existing microscope apparatus. The microscope apparatus may be an optical microscope apparatus. In a simple arrangement as depicted in FIG. 15 the rotor apparatus 500 may be provided in a suitable mount 502 which may be inserted into the optical path 520 of a typical microscope 510 between a sample 504, the sample comprising a suitable fluorescent probe, and an observer or detector 506. The microscope 510 can be a simple (non-fluorescence) laboratory microscope as depicted here, or alternatively may be any sophisticated microscope system such as a commercially available TGL system which has had any filters, dichroic mirrors, excitation sources and the like either removed or disabled. The microscope 510 typically comprises a removable objective lens 511. Objective lens 511 may be selected depending on the requirements of the measurement task at hand, for example to provide a desired magnification of the sample 504 when viewed through the microscope 510. The mount 502 may be adapted to connect to a control module 508 for driving the rotor 512 and optionally the excitation source 514 if such a source is included on the rotor apparatus 500. Control module 508 may comprise circuitry for driving the rotor 512 apparatus and optionally the excitation source 514. An example of a suitable drive circuit for use in control module 508 may be the circuit 1200 depicted in FIG. 27, however, other suitable drive circuitry may be envisaged by the skilled addressee. The control module may optionally be provided within the mount 502. The control module may further optionally provide capability of operating a suitable electronic detector (e.g. charge coupled device (CCD), image intensified CCD), or other suitable detector including photo-diodes or avalanche photodiodes for detection of the luminescence and for recording and analysing signals from the detector (which may be located at 506 instead of the observer). Control module 508 may be coupled via a line, wireless or optical coupling, for example to detector 506. Alternatively, detector 506 may be coupled to a computer 530 and/or storage means (not shown) for recording and/or analysing signals/images of the detected fluorescence. Optionally, control module 508 may also be coupled to computer 530.

In this manner, any existing microscope may be readily converted to a TGL microscope in which the time-gated luminescence can directly be observed by an observer. In the intended arrangements, the TGL emission of the fluorescent probe can be observed with the naked eye.

Figure 16:
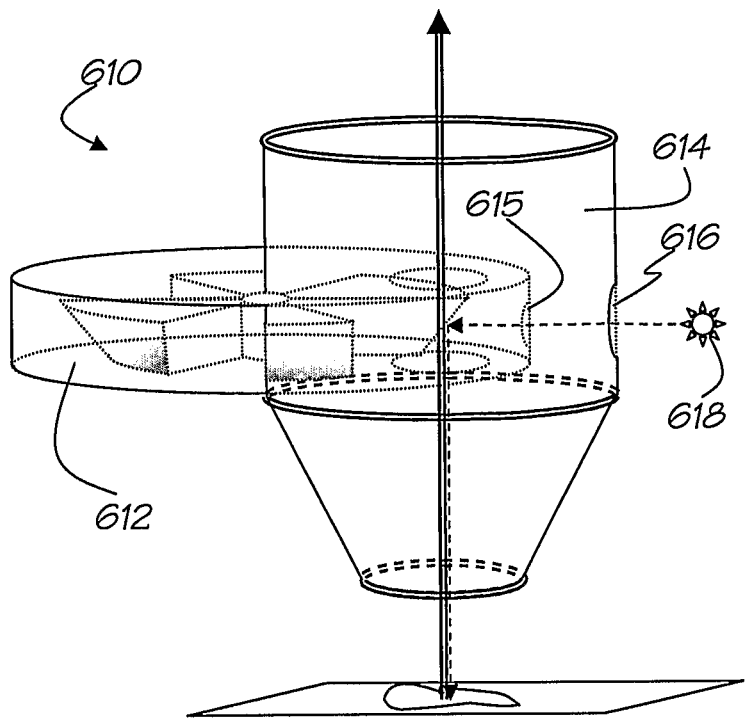
FIGS. 16 and 17 show arrangements of a further aspect of a rotor apparatus incorporated into a microscope objective able to be attached to an existing microscope for conversion of the existing microscope to a time-gated fluorescence microscope.
Figure 17:
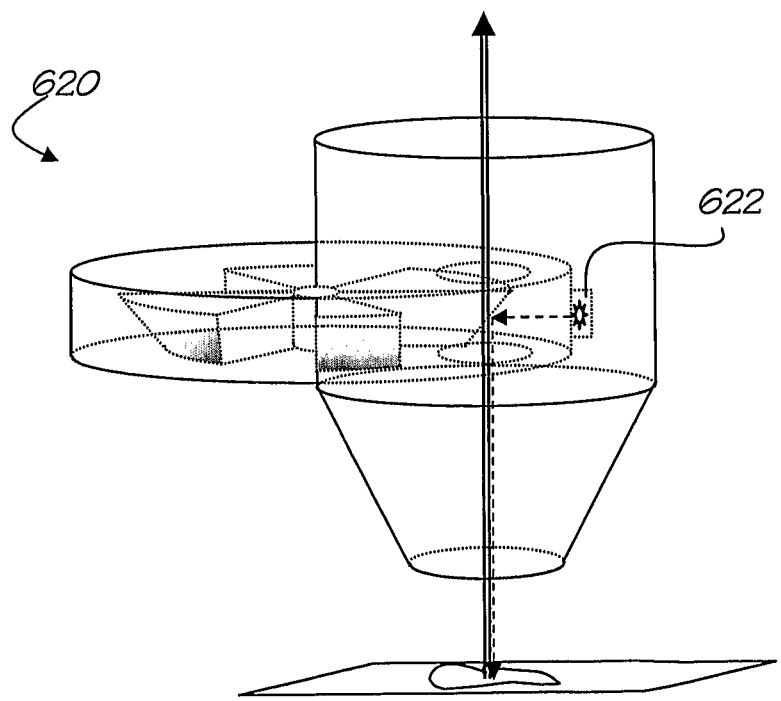
Figure 18A:
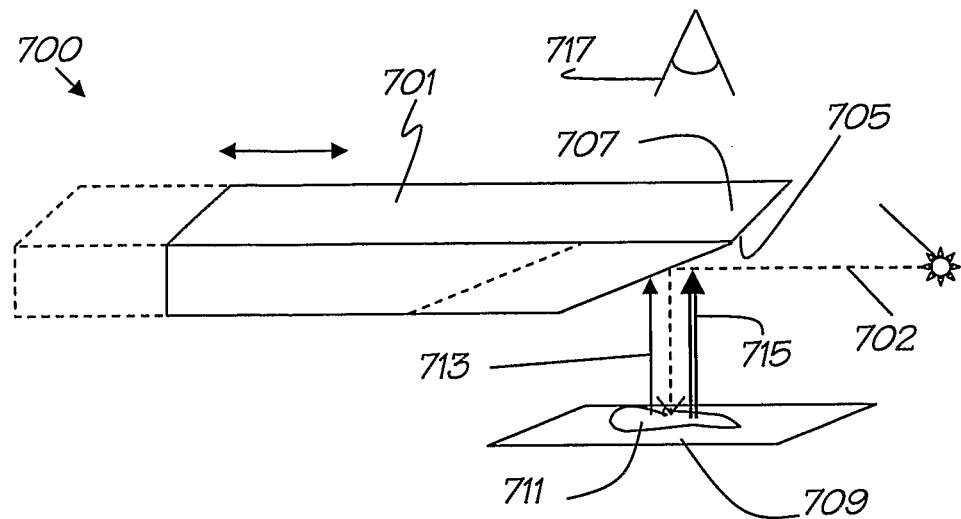
FIGS. 18A and 18B respectively show the excitation and detection states of a further arrangement of an apparatus in accordance with the invention for use in a TGL detection system for auto-synchronisation of excitation and emission (detection) states depicted as an oscillating arm.
Figure 18B:
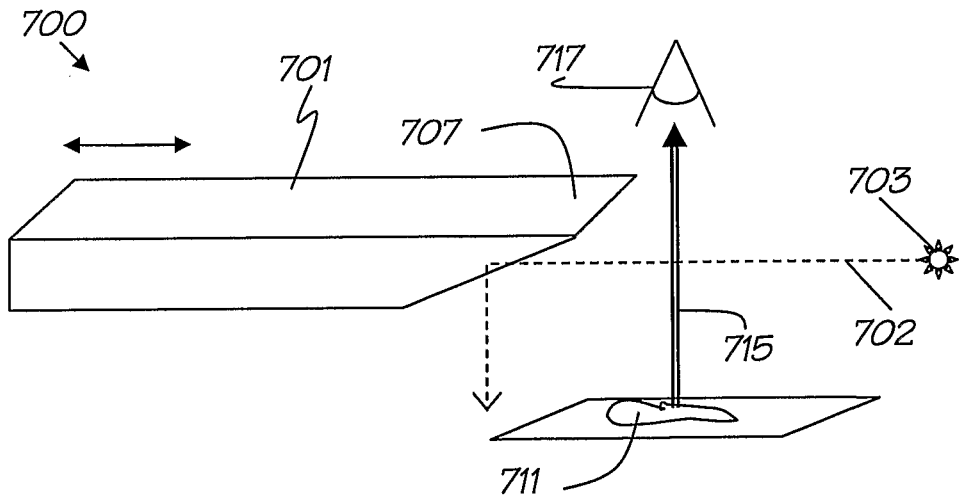

In further arrangements, the rotor apparatus may be provided in an attachment which is able to be connected directly to an existing microscope system. For example, a rotor apparatus 612 as previously described may be incorporated directly into a microscope objective lens 614 suitable for an existing microscope, for example to replace simple objective lens 511 attached to the microscope 510. Examples of a rotor device adapted for attachment to an existing microscope are depicted in FIGS. 16 and 17, which respectively depict Rotor TGL Microscope Objective Lenses (RoTMOL) 610 and 620 with and without an integrated emission source 622. Where the RoTMOL apparatus does not have in integrated emission source (i.e. FIG. 15), suitable means for allowing a suitable excitation source 618 to be directed to the sample via the rotor 612 are required such as windows 615 and 616 shown in the present example. The RoTMOL may also comprise electrical connections (not shown) suitable for connection to a control module for control of the rotor operation. The electrical connections may be adapted for connection to the microscope directly, and control of the rotor may be accomplished through an interface with the microscope.

Exemplary variations of the apparatus of the present invention, may be provided, among others, as depicted in FIGS. 18 to 22. FIGS. 18A and 18B respectively show the excitation and detection states of a further arrangement 700 of an apparatus in accordance with the invention for use in a TGL detection system for auto-synchronisation of excitation and detection states depicted as an oscillating arm 701 which oscillates backward and forward to define the excitation and detection states. In the excitation state, light 702 from light source 703 is incident on reflective surface 705 located at the distal end 707 of arm 701, and is deflected to be incident at a sample location 709. Autofluorophores and probe fluorophores in a sample 711 located at the sample location 709 are excited and generate autofluorescence 713 and fluorescence 715 respectively, both of which are blocked from reaching detector 717 by the arm 701. In the detection state depicted in FIG. 18B, the arm 701 has moved such that the light 702 from light source 703 no longer is incident on the sample 711 so the intensity of the autofluorescence, which has a short autofluorescence lifetime falls rapidly, and the probe-fluorescence with much longer lifetime is able to be detected by detector 717 as the arm 701 no longer blocks the optical path between the sample and the detector. Detector 717 may be any suitable electronic detector (e.g. charge coupled device (CCD), image intensified CCD), or other suitable detector including photodiodes or avalanche photodiodes for detection of the luminescence). Detector 717 may be coupled to a control module (not shown) for recording and analysing signals from the detector 717. The control module may be coupled via a communication line, wireless or optical coupling (which may be a bi-directional communication line or coupling), for example to detector 717. Alternatively, detector 717 may be coupled to a computer and/or storage means (not shown) for recording and/or analysing signals/images of the detected fluorescence as well as being or instead of being coupled to the control module.

Figure 19A:
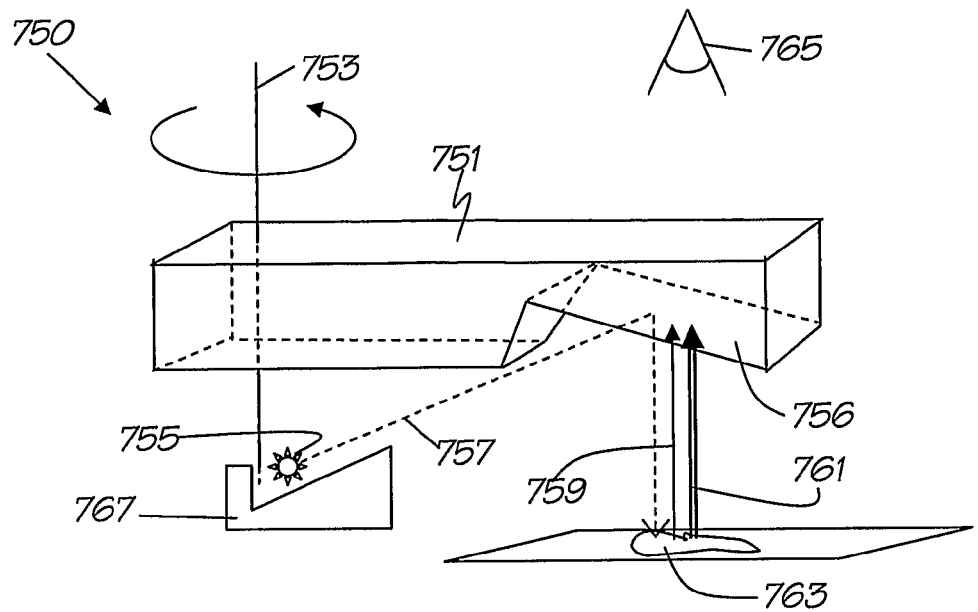
FIGS. 19A and 19B respectively show the excitation and detection states of a further arrangement of the apparatus in accordance with the invention depicted as a rotating am with reflective surface in an alternate orientation to the rotor apparatus' of the previous arrangements.
Figure 19B:
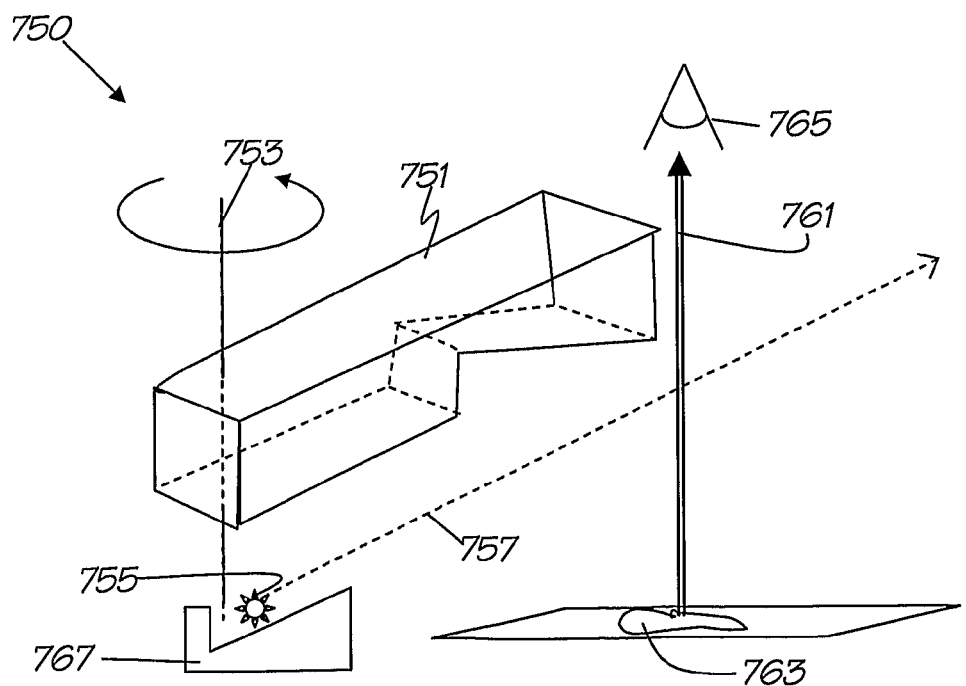

FIGS. 19A and 19B depict a further arrangement 750 of the apparatus, again as a rotating arm 751 which rotates about pivot axis 753 and is similar to the rotor apparatus of FIG. 11. Apparatus 750 may alternately comprise a plurality of arms 751 (not shown) extending radially from the pivot axis. In this arrangement, the apparatus 751 is adapted to deflect excitation light 757 from a light source 755 located underneath the apparatus 750 and may be located at or near the pivot axis. Light 757 from source 755 is deflected by reflector 756 during the excitation state (FIG. 19A) such that it is incident on a sample 763 located at the sample location to excite autofluorescence 759 and probe-fluorescence 761. As the movement of the arm 751 about the pivot axis moves the apparatus 750 into the detection state as depicted in FIG. 19B, the light 757 from source 755 is no longer deflected to the sample, thus the short-lived autofluorescence intensity falls, allowing the probe fluorescence to be detected by detector 765. A beam stop or shield 767 may also be provided to prevent light from source 755 from being incident on the sample directly. This shield may be implemented by enclosing the apparatus 750 in a housing similar to that described above.

Figure 19C:
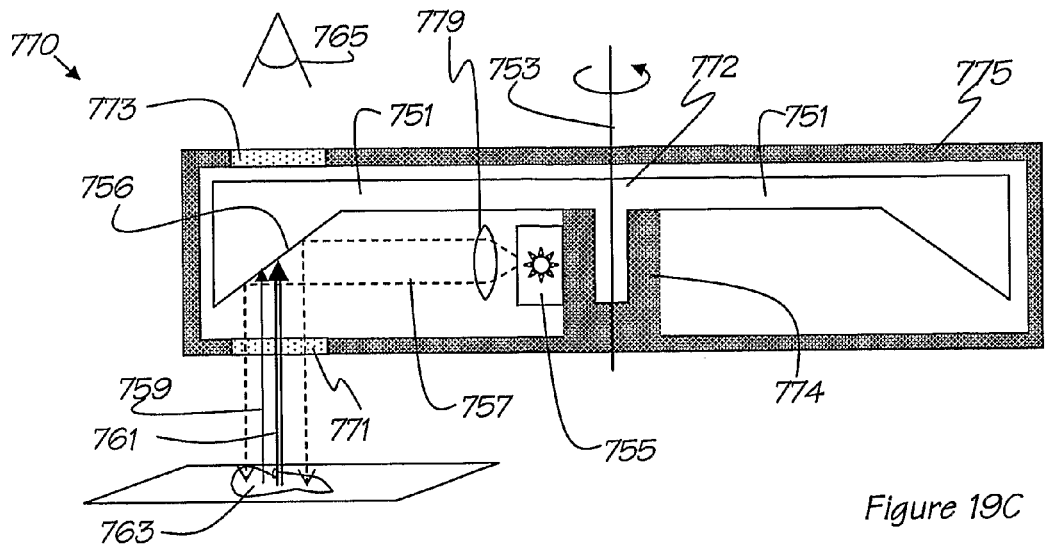
FIGS. 19C to 19D respectively show the excitation and detection states of a further arrangement of the apparatus of FIGS. 19A and 19B.
Figure 19D:
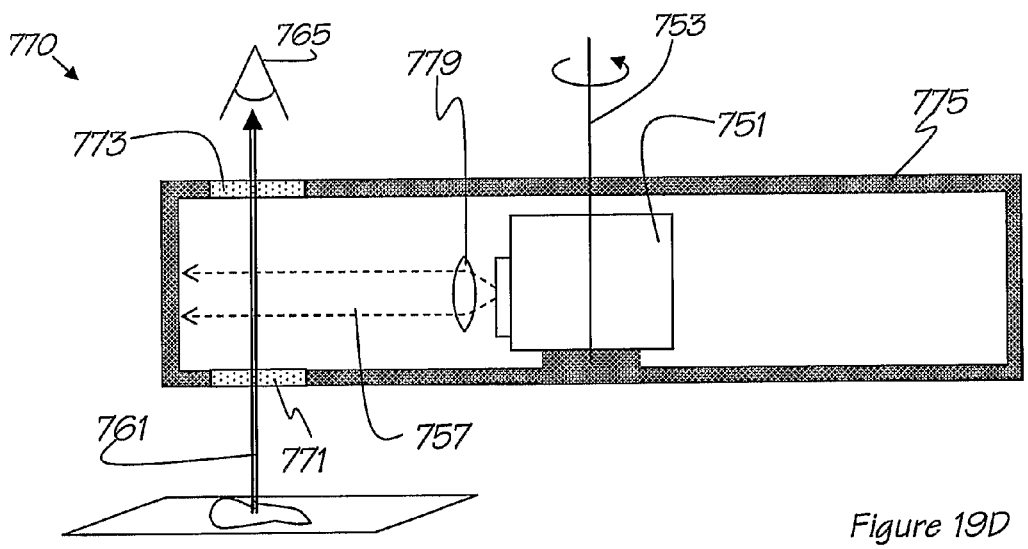

FIGS. 19C and 19D respectively show the excitation and detection states for an exemplary arrangement 770 of the apparatus depicted in FIGS. 19A and 19B. Again, the apparatus is shown as a plurality of arms 751 (in this case two oppositely disposed arms 751) mounted in a housing 775 where the arms form a rotor 772 mounted on a stator portion 774 within the housing 775 which, in use, rotates about rotation axis 753. A light source 755 is located within the housing near the stator portion 774 (i.e. near the rotation axis 753) which directs light 757 radially outward from the rotation axis. Optionally, focussing element(s) 779 are also provided to either collimate light 757, to focus the light 757 on the sample 763, or to otherwise modify the beam shape from the light source as desired. In particular arrangements, the beam may be delivered through refractive or diffractive optics such that the excitation beam pattern is obscured from view during the excitation phase of the detection system utilising apparatus 770.

When the apparatus 770 is in the excitation state, the light is deflected by a reflector 756 on the distal end of arm 751 to be reflected through a first window/aperture 771 in housing 775 to be directed to sample 763. As before, autofluorescence 759 and probe-fluorescence 761 is blocked by arm 751 in the excitation phase. When the arm 751 rotates to the detection state as depicted in FIG. 19D, light 757 is incident on the inner surface of the housing 775, which is configured to be either an non-reflecting or absorbing surface so that none of the light 757 reaches sample 763. The long-lived probe-fluorescence 761 passes back through first window 771 and also a second window 773 to be detected by detector 765. Detector 765 may be any suitable electronic detector (e.g. charge coupled device (CCD), image intensified CCD), or other suitable detector including photo-diodes or avalanche photodiodes for detection of the luminescence. Detector 765 may be coupled to a control module (not shown) for recording and analysing signals from the detector 765. The control module may be coupled via a communication line, wireless or optical coupling (which may be a bi-directional communication line or coupling), for example to detector 765. Alternatively, detector 765 may be coupled to a computer and/or storage means (not shown) for recording and/or analysing signals/images of the detected fluorescence as well as being or instead of being coupled to the control module.

Figure 19E:
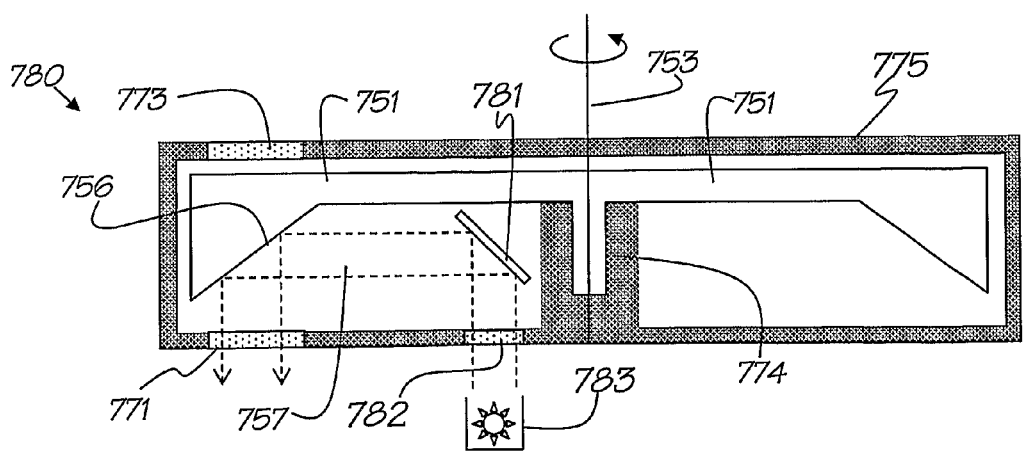
FIG. 19E shows a further arrangement of the apparatus of FIG. 19C.

A still further arrangement 780 similar to arrangements 750 and 770 is shown in the excitation state in FIG. 19E. In this arrangement, the housing 775 is provided with a third window 782 to allow light 757 from an external light source 783 to be directed by a light source reflector 781 to reflector 756 as before. The a light source reflector 781 is located within the housing proximal to the stator portion 774 and the rotation axis 773 and is typically fixed in place relative to the stator portion 774.

In each of FIGS. 19C to 19E, the windows 771, 773 and 782 in housing 775 are each preferably highly transmissive windows formed for example from a material such as sapphire. The reflector 756 on the inner surface of the arm 751 is a highly reflective reflector capable of efficiently reflecting light within a large wavelength range, for example light in the range of about 350 to 800 nm or more. In alternate arrangement, optical fibres with or without the use of a source reflector 781 may also be used for directing excitation light from the light source onto the reflector 756 on arm 751 of the apparatus.

The apparatus (770 or 780) may be supported in a low friction jewel mount (not shown) and the stator/housing 775 may be evacuated to further reduce drag on the arms 751 during operation. The apparatus may be driven internally by (electro) magnetic fields either with or without the use of fixed magnets as described above.

Figure 20A:
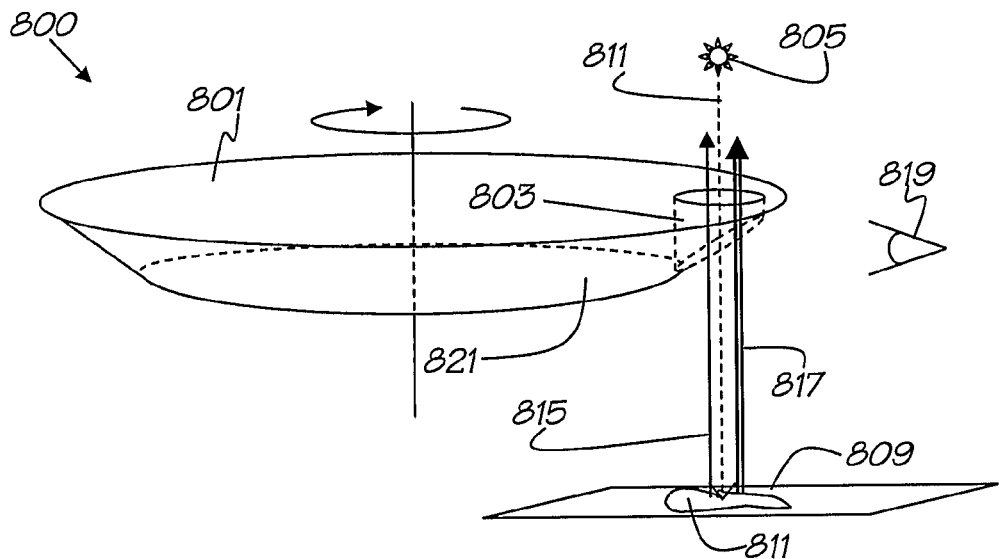
FIGS. 20A and 20B respectively show the excitation and detection states of a further arrangement of the apparatus in accordance with the invention depicted as a rotating disc.
Figure 20B:
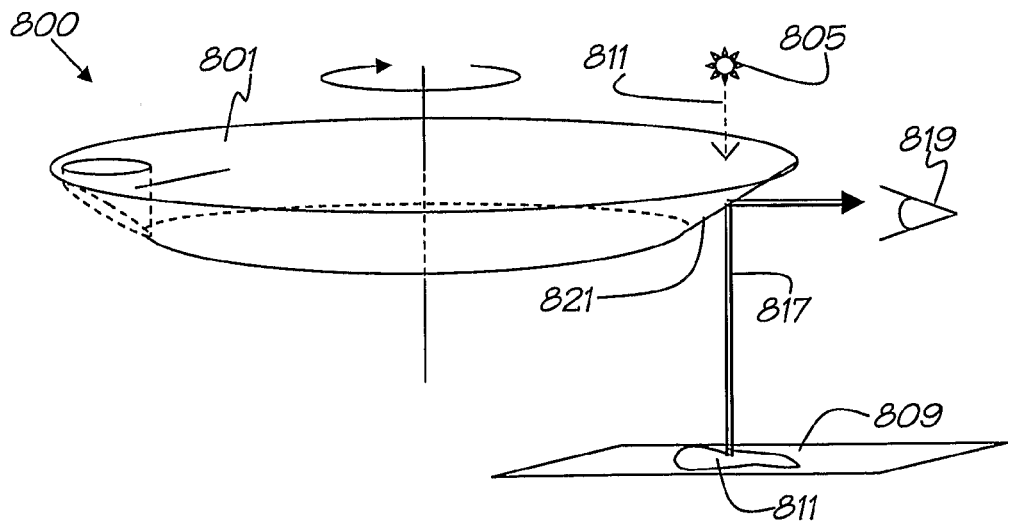

A further arrangement 800 of the apparatus is depicted in FIGS. 20A and 20B as a rotating disc 801 comprising one or a plurality (only one shown) of aperture(s) 803 through the disc defining an optical path between a light source 805 and the sample location 809. In the excitation state of FIG. 20A, the aperture 803 is aligned with the optical path such that light 811 from the source 805 is incident on a sample 813 at the sample location, thereby to excite autofluorescence 815 and probe-fluorescence 817. In the excitation state, the autofluorescence 815 and probe-fluorescence 817 pass back through the aperture 803 and thus are not detected by detector 819. In the detection state depicted in FIG. 20B, the disc has moved such that the aperture 803 is misaligned with the optical path and thus the light 811 from the source is no longer incident on the sample and thus the intensity of the autofluorescence 815 falls rapidly so that the probe fluorescence is deflected by a reflector 821 contiguous with the upper and lower surfaces of the disc 801 and with the radial extent of the disc 801 to be detected by detector 819. Detector 819 may be any suitable electronic detector (e.g. charge coupled device (CCD), image intensified CCD), or other suitable detector including photo-diodes or avalanche photodiodes for detection of the luminescence. Detector 819 may be coupled to a control module (not shown) for recording and analysing signals from the detector 819. The control module may be coupled via a communication line, wireless or optical coupling (which may be a bi-directional communication line or coupling), for example to detector 819. Alternatively, detector 819 may be coupled to a computer and/or storage means (not shown) for recording and/or analysing signals/images of the detected fluorescence as well as being or instead of being coupled to the control module.

It will be appreciated that the operation of this arrangement is similar to that as described in reference to the arrangement of FIGS. 5A and 5B, however with the illumination light source location and the detector reversed, thus similarly, the rotor apparatus 200 of FIGS. 5A and 5B can be implemented in a similar manner to that of apparatus 800 described above.

Figure 21A:
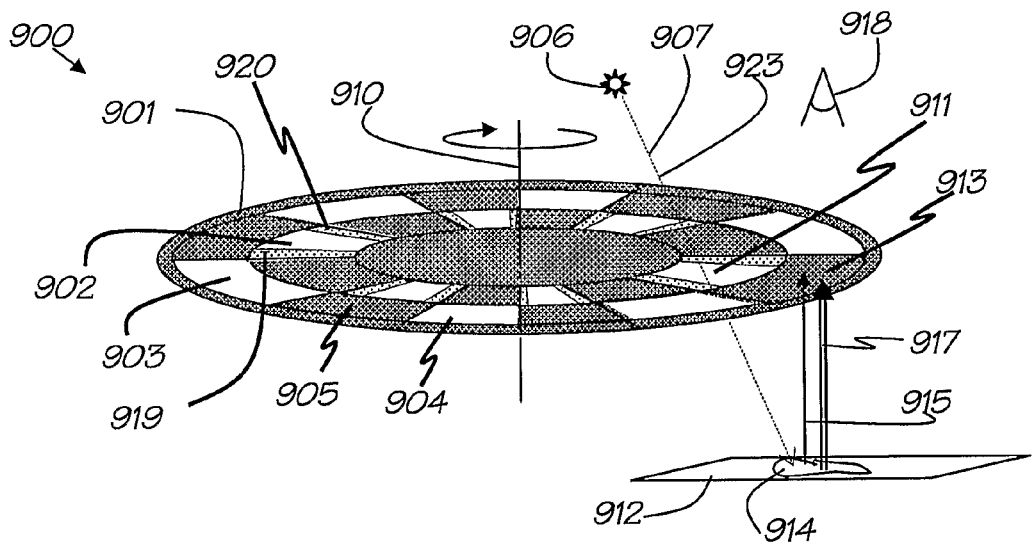
FIGS. 21A and 21B respectively show the excitation and detection states of a further arrangement of the apparatus in accordance with the invention for auto-synchronisation of excitation and emission (detection) states of a TGL system without the use of reflectors.
Figure 21B:
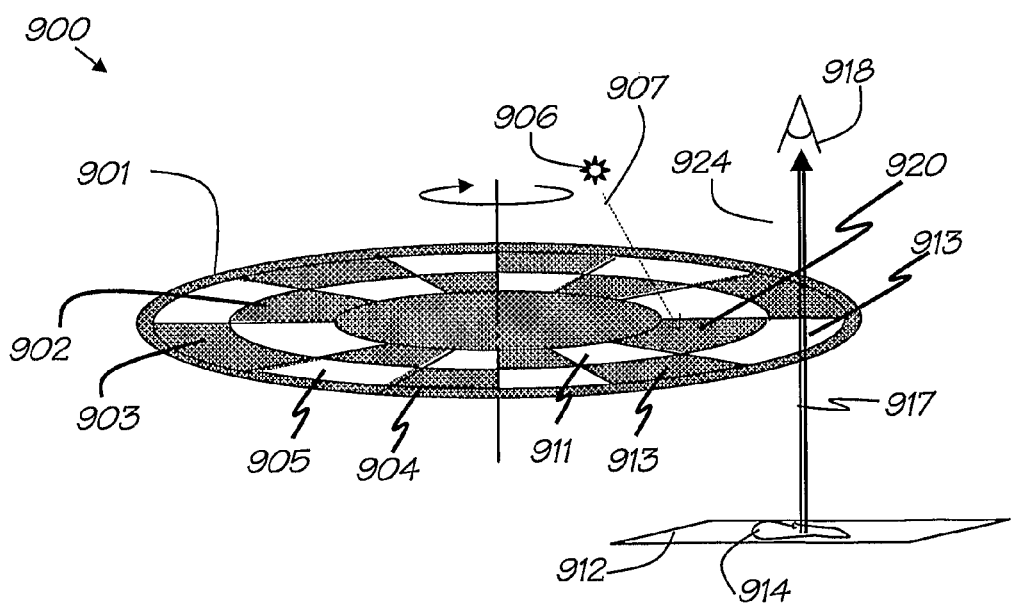

A still further arrangement 900 is depicted respectively in excitation and detection states in FIGS. 21A and 21B where the apparatus is depicted as a chopper wheel 901 and does not require the use of a reflector as per the previous arrangements. In this arrangement, the chopper wheel 901 comprises an inner region 902 at a first radius from the pivot (rotation) axis 910 and an outer region 903 ad a second radius from the axis, each region comprising alternating open 904 and closed 905 portions to respectively either permit light from passing through the chopper wheel. The inner region is located with respect to an excitation light source 906 such that, during the excitation state (FIG. 22A), light 907 from the light source 906 passes through an open region 911 and is incident on a sample location 912 on first communication path 923. The adjacent open and closed portions in the inner region and the outer region are complementary such that, during the excitation state when an open portion 911 of the inner region 901 is aligned with the light source, the adjacent portion 913 of the outer region 903 is closed such that autofluorescence 915 and probe fluorescence 917 from an excited sample 914 is blocked from being detected by a detector 918. Detector 918 may be any suitable electronic detector (e.g. charge coupled device (CCD), image intensified CCD), or other suitable detector including photo-diodes or avalanche photodiodes for detection of the luminescence. Detector 918 may be coupled to a control module (not shown) for recording and analysing signals from the detector 918. The control module may be coupled via a line, wireless or optical coupling (which may be a bi-directional communication line or coupling), for example to detector 918. Alternatively, detector 918 may be coupled to a computer and/or storage means (not shown) for recording and/or analysing signals/images of the detected fluorescence as well as being or instead of being coupled to the control module.

During the detection state as depicted in FIG. 22B, the chopper has moved about the rotation axis 910 such that a closed portion 920 of the inner region 902 is aligned with the light source 906 such that it is blocked from reaching the sample 912 and thus the short lived autofluorescence rapidly reduces in intensity. Conversely, the apparatus has moved such that an open portion 922 of the outer region 903 is aligned with the detector therefore the long-lived probe fluorescence 917 from the excited sample 912 is detected by detector 918 via first communication path 924. The arrangement 900 may also include gate portions 919 and/or 920 for gating the first and second optical communication paths. The gate portions 919 and 920 may be located either on the inner region of the chopper as shown in FIG. 21A or the outer region (not shown) of the chopper 901. In other arrangements, there may be no gate portions as shown in FIG. 21B which may be used in conjunction with a pulsed, quasi-cw or switched light source 906.

Figure 22:
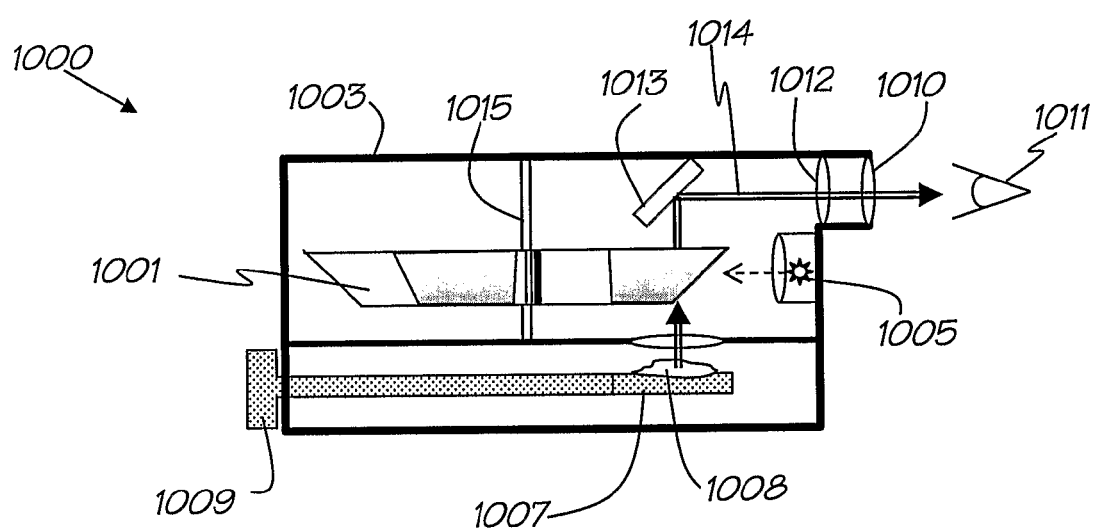
FIG. 22 shows an example arrangement of a TGL detection apparatus and system in accordance with any one of the aspects or arrangements of the invention described herein embodied in a portable or hand-held form FIGS. 23A and 23B respectively depict cross-section and cut-away views of a schematic representation of a further arrangement of a rotor system and apparatus according to a further aspect to be used in conjunction with a magnetic drive means.

In still further arrangements (one exemplary arrangement shown in side cut-away view is depicted in FIG. 22 when in the detection state), it is envisaged that the apparatus may be incorporated into a portable or hand-held device 1000 comprising, an apparatus or rotor 1001 as described in any one of the arrangements described herein mounted in a housing 1003, and a suitable light source 1005 for excitation of photoluminescence in a desired probe fluorophore or organism to be detected. The portable device also comprises either a sample location 1007 at which a sample 1008 expected to contain either the desired probe fluorophore or organism to be detected can be placed. The sample location 1007 may comprise a removable portion 1009 of the device 1000 which can be inserted into the device once it has been loaded with the sample 1008 to be tested. The device 1000 also comprises an eyepiece 1010 suitably located for an observer or detector 1011 to detect the fluorescence excited in the sample by the light source when in use. Detector 1011 may be any suitable electronic detector (e.g. charge coupled device (CCD), image intensified CCD), or other suitable detector including photo-diodes or avalanche photodiodes for detection of the luminescence. Detector 1011 may be coupled to a control module (not shown) included in device 1000 for recording and analysing signals from the detector 1011. The control module may be coupled via a line, wireless or optical coupling (which may be a bi-directional communication line or coupling), for example to detector 1011. Alternatively, detector 1011 may be coupled to a computer and/or storage means (not shown) for recording and/or analysing signals/images of the detected fluorescence as well as being or instead of being coupled to the control module. Apparatus 1000 may alternately comprise an electronic display at eyepiece 1010 which may display images of photoluminescence detected by a suitable detector intermediate the sample 1008 and the eyepiece 1010 (not shown).

The device may optionally comprise additional optics 1012 and/or an optional turning reflector 1013 for focusing/directing light 1014 from the sample location 1007 to the eyepiece 1010. The device additionally comprises a suitable drive means (not shown) for movement of the rotor apparatus 1001 about pivot axis 1015. The drive means may also comprise a variable control (not shown) for adjustment of the rotation speed of the rotor apparatus in accordance with requirements. The device may in some arrangements be constructed from inexpensive materials (e.g. plastics materials) and may be a single-use device or may be limited to be used for test of a limited number of samples before it is discarded.

Figure 23A:
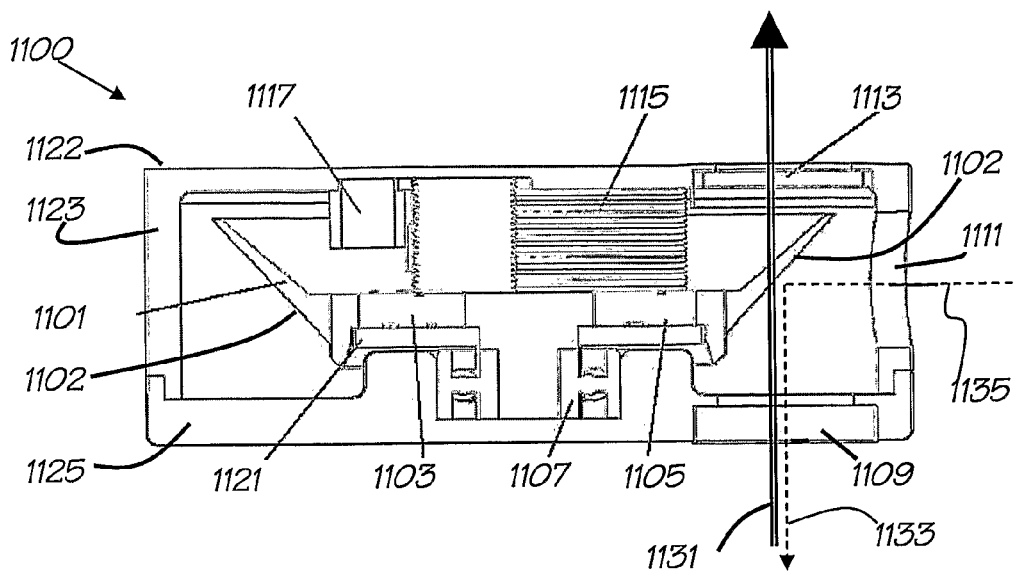
Figure 23B:
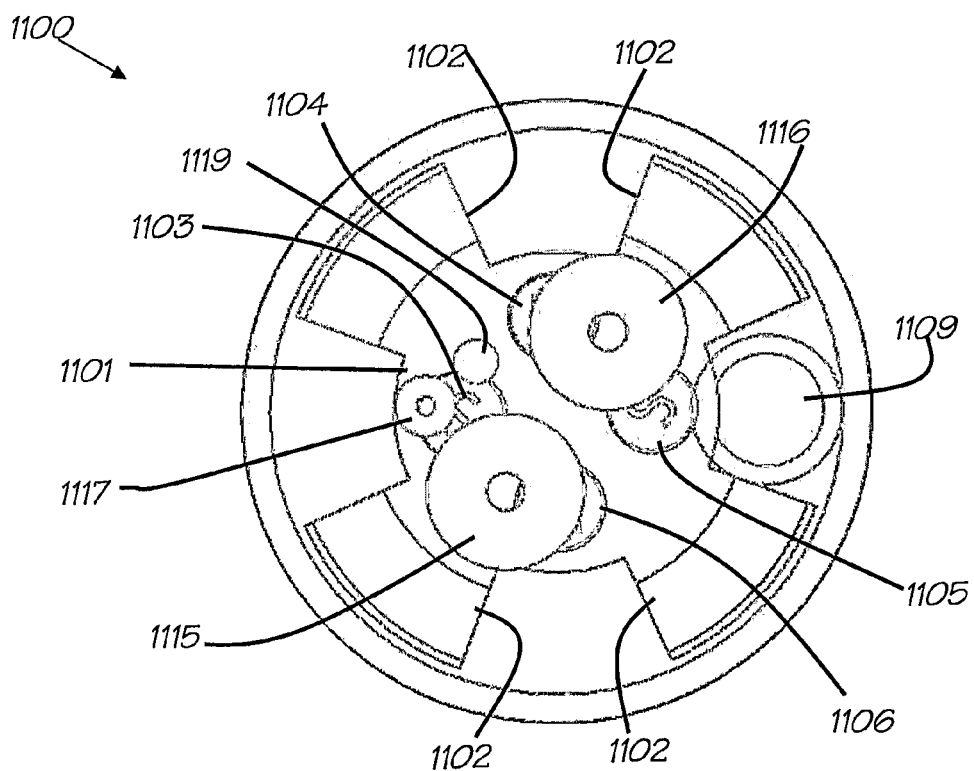
Figure 24:
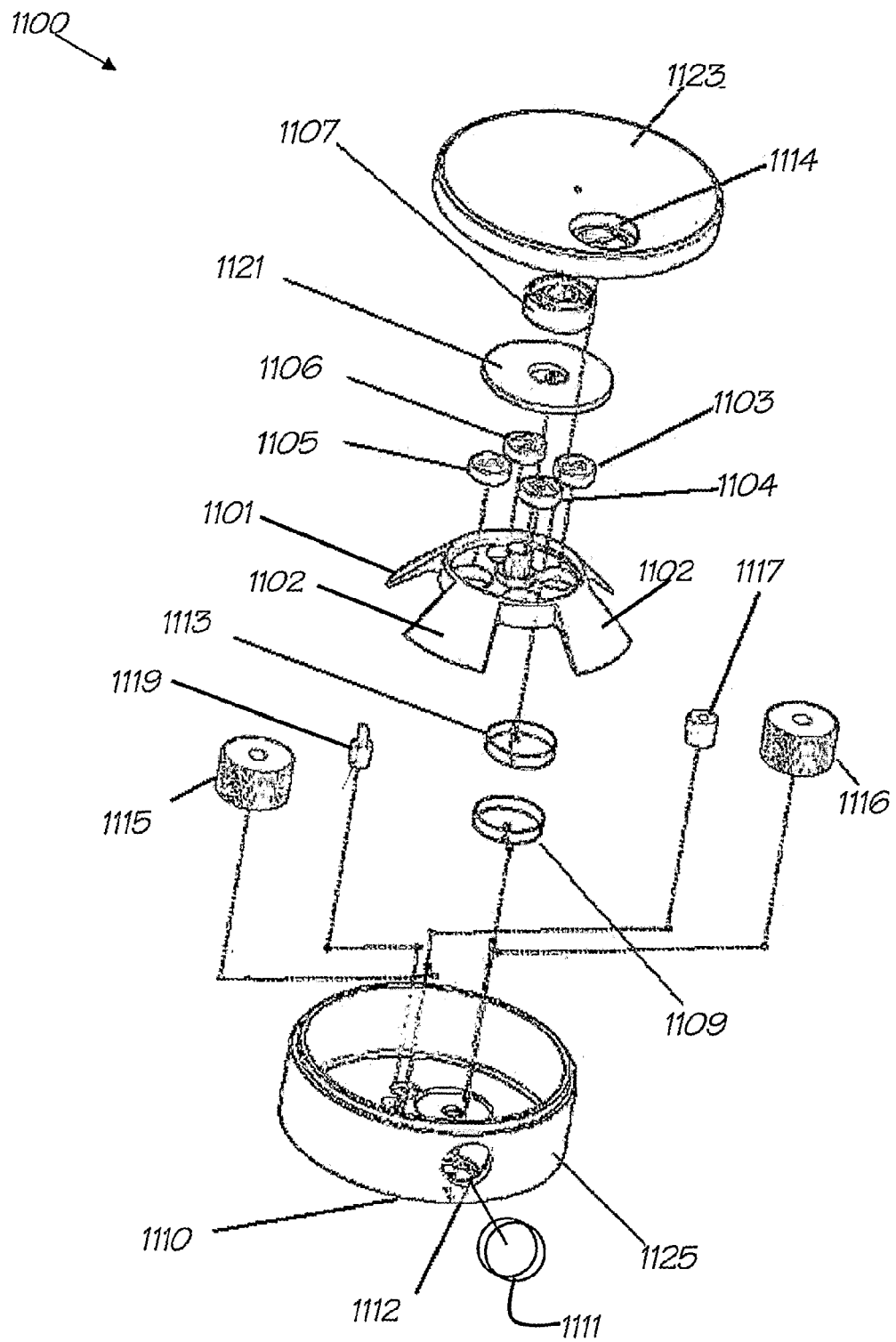
FIGS. 24 and 25 show exploded schematic views of the rotor system of FIGS. 23A and 23B.
Figure 25:
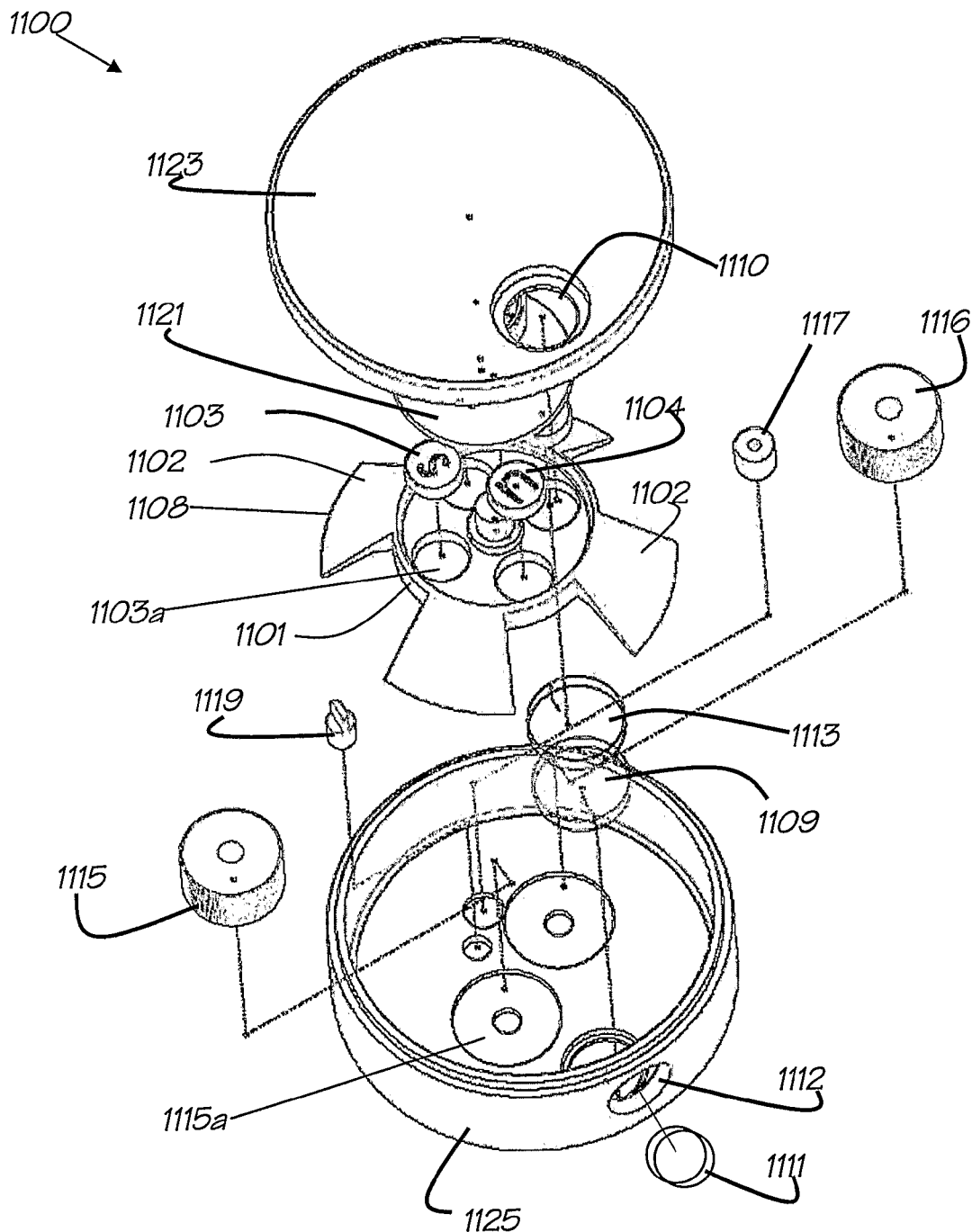

A further exemplary arrangement of a rotor system 1100 using a magnetic drive system (similar to that depicted in FIG. 10) is depicted schematically in FIGS. 23 to 26. FIGS. 23A and 23B are respectively cross-sectional and cut-away views of rotor system 1100. FIGS. 24 and 25 are exploded schematic views of rotor system 1100 showing the individual components of the system.

Referring to FIG. 23A, rotor system 1100 comprises a vane-type rotor 1101 having reflective surfaces 1102 on each of vanes 1108. The faces 1102 of the rotor 1101 may also be configured with guard portions (not shown) such as guard portions 309, 406 as depicted in FIGS. 11 to 14 to enable use with a continuous wave excitation source. The rotor 1101 is preferably made from a metal with low magnetic susceptibility (K) such as titanium, or from an entirely non-magnetic material such as either a plastics or ceramic material, a particular example being a machinable glass-ceramic sold under the trade name MACOR (available from Corning Incorporated, Corning, N.Y. 14831, United States) although functionally equivalent materials as would be appreciated by the skilled addressee may also be used.

Figure 26:
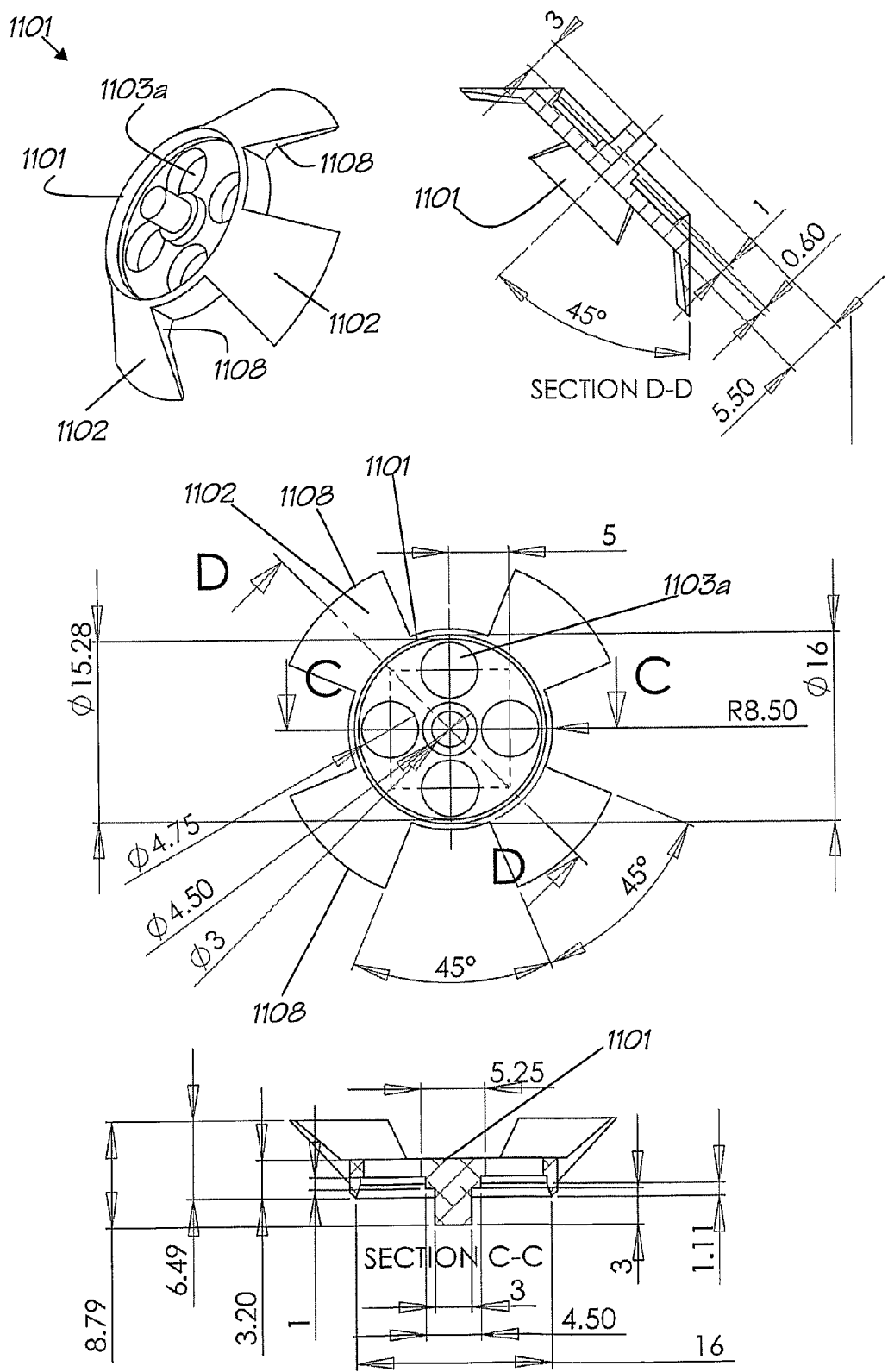
FIG. 26 is a schematic drawing of an exemplary rotor 1101 for use in a rotor system as described herein, showing exemplary dimensions of a rotor designed for incorporation in a existing microscope device.

FIG. 26 is a schematic drawing of an exemplary rotor 1101 for use in a rotor system as described herein, showing exemplary dimensions of the rotor, relative orientations of the angle the reflective surfaces 1102 make with the rotation direction, and example size (circumferential extent) of each vane of the four vane rotor 1101 depicted. The dimensions of the rotor 1101 as indicated in FIG. 26 are designed to be incorporated in an upright stage Olympus microscope (BX-51) for instant conversion of the Olympus microscope to a TGL-capable microscope. As will be appreciated by the skilled addressee, modifications to the actual dimensions of the rotor made be made in accordance with requirements, for example, for incorporation in a different microscope brand or model.

The rotor is housed in a housing 1122 (similar to housing 290 depicted in FIG. 7) comprising complementary upper and lower housing units 1123 and 1125 respectively. As before, the housing 1122 may be formed from a non-magnetic material such as a non-magnetic metal for example titanium, a plastics material for example nylon, PVC a ceramic material, or other suitable material. When in complementary engagement, the upper and lower housing units 1123 and 1125 may form an airtight housing 1122. The airtight engagement of the housing unit may be sufficient for operation under vacuum conditions with housing 1122.

The housing 1122 is generally opaque and comprises upper and lower windows (1109 and 1113 respectively) to allow a fluorescence signal from a sample (not shown) to propagate along the second optical communication path 1131 and pass between the rotor vanes 1102 during the emission/detection state in a similar manner to that described above. The housing 1122 also comprises an excitation window 1111 to allow excitation light 1135 from an external excitation light source (not shown) to enter the housing 1122 to be reflected by reflectors 1102 through the lower window 1109 towards the sample (not shown) along the first optical communication path 1133. Windows 1109, 1111 and 1113 may be formed from a suitable transparent material, for example sapphire, and are mounted in the housing in complementary window seat portions 1110, 1112 and 1114 respectively as shown in FIG. 24. window seat portions may provide an airtight seal with respective windows when seated to provide an airtight housing 1122.

Rotor 1101 is mounted within the housing 1122 on a bearing 1107 for rotation operation thereof as described above. Bearing 1107 supporting rotor 1101 may be a conventional bearing, which may be specifically a high-speed bearing. An advantage of a conventional bearing arrangement is that the mounting scheme may be more robust and that only a single bearing support is required such that bearing friction is minimized. A suitable bearing for this role is the SMR85C-YZZ manufactured by BOCA Bearings Company, Delray Beach, Fla., 33445, USA. Such bearings have ceramic balls with stainless steel races and are ideal for clean (air tight, vacuum) environments and are rated for operation up to about 80,000 rpm. The bearings can be lubricated with an ultra-dry lightning lubricant (UDL) rather than oil or grease packing.

The magnetic drive system of rotor system 1100 comprises magnets 1103 and 1105, magnets 1104 and 1106 (shown in FIG. 23B), and coils 1115 and 1116 (shown in FIG. 23B). Rotor magnets 1103 to 1106 are engaged with the rotor 1101 such that electromagnetic excitation of magnets 1103 to 1106 from drive coils 1115 and 1116 cause the rotor 1101 to rotate as a desired rotation speed as described above. Rotor magnets 1103 to 1106 in the present arrangement are depicted as disc magnets located in complementary receptacles (e.g. 1103a) of rotor 1101 with alternate "n" and "s" orientations as shown. Rotor magnets 1103 to 1106 are preferably fixedly engaged with the rotor 1101. Drive coils 1115 and 1116 in the present arrangement are located in complementary receptacles 1115a and 1116a of housing unit 1125. Rotor system 1100 also comprises a sensor means 1119, for example a Hall effect sensor, for sensing the position (either absolute or relative position) of the rotor (e.g. the location of the rotor vanes) within the housing. Sensor means 1119 may also sense the rotation speed of the rotor 1101 when in operation. The sensor means 1119 may sense the location of the rotor magnets 1103 to 1106 as the rotor turns to determine the location of the rotor vanes and/or the speed of the rotor.

In the present arrangement, rotor system 1100 further comprises a starting means 1117 as depicted in FIGS. 23B to 26. The starting means is adapted to assist with initial start-up of the rotor when in operation. Starting means 1117 may be beneficial to assist with self starting of a rotor system which may be difficult in a magnetic drive arrangement with a limited number of field coils provided (for example, the present exemplary arrangement of rotor system 1100 comprises two field coils 1115 and 1116). That is, if one or more of the rotor magnets when the rotor is at rest prior to operation is aligned with a drive coil, mere application of a current to the drive coil may be insufficient to commence rotation of the rotor. The addition of starting means 1117 assists by aligning the position of the rotor vanes 1102 with respect to the starting means and in turn the field coils 1115 and 1116 when the rotor 1101 is at rest. For example, suitable starting means may comprise a small ferromagnetic object, for example a ferrite bead, located in housing 1122 such that, when the rotor 1101 is at rest, one of the drive magnets (1103 to 1106) of rotor 1101 aligns with this ferromagnetic object 1117. The addition of the starting means is also particularly beneficial when the field drive coils 1115 and 1116 do not have a central flux concentrator (such as a ferrite core) and thus do not attract the rotor magnets (1103 to 1106). By offsetting the rotor magnets with respect to the field coils, reliable starting is achieved with the device. In other arrangements, of course, such a starting means 1117 may not be required, for example if the drive coils comprise ferrite cores within the field windings thereof or other coil/magnet configurations to assist with self starting of the rotor which will be appreciated by the skilled addressee.

The field coil windings of drive coils 1115 and 1116 may be driven either in series or in parallel, however it is important to ensure the field from each coil is in phase so that (for instance) both generate a north pointing field that is exerted upon the rotor magnets simultaneously. Ideally the coil faces lie very close (0.5 mm) to the button magnets fixed on the rotor. The rotor magnets (1103 to 1106) depicted in the present exemplary rotor system 1100 are pole magnets. Magnets 1103 to 1106 may be aligned such that the flat faces of rotor magnets 1103 and 1105 are aligned to have \opposite polarity (i.e. opposite polar alignment) to that of rotor magnets 1104 and 1106 as shown by the pole marking on the faces ('s' and 'n') of the rotor magnets as depicted in FIG. 25.

The sensor means 1119 (in the present example, a hall-effect device, however, other suitable sensor devices may also be used) is used to detect the approach of the rotor magnets towards the drive coils as the rotor spins. In this manner, a pulsed current is applied to the field coils at exactly the right moment to drive the rotor at high speed.

In particular arrangements of the rotor system 1100, the magnetic fields present are desirably suppressed as much as possible to limit drag on the rotor 1101 in operation due to electromagnetic interactions with static components of the system. To avoid such drag on the rotor 1101 due to, for example, electromagnetic eddy currents, a field shield 1121 is provided in the housing 1122 and located such as to guide the magnetic fields of the rotor magnets 1103 to 1106 and the drive coils 1115 and 1116 away from the rotor support bearing 1107. The field shield 1121 may comprise a ferroelectric object, for example an iron washer as depicted in FIG. 24.

Figure 27:
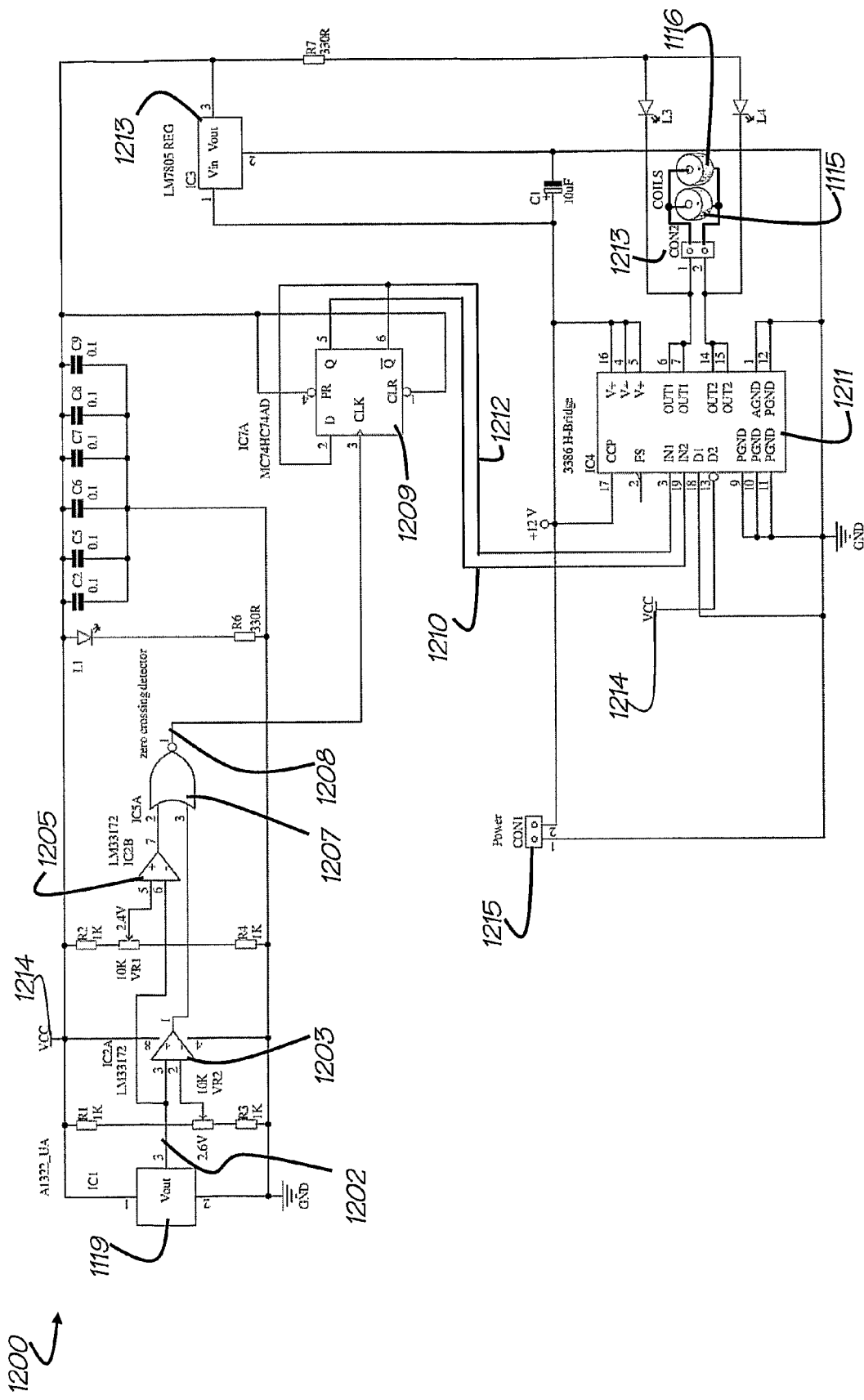
FIG. 27 depicts an exemplary drive circuit for operation of the rotor systems and apparatus described herein, wherein R1-R6 are resistors, C1 to C9 are capacitors, L1 to L4 are optional light emitting diodes, IC1 is a sensor (e.g. a Hall-effect sensor) used to derive the timing of the drive circuit; IC2A and IC2B are comparators for analysing the output from sensor IC1, IC3 is a voltage regulator, IC4 is an integrated circuit which contains a H-Bridge; IC5A is an logic OR-gate; and IC7A is a D-Flip-Flop.

FIG. 27 depicts an example drive circuit 1200 for operation of the rotor systems and apparatus described herein. In drive circuit 1200, R1-R6 are resistors, C1 to C9 are capacitors, L1 to L4 are optional light emitting diodes, IC1 is a sensor (e.g. a Hall-effect sensor) used to derive the timing of the drive circuit; IC2A and IC2B are comparators for analysing the output from sensor IC1, IC3 is a voltage regulator, IC4 is an integrated circuit which contains a H-Bridge; IC5A is an logic OR-gate; and IC7A is a D-Flip-Flop. In circuit 1200, diodes L1 to L4 are optional light emitting diodes used as a visual indication to an operator to indicate when the coils 1115 and 1116 are switching and to show when pulses are being detected by the Hall-effect sensor device 1119. The circuit 1200 would still function if diodes L1-L4 were removed. The capacitors C2-C9 are necessary to ensure transient noise on the power line does not cause 'glitches' with the digital circuitry, and are distributed across the circuit board as is standard practice for any digital circuit as would be appreciated by the skilled addressee.

Figure 28:
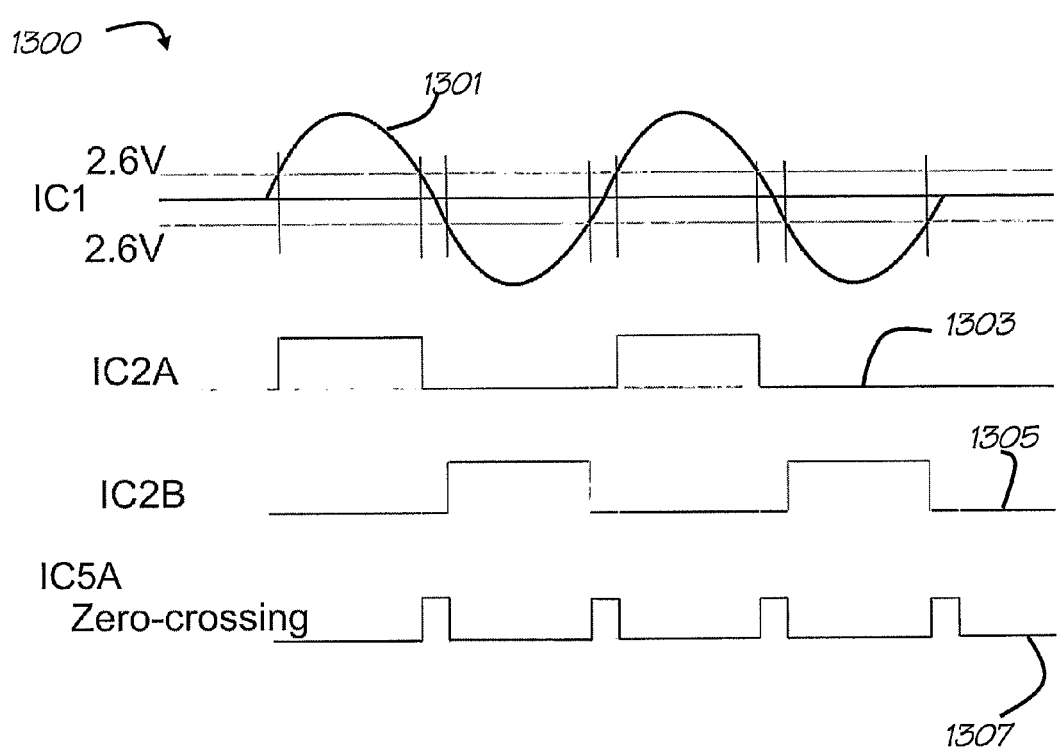
FIG. 28 shows exemplary drive signals for operation of the rotor systems and apparatus described herein in conjunction with the exemplary drive circuit of FIG. 27.

The present circuit 1200 is described with respect to the arrangement of rotor system 1100 described above, however, minor modifications to the circuitry as would be appreciated by the skilled addressee are also envisaged for adaptation of the drive circuit to variations of the rotor system as described herein. Also, specific model numbers specified in drive circuit 1200 are exemplary only and may be substituted in accordance with requirements as would be appreciated by the skilled electronics technician. Operation of the circuit 1200 is described below in conjunction with the control signals 1300 depicted in FIG. 28.

In the present arrangement, the Hall-effect sensor device 1119 (IC1—eg product no. A1322) is used to sense the orientation and strength of the magnetic field from the rotor magnets (1103 to 1106) fixed to the rotor 1101. In the absence of a magnetic field, the output of IC1 on connection line 1202 is at half the supply voltage, typically, VCC=5 volts to drive the integrated circuits of circuit 1200. Voltage regulator IC3 1213 (e.g. product no. LM7805) in the present circuit 1200 provides a regulated 5 volt output at VCC 1214 from an unregulated voltage input at CON1 1215, which is the voltage input to the circuit. In the present example, the unregulated input is typically in the range 8 to 18 volts (nominally 12V), which is converted to a 5 volt VCC by IC3 1213 being the maximum voltage for the integrated circuits.

Depending on the orientation of IC1 to the field of the rotor magnet approaching the sensor 1119 when in operation, the output voltage on line 1202 will increase or decrease proportional to the field strength sensed from the approaching rotor magnet. Thus, a sine-wave output (1301 of FIG. 28) is generated on line 1202 from IC1 as the magnetic field alternates in response to rotation of the rotor.

The sine wave output 1301 is applied to comparators IC2A 1203 and IC2B 1205 that, in the present example, are set at trigger voltages of 2.6V and 2.4 volts respectively. Thus, a square wave output (signal 1303 of FIG. 28) is generated from IC2A when the sine wave 1301 exceeds 2.6 volts and similarly with IC2B, a square wave output (signal 1305 of FIG. 28) is observed when the sine wave 1301 travels below 2.4 volts. The output from both comparators 1203 and 1205 are input to OR-gate IC5A 1205 to generate a pulsed control signal (signal 1307 of FIG. 28) on OR-gate output communication line 1208 corresponding to every zero-crossing of the sine-wave 1301 output from sensor 1119, The zero crossing output 1208 is used to drive D-Flip-Flop 1209 (IC7A—e.g. product no. MC74HC74AD). Flip-flop 1209 toggles its output (on communication lines 1210 and 1212) on each rising edge of the zero crossing trigger signal 1307. Each complementary output on lines 1210 and 1212 from flip flop 1209 is input to drive a H-Bridge driver, IC4 1211 (e.g. product no. 3386H-Bridge). The H-bridge is an electronic circuit which enables a voltage to be applied across a load in either direction. The polarity of the input voltage applied to the H-Bridge inputs is reflected at the outputs i.e. a positive input to IN1 or IN2 on the device (pins 3 and 19 respectively) results in a positive voltage at the outputs OUT1 or OUT2 (pins 6 and 7). The H-Bridge therefore can reverse the voltage at CON2 1215 applied to the field coils 1115 and 1116 and thereby reverse the polarity of the magnetic field from the coils used to drive the rotor apparatus. In the present arrangement, H-Bridge 1211 is configured to apply a reversible voltage across the field drive coils 1115 and 1116 shown in the present arrangement to be connected in parallel to H-bridge output connection CON2 1213. Drive coils 1115 and 1116 are driven in parallel in this arrangement to generate in-phase magnetic fields and thereby drive the rotor 1101 with electromagnetic pulses that are appropriately synchronized with its position to facilitate operation of the rotor system as described above for an auto-synchronous time-gated fluorescence detection apparatus and system. In the present arrangement, it has been found that a drive current of about 150 mA delivered to each of the drive coils 1115 and 1116 of rotor system 1100 is sufficient to drive the rotor 1101 at about 16,000 rpm, however other suitable drive currents in accordance with requirements for specific parts used in the apparatus and in accordance with operation requirement are envisaged. For example the drive current supplied to the drive coils may be in the range of about 1 mA to about 1 A as required. It will be appreciated that such a small drive current (i.e. 150 mA) to the drive coils would generate a relatively weak magnetic field for driving the rotor. Indeed, it is found that the rotor may be driven with such low currents at high speeds in a resonant manner relative to the location of the sensor 1119 in the housing 1122 with respect to the position of the drive coils 1115 and 1116. In this respect, it is realised that the sensor 1119 acts as a timing sensor relative to the location in the housing of the drive coils, and mis-location of the sensor with respect to the drive coils will result in inefficient timing signals for driving the rotor, and low operation speeds. The location of the sensor 1119 circumferentially with respect to at least one of the drive coils 1115 or 1116 is therefore an important factor to consider when locating the sensor in the rotor system housing. In some arrangements of the rotor system, an adjustment means may be provided on sensor 1119 to enable tuning of the signal 1301 output from the sensor. The adjustment means may be for example, means for re-locating the sensor within the housing with respect to the location of at least one of the drive coils. The adjustment means may provide means for moving the sensor within the housing circumferentially with respect to the location of at least one of the drive coils.

Control of the rotation speed of the rotor using the circuit 1200 of FIG. 27 may be realised by a variety of means as would be appreciated by the skilled addressee. For example, the rotation speed may be varied by varying the voltage supplied to the H-bridge driver 1211.

In other exemplary arrangements, the circuit 1200 may further be adapted to drive a pulsed excitation source, for example an LED or flashlamp light source, also appropriately synchronised with the position of the rotor to facilitate operation of the rotor system as described above for an auto-synchronous time-gated fluorescence detection apparatus and system. The excitation light source drive voltage may be derived from the zero-crossing signal output 1307 from OR-gate 1207, one or more outputs of D-Flip-Flop 1209, one or more outputs of H-Bridge 1211 or other suitable signal derived therefrom. An appropriate trigger signal to drive such an excitation source (e.g. LED or flashlamp) could be derived simply from the zero crossing pulses 1307 and used to gate a clock signal of higher frequency. The light source could be then be triggered after a certain number of clock pulses as required. A suitable microcontroller circuit (not shown), using the zero-crossing signal 1307 as an input thereto (i.e. using a signal derived from sensor 1119), may be used to deduce the required timing interval to energise the excitation light source (and for how long, i.e. the light source pulse length) to coincide with the actual position of the rotor vanes. The microcontroller may also be used to derive the timing of the pulses used to activate the drive coils to drive the rotor at a desired rotation speed. The design, and operation, including suitable software code for the microcontroller, for such a microcontroller control circuit would be appreciated by a skilled electronics engineer. As will also be appreciated, the physical placement of the sensor 1119 in rotor apparatus 1100 may not be as critical since the microcontroller (which typically operates at clock speeds of ~10 MHz compared with the 5,000 to 80,000 kHz rotation speed of the rotor in operation) can be used to deduce the actual location of the rotor arms and activate the drive coils (and an LED if present) as required. Of course, as described above, in particular arrangements the excitation light source may be a continuous wave light source, hence excitation pulse timing circuitry is not required.

It will be appreciated that the methods/apparatus/devices/systems described/illustrated herein above at least substantially provide a means for providing a time gated luminescence detection system and/or means for converting any existing microscope system into a time gated luminescence detection system, and also an auto-synchronous time gated luminescence detection microscope system wherein the emission and excitation states of the system are inherently synchronised.

The methods/apparatus/devices/systems described/illustrated described herein, and/or shown in the drawings, are presented by way of example only and are not limiting as to the scope of the invention. Unless otherwise specifically stated, individual aspects and components of the methods/apparatus/systems may be modified, or may have been substituted therefore known equivalents, or as yet unknown substitutes such as may be developed in the future or such as may be found to be acceptable substitutes in the future. The methods/apparatus/systems described herein may also be modified for a variety of applications while remaining within the scope and spirit of the claimed invention, since the range of potential applications is great, and since it is intended that the present methods/apparatus/systems be adaptable to many such variations.

The invention claimed is:

1. An apparatus for use in a time gated luminescence detection system, the apparatus comprising:
   a) a movement axis;
   b) an upper surface and a lower surface, the upper surface having a greater distal extent from the movement axis than the lower surface;
   c) a first communication portion for providing a first optical communication path between an illumination source location and a sample location, wherein the first communication portion comprises a reflective surface distal the movement axis and contiguous with both the upper and lower surfaces and the distal extent of the apparatus, wherein the reflective surface is aligned for deflecting light between the illumination source location and the sample location;
   d) a second communication portion for (i) providing a second optical communication path between the sample location and a detection location, the second communication portion being operable to enable detection at the detection location of a desired optical emission from an illuminated sample which in use is located at the sample location via the second optical communication path, and (ii) concurrently preventing optical communication on the first optical communication path; and
   e) a gate portion for gating the first and second optical communication paths; the apparatus being capable of being arranged to provide the first optical communication path, to gate the first and second optical communication paths and to provide the second optical communication path in a sequential manner thereby to respectively place the apparatus in an excitation state, a gated state and a detection state.

2. An apparatus as claimed in claim 1 wherein the location of the first and second communication portions and the gate portion are each fixed relative each other during movement of the apparatus such that, in use, repeated movement of the apparatus provides autonomous synchronisation between the emission and detection states.

3. An apparatus as claimed in claim 1 wherein the gate portion is integral with the first communication portion.

4. An apparatus as claimed in claim 1 wherein the gate portion is capable of preventing optical communication on the first optical communication path.

5. An apparatus as claimed in claim 1 wherein the second communication portion is a void space in the apparatus which is defined by the first communication portion, and wherein the second optical communication path comprises the void space.

6. An apparatus as claimed in claim 1 wherein the second communication portion comprises a transparent portion, and the second optical communication path comprises the transparent portion.

7. An apparatus as claimed in claim 1 wherein the apparatus provides a self-synchronising time gated fluorescence detection system.

8. An apparatus as claimed in claim 1 wherein a portion of the reflective surface comprises the gate portion.

9. An apparatus as claimed in claim 1 wherein the first communication portion comprises at least one elongate vane extending from the movement axis.

10. An apparatus as claimed in claim 9 wherein in the excitation state the vane is adapted for blocking light from the sample location from impinging on the detection location.

11. An apparatus as claimed in claim 1 wherein the second communication portion comprises a substantially transparent portion through the apparatus for facilitating optical communication between the sample and detection locations.

12. An apparatus as claimed in claim 11 wherein the second communication portion comprises a plurality of substantially transparent portions.

13. An apparatus as claimed in claim 1 wherein in the excitation state the reflective surface is adapted for deflection of light from an external light emitting source located at the illumination source location to a sample which in use is located at the sample location, the sample comprising at least one autofluorophore responsive to light from the light source such that the autofluorophore emits autofluorescence with an autofluorescence lifetime.

14. An apparatus as claimed in claim 13 wherein the first communication portion is adapted to substantially prevent the autofluorescence from impinging on the detection location for a period of time of at least the autofluorescence lifetime.

15. An apparatus as claimed in claim 1 wherein the reflective surface is arcuate.

16. An apparatus as claimed in claim 1 wherein the first communication portion comprises at least one non-reflective portion adjacent the reflective surface wherein the non-reflective portion comprises the gate portion.

17. An apparatus as claimed in claim 16 wherein the first communication portion comprises two non-reflective portions, each non-reflective portion being adjacent the reflective surface.

18. An apparatus as claimed in claim 1 further comprising a mover adapted to move the apparatus with respect to the movement axis wherein the mover is configurable for sequentially:
moving the apparatus to the excitation state;
moving the apparatus with respect to the movement axis to the gated state wherein the first optical communication path is gated by the gate portion;
maintaining the apparatus in the gated state for a first period of time; and
moving the apparatus with respect to the movement axis to the detection state at a time after the first period.

19. An apparatus as claimed in claim 18 wherein the mover is adapted for continuous movement between the excitation state, the gated state and the detection state.

20. An apparatus as claimed in claim 1 wherein the movement axis is a pivot axis.

21. An apparatus as claimed in claim 20 wherein the pivot axis is a rotation axis and the apparatus rotates about the rotation axis.

22. An apparatus as claimed in claim 1 wherein the apparatus is a rotor adapted for rotation about the movement axis, wherein the rotor is adapted to be driven into rotation by the mover.

23. An apparatus as claimed in claim 22 wherein the rotor is configurable for rotation speed of between 5,000 and 60,000 revolutions per minute.

24. An apparatus as claimed in claim 1 wherein the apparatus is mounted in a housing.

25. An apparatus as claimed in claim 24 wherein the housing comprises a first and second aperture aligned with the sample and detection locations to allow light to traverse the apparatus and the housing when the apparatus is in the detection state.

26. An apparatus as claimed in claim 24 wherein internal surfaces of the housing are either absorbing, non-reflective or absorbing and non-reflective.

27. An apparatus as claimed in claim 1 wherein, with exception of the reflective surface located on the first communication portion, the surfaces of the apparatus are non-reflective.

28. An optical device comprising one or a plurality of focusing elements and an apparatus as claimed in claim 1.

29. An optical device as claimed in claim 28 wherein the plurality of focusing elements form an objective lens system.

30. An optical device as claimed in claim 28 adapted for use in conjunction with a microscope.

31. An autosynchronous time gated fluorescence detection method
comprising the steps of:
a) providing an apparatus for autonomous synchronisation between an excitation state and a detection state, the apparatus comprising:
a1) a movement axis;
a2) an upper surface and a lower surface, the upper surface having a greater distal extent from the movement axis than the lower surface;
a3) a first communication portion for providing a first optical communication path between an illumination source location and a sample location, wherein the first communication portion comprises a reflective surface aligned for deflecting light between the illumination source location and the sample location, wherein the reflective surface is aligned for deflecting light between the illumination source location and the sample location;
a4) a second communication portion for (i) providing a second optical communication path between the sample location and a detection location, the second communication-portion being operable to enable detection at the detection location of a desired optical emission from an illuminated sample located at the sample location via the second optical communication path; and (ii) concurrently preventing optical communication on the first optical communication path; and
a5) a gate portion for gating the first and second optical communication paths; the apparatus being capable of being arranged to provide the first optical communication path, to gate the first and second optical communication paths and to provide the second optical communication paths in a sequential manner thereby to respectively place the apparatus in an excitation state, a gated state and a detection state;

b) providing a light source at the first location for excitation of fluorescence in a sample located at the sample location in the excitation state, the sample comprising autofluorophores having an autofluorescence lifetime and probe fluorophores having a probe fluorescent lifetime greater than the autofluorescence lifetime;

c) providing a detector located at the detection location for detection of light from the sample location in the detection state;

d) moving the apparatus with respect to the movement axis into the excitation state such that the first communication portion is adapted to enable autofluorescence and probe fluorescence to be excited in the sample by the light source;

e) moving the apparatus with respect to the movement axis into the gated state wherein the first optical communication path is gated by the gate portion;

f) maintaining the apparatus in the gated state for a time at least the duration of the autofluorescence lifetime;

g) moving the apparatus with respect to the movement axis into the detection state such that the probe fluorescence is permitted to be detected by the detector; and h) optionally repeating steps (d) to (g) in accordance with requirements.

32. A method as claimed in claim 31 wherein the movement axis is a pivot axis, the apparatus is a rotor, the first communication portion is one or a plurality of vanes extending radially from the pivot axis, wherein steps (d) to (g) are provided by rotation of the rotor about the pivot axis.

33. A system for autosynchronous time gated fluorescence detection comprising:

an apparatus for autonomous synchronisation between an excitation state and a detection state, the apparatus configurable for movement between the excitation and detection states and comprising:

a) a movement axis;

b) an upper surface and a lower surface, the upper surface having a greater distal extent from the movement axis than the lower surface;

c) a first communication portion for providing a first optical communication path between an illumination source location and a sample location, wherein the first communication portion comprises a reflective surface aligned for deflecting light between the illumination source location and the sample location, wherein the reflective surface is aligned for deflecting light between the illumination source location and the sample location;

d) a second communication portion for (i) providing a second optical communication path between the sample location and a detection location, the second communication portion being operable to enable detection at the detection location of a desired optical emission from an illuminated sample which in use is located at the sample location via the second optical communication path; and (ii) concurrently preventing optical communication on the first optical communication path; and e) a gate portion for gating the first and second optical communication paths; the apparatus being capable of being arranged to provide the first optical communication path, to gate the first and second optical communication paths and to provide the second optical communication paths in a sequential manner thereby to respectively place the apparatus in an excitation state, a gated state and a detection state; a light source at the illumination source location for excitation of fluorescence in a sample which in use is located at the sample location in the excitation state, the sample comprising autofluorophores having an autofluorescence lifetime and probe fluorophores having a probe fluorescent lifetime greater than the autofluorescence lifetime; a detector located at the detection location for detection of light from the sample location in the detection state; and a mover for: moving the apparatus with respect to the movement axis into the excitation state such that the first communication portion is adapted to enable autofluorescence and probe fluorescence to be excited in the sample by the light source; moving the apparatus with respect to the movement axis to the gated state wherein the first optical communication path is gated by the gate portion; maintaining the apparatus in the gated state for a time at least the duration of the autofluorescence lifetime; and moving the apparatus with respect to the movement axis into the detection state such that the probe fluorescence is permitted to be detected by the detector.

* * * * *